US006962791B2

(12) United States Patent
Hultgren et al.

(10) Patent No.: US 6,962,791 B2
(45) Date of Patent: Nov. 8, 2005

(54) TREATMENT OR PROPHYLAXIS OF DISEASES CAUSED BY PILUS-FORMING BACTERIA

(75) Inventors: Scott Hultgren, Ballwin, MO (US); Meta Kuehn, Berkeley, CA (US); Zheng Xu, Blue Bell, PA (US); Derek Ogg, Uppsala (SE); Mark Harris, Uppsala (SE); Matti Lepisto, Lund (SE); Charles Hal Jones, Saint Louis, MO (US); Jan Kihlberg, Dalby (SE)

(73) Assignees: Washington University, St. Louis, MO (US); Siga Pharmaceuticals, Inc., New York, NY (US)

( * ) Notice: Subject to any disclaimer, the term of this patent is extended or adjusted under 35 U.S.C. 154(b) by 627 days.

(21) Appl. No.: 09/799,608

(22) Filed: Mar. 7, 2001

(65) Prior Publication Data

US 2002/0146428 A1 Oct. 10, 2002

Related U.S. Application Data

(60) Division of application No. 08/640,877, filed on Oct. 10, 1996, now Pat. No. 6,420,127, which is a division of application No. PCT/US94/13455, filed on Nov. 8, 1994, which is a continuation-in-part of application No. 08/154,035, filed on Nov. 18, 1993, now abandoned.

(51) Int. Cl.$^7$ .................... G01N 33/569; A61K 39/108; A61K 39/02
(52) U.S. Cl. ............... 435/7.37; 424/241.1; 424/242.2; 424/257.1; 435/849
(58) Field of Search .......................... 424/241.1, 242.2, 424/257.1; 435/7.37, 849

(56) References Cited

FOREIGN PATENT DOCUMENTS

| EP | 0464276 | 1/1992 |
|---|---|---|
| WO | 9104543 | 4/1991 |
| WO | 9302209 | 2/1993 |

OTHER PUBLICATIONS

Seib, Paul A., "1,6–Anhydro–4–O–Benzyl–β–D–Glucopyranose", Carbohydrate Research, 8:101–109, 1968.
Copper, David B., et al., "Use of Carbohydrate Derivatives for Studies of Phosphorus Sterochemistry. Part I. Sterochemistry of 1,3,2–dioxaphosphorinan–2–ones and Synthesis of Optically Active Phosphine Oxides", J. Chem Soc. Perkin Trans., 1:1043–1048, 1974.
Haque, Mohammed Ekramul, et al., "Radioselective Monoalkylation of Non–protected Glycopyranosides by the Dibutyltin Oxide Method", J. Chem. Pharm. Bull., 33:2243–2255, 1985.
Flowers, Harold M., "Selective Benzylation of Some D–galactopyranosides", Carbohydrate Research, 100:418–423, 1982.

Ullmann, U.R., "An Algorithm for Subgraph Isomorphism", Journal of the Association for Computing Machinery, vol. 23, No. 1, pp. 31–42, 1976.
Aqvist et al., "A New Method for Predicting Binding Affinity in Computer–aided Drug Design", Protein Engineering, vol. 7, No. 3, pp. 385–391, 1994.
Messerschmidt et al., "Crystal Orientation and X–ray Pattern Prediction Routiness for Area–Detector Diffractometer Systems in Macromolecular Crystallography", Journal of Applied Crystallography, vol. 20, part 4, pp. 306–315, 1987.
Normark, S. et al., Genetics and Bigenesis of *Escherichia coli* Adhesin, In Microbial Lectins and Agglutinins: Properties and Biological Activity, Wiley Interscience Publication, New York, pp. 113–143, 1986.
Wessel, Hans Peter, "Sulfated 1, 6–Anhydro–4–O(β–D–Glucopyranosyluronate)–β–D–Glucopyranosyl Derivatives: Syntheses and Conformations", Journal of Carbohydrate Chemistry, vol. 11, No. 8, pp. 1039–1052, 1992.
Kuehn et al., Immunoglobulin–like PapD Chaperone Caps and Uncaps Interactive Surfaces of Nascently Translocated Pilus Subunites, *Proc. Natl. Acad. Sci. USA*, vol. 88, pp. 10586–10590, Dec. 1991.
Striker et al., Stable Pilus Subunit–Chaperone Complexes are Intermediates in Bacterial Pilus Assembly, (abstract 1357), *FASEB J.*, vol. 7, No. 7, pp. a1285, 1993.
Weber et al., Pilus Expression by H. Influenza b Requires a Chaperone, (abstract 1071), *Ped. Res.*, vol. 4 (pt. 2), p. 191a, 1992.
Jacob–Dubuisson et al., Initiation of Assembly and Association of the Structural Elemetns of a Bacterial Pilus Depend on Two Specialized Tip Proteins, *The EMBO Journal*, vol. 12, No. 3, pp. 837–847, 1993.
Rouche et al., Pediatr. Nephrol., vol. 6, pp. 587–596 (1992) "The molecular study of bacterial virulence: a review of current approaches, illustrated by the study of adhesion in uropathogenic *Eschericia coli*".
Stoddard et al., Proc. Natl. Acad. Sci., vol. 90, pp 1146–1153 (1993) "Molecular recognition analyzed by docking simulations: The aspartate receptor and isocitrate dehydrogenase from *Eschericia coli*".

(Continued)

*Primary Examiner*—Rodney P Swartz
(74) *Attorney, Agent, or Firm*—Burns, Doane, Swecker & Mathis, L.L.P.

(57) ABSTRACT

Novel methods for the treatment and/or prophylaxis of diseases caused by tissue-adhering bacteria are disclosed. By interacting with periplasmic molecular chaperones it is achieved that the assembly of pili is prevented or inhibited and thereby the infectivity of the bacteria is diminished. Also disclosed are methods for screening for drugs as well as methods for the de novo design of such drugs, methods which rely on novel computer drug modelling methods involving an approximative calculation of binding free energy between macromolecules. Finally, novel pyranosides which are believed to be capable of interacting with periplasmic molecular chaperones are also disclosed.

12 Claims, 25 Drawing Sheets

Figure 1A:
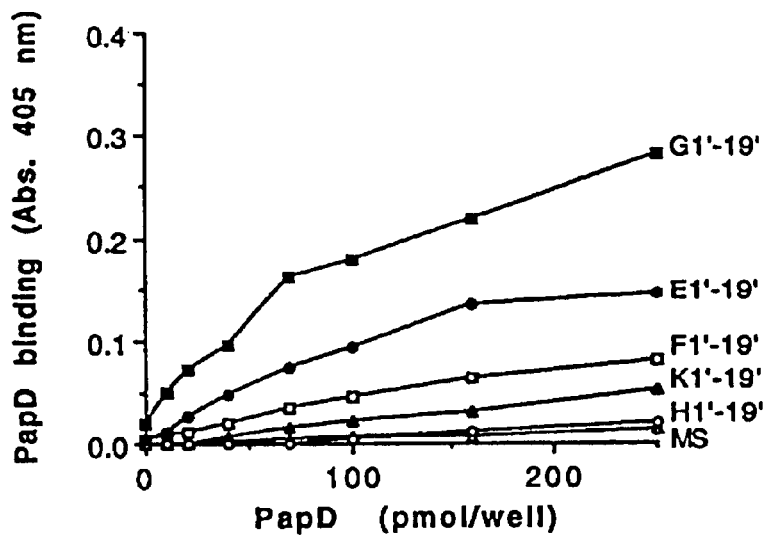

(1 of 25 Drawing Sheet(s) Filed in Color)

OTHER PUBLICATIONS

Smyth "Assays for fimbrial Adhesins" in *Immunochemical and molecular genetic analysis of bacterial pathogens,* ed. by Owen et al., Elsevier Science Publishers, pp. 334–244 (1988).

Navia et al., Trends Pharmacol. Sci., vol. 14, pp. 189–195 (1993) "Structure–based drug design: applications in immunopharmacology and immunosupression".

Krogfelt, "Bacterial Adhesins: Genetics, Biogenesis, and Role in Pathogenesis of Fimbrial Adhesins in *Escherichia coli*", in *Reviews of Infectious Diseases,* pp. 721–735, The University of Chicago (1991).

Allen, B. L. et al. "Nucleotide Sequence and Functions of mrk Determinants Necessary for Expression of Type 3 Fimbriae in *Klebsiella pneumoniae.*" J. Bacteriol 173, 916–920.

Amit, A.G. et al. "Three–Dimensional Structure of an Antigen–Antibody Complies at 2.8 A Resolution." Science, 230, 747–753, 1986.

Baga, Monica et al. "Biogenesis of *E. coli* Pap Pili: PapH, a Minor Plin Subunit Involved in Cell Anchoring and Length Modulation." Cell. 49, 241, 1987.

Bakker, D. et al. "Structure and function of periplasmic chaperone–like proteins involved in the biosynthesis of K88 and K99 fimbriae in enterotoxigenic *Escherichia coli.*" Molec. Microbiol., 5, 875.

Ben–Naim, A. et al. "Solvation thermodynamics of nonionic solutes." J. Chem. Phys., 81, 2016–2027.

Bertin, Yolande, et al. "The ClpE protein involved in biogenesis of the cs31A capsule–like antigen is a member of a periplasmic chaperone family in gram–negative bacterial." Fems Microbiol. Lett., 108, 59.

Bobbyer, David N. A. et al. "New Hydrogen–Bond Potentials for Use in Determining Energetically Favorable Binding Sites on Molecules of Known Structure." J. Med. Chem., 32, 1083–1094.

Brint, A.T., et al. "Pharmacophoric pattern matching in files of 3D chemical structures: comparison of geometric searching algorithms." J. Mol. Graphics, 5, 49–56.

Chandler, David et al. "Van der Waals Picture of Liquids, Solids, and Phase Transformations." Science, 220, 787–794.

Chemical Abstracts, RN 149563–08–6 (p. 88, line 2).

Clouthier, Sharon C. et al. "Characterization of Three Fimbrial Genes, sefABC, of *Salmonella enteritidis.*" J. Bacteriol., 175, 2523.

Dodson, Karen W. et al. "Outer–membrane PapC molecular usher discriminately recognizes periplasmic chaperone–pilus subunit complexes." Proc. Natl. Acad. Sci. 1993, 90 3670–3674.

Galyov, E.E. et al. "Expression of the envelope antigen F1 of *Yersinia pestis* is mediated by the product of cafLM gene having homology with the chaperone protein PapD of *Escherichia coli.*" FEBS Lett., 286, 79.

Gerlach, Gerald–F. et al. "Identification and Characterization of the Genes encoding the Type 3 and Type 1 Fimbrial Adhesins of *Klebsiella pneumonia.*" J. Bacteriol., 171–1262–70.

Goodford, P. J. "A Computational Procedure for Determining Energetically Favorable binding sites on Biologically Important Macromolecules." J. Med. Chem. 1985, 28, 849–857.

Hirschmann, Ralph et al. "Nonpeptidal Peptidomimetics with a β–D–Glucose Scaffolding. A Parial Somatostatin Agonist Bearing a Close Structural Relationship to a Potent, Selective Substance P. Antagonist." J. Am. Chem. Soc. 1992, 114, 9217–9218.

Holmgren, Anders et al. "Preliminary X–ray Study of PapD Crystals from Uropathogenic *Escherichia coli.*" J. Mol. Biol. 203, 279, 1988.

Holmgren, Anders et al. "Crystal structure of chaperone protein PapD reveals an immunoglobulin fold." Nature 342, 248, 1989.

Holmgren, Anders et al. "Conserved immunoglobulin–like features in a family of periplasmic pilus chaperones in bacteria." The EMBO Journal, 11, 4, 1617–1622.

Hultgren, Scott J. et al. "The PapG adhesin of uropathogenic *Escherichia coli* contains separte regions for receptor binding and for the incorporation into the pilus." Proc. Natl. Acad. Sci. USA, 86, 4357.

Hultgren, Scott J. et al. "Chaperone–Assisted Assembly and molecular Architecture of Adhesive Pili." Annu. Rev. Microbiol., 45, 383–415.

Hällgren, Christer et al. "Synthesis of a Site–Specific Deuterium Substituted Methyl–β–D—glucan decasaccharide." J. Carbohydr. 12 (3), 309–333.

Iriate, Maite et al. "The Myf fibrillae of *Yersina enterocolitica.*" Mol. Microbiol., 9, 507.

Jalajakumari, M.B. et al. "Genes for biosynthesis and assembly of CS3 pili of CFA/II enterotoxigenic *Escherichia coli:* novel regulation of pilus by bypassing and amber codon. "Mol. Microbiol., 3, 1685.

Jorgensen, William L. "Optimized Intermolecular Potential Functions for Liquids Alcohols." J. Phys. Chem., 90, 1276–1284.

Kawaminami, M. et al. "The Fundamental Structure of Cycasin, (Methyl–ONN–azoxy)methyl β–D–Glucopyranoside." Acta Crystallogr. Section B 107 (37), 2026, 1981.

Klemm, P. "FimC, a chaperone–like periplasmic protein of *Escherichia coli* involved in biogenesis of type 1 fimbriae." Res> Microbiol., 143, 831.

Kuehn, Meta J. et al. "Immunoglobulin–like PapD chaperone caps and uncaps interactive surfaces of nascently translocated pilus subunits." Proc. Natl. Acad. Sci. 88, 10586–10590.

Lam, Kelvin, T. et al."HSP70 Binds Specifically to a Peptide Derived from the Highly Conserved Domain(1) Region of P53." Biochem and Biophys., Res. Comm. 184, 167, 1992.

Landry, Samuel J. et al. "The Chaperonin GroEL Binds a Polypeptide in an α–Helical Conformation." Biochemistry, 30, 7359.

Landry, Samuel J. et al. "Different conformations for the same polypeptide bound to chaperone DnaK and GroEL." Nature, 1992, 355, 455.

Lee, Frederick S. et al. "Calculations of antibody–antigen interactions: microscopic and semi–microscopic evaluation of the free energies of binding of phosphyorylcholine analogs to McPC603." Prot. Eng., 5, 215–228.

Lindberg, Frederik et al. "PapD, A Periplasmic Transport Protein in P–Pilus Biogenesis." J. Bacteriol. 171, 6052.

Linder et al., 1993, Genbank, acession No.: M886713.

Locht, Camille et al. "Common accessory genes for the *Bordetella pertussis* filamentous hemagglutinin and fimbriae share sequence similarities with the papD gene families." EMBO J., 11, 3175.

Lund, Björn et al. "The PapG protein is the α–D–galactopyranosyl–1(1→4)–β–D–galactopyranose–binding adhesin or uropathogenic *Escherichia coli*." Proc. Natl. Acad. Sci. USA, 84, 5898.

Patroni, Joseph J. et al. "The Selective Monobenzylidenation of Some Monosaccharides and Their Derivatives with α,α–Dimethoxytoluene." Aust. J. Chem. 1988, 41, 91–102.

Pratt, Lawrence R. et al. "Theory of the hydrophobic effect." J. Chem. Phys., 67, 3683–3704.

Raina, Satish, et al. "Identification and Transcriptional Analysis of the *Escherichia coli* htrE Operon Which Is Homologous to pap and Related Pilin Operons." J. Bacteriol., 175, 5009.

Roux, Benoit et al. "Molecular Basis for the Born Model of Ion Solvation." J. Phys. Chem., 94, 4683–4688.

Ryu, Seong–Eon et al. "Crystal Structure of an HIV–binding Recombinant Fragment of Human CD4." Nature, 348, 419.

Schmoll, Thomas et al. "Complete genetic organization and functional aspects of the *Escherichia coli* s fimbrial adhesion determinant: nucleotide sequence of the genes sfa B, C, D, E, F." Microb. Pathog., 9, 331.

Slonim, Lynn N. et al. "Interactive Surface in the PapD Chaperone Cleft is conserved in Pilus Chaperone Superfamily and essential in Subunit Recognition and Assembly." EMBO J. 11, 4747–56.

Strauch, Kathryn L. et al. "Characterization of degP, a Gene Required for Proteolysis in the Cell Envelope and Essential for Growth of *Escherichia coli* at High Temperature." J. Bacteriol. 171, 2689–2696.

de Vos, Abraham M. et al. "Human Growth Hormone and Extracellular Domain of Its Receptor: Crystal Structure of the Complex." Science, 1992, 225, 306.

Wang, Jihuai, et al. "Atomic structure of a Fragment of Human CD4 Containing Two Immunoglobulin–like Domains." Nature, 1990, 348, 411.

Warshel, Arieh et al. "Calculations of Electrostatic Interactions in biological Systems and in Solutions." 1984, Q. Rev. Biophys., 17, 283–422.

Willems, Rob J. L. et al. "Characterization of a *Bordetella pertussis* Fimbrial Gene Cluster which is located Directly Downstream of the Filamentous Haemagglutinin Gene." Molec. Microbiol., 6, 2661.

Aqvist, Johan. "Ion–Water Interaction Potentials Derived from Free Energy Perturbation Simulations." J. Phys. Chem., 94, 8021–8024.

Kuehn, Meta J. et al., "Structural Basis of Pilus Subunit Recognition by the PapD Chaperone." Science, 262, 1234–1241, 1993.

Hultgren, Scott J. et al. "Pilus and Nonpilus Bacterial Adhesins: Assembly and Function in Cell Recognition." 1993, Cell, 73, 887–901.

Hultgren, Scott J. et al. "Biogenesis of the Bacterial Pilus." 1991, Current Opinion in Genetics and Development, 1, 313–318.

Jones, C. Hal et al. "FimC is a Periplasmic PapD–like Chaperone that Directs Assembly of Type 1 Pili in Bacterial." Proc. Natl. Acad. Sci. USA, 90, 8397–8401.

Jacob–Dubuisson, Francoise et al. "A Novel Secretion Apparatus for the Assembly of Adhesive Bacterial Pili." Trends in Microbiology, 1–50–555.

Kuehn, Meta J. et al. "P pili in Uropathogenic *E. coli* are Composite Fibres with Distinct Fibrillar Adhesive Tips." 1992, Nature, 356, 252–255.

Hultgren, Scott J. et al. "PapD and Superfamily of Periplasmic Immunoglobulin–like Pilus Chaperones." Advances in Protein Chem., 44, 99–123.

Gething, Mary–Jane et al. "Protein Folding in the Cell." Nature, 355, 33, 1992.

Jones, C. Hal et al. "Adhesin Presentation in Bacterial Requires Molecular Chaperones and Ushers." Infect. and Imunity, 60, 4445–4451.

Jones, C. Hal et al. "Adhesin Presentation in Bacteria Requires Molecular Chaperones and Ushers." Infect. and Immunity, 60, 4445–4451.

a p-MeOPhCH(OMe)₂, TsOH / MeCN
b EtI, NaOH, NBu₄HSO₄ / CH₂Cl₂, H₂O
c tBuMe₂SiOTf, Et₃N / CH₂Cl₂ or tBuMe₂SiCl / pyridine
d NaCNBH₃, Me₃SiCl / MeCN
  or NaCNBH₃, HCl(Et₂O) / Et₂O
  DMSO, P₂O₅, Et₃N / THF
f PhMgCl / THF
g CAN / MeCN, H₂O a Imidazolyl tosylamide NaH / THF, rt, 66%
b NaN$_3$, NH$_4$Cl / EtOH, H$_2$O, reflux, 72%
c EtI, NaH / DMF or alkyl halide, NaH / THF
d NaCNBH$_3$, Me$_3$SiCl / MeCN

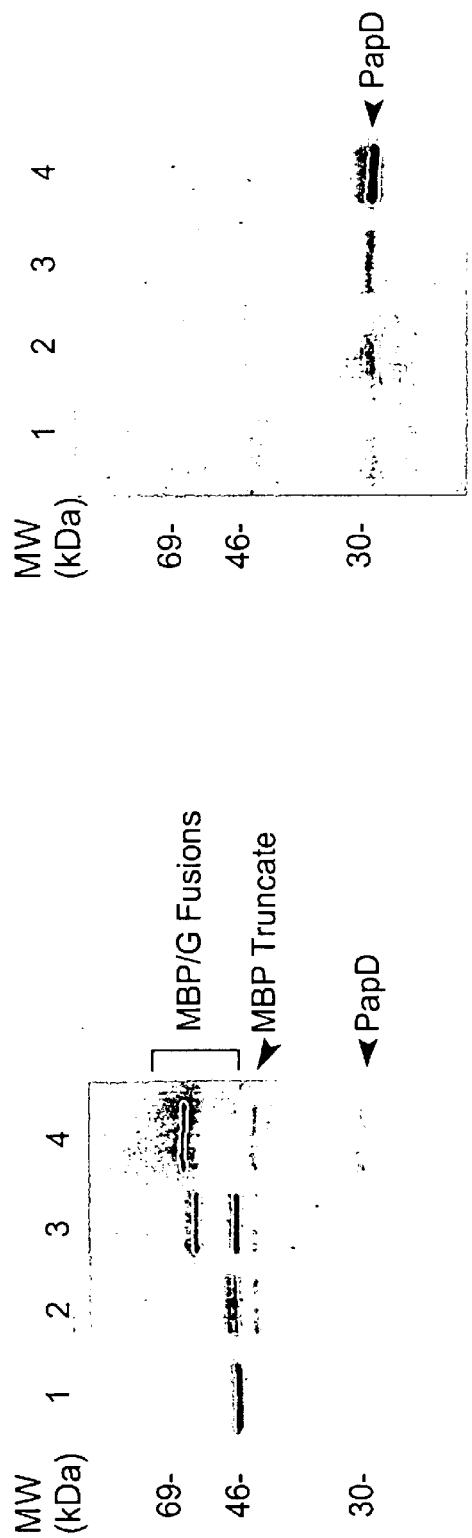
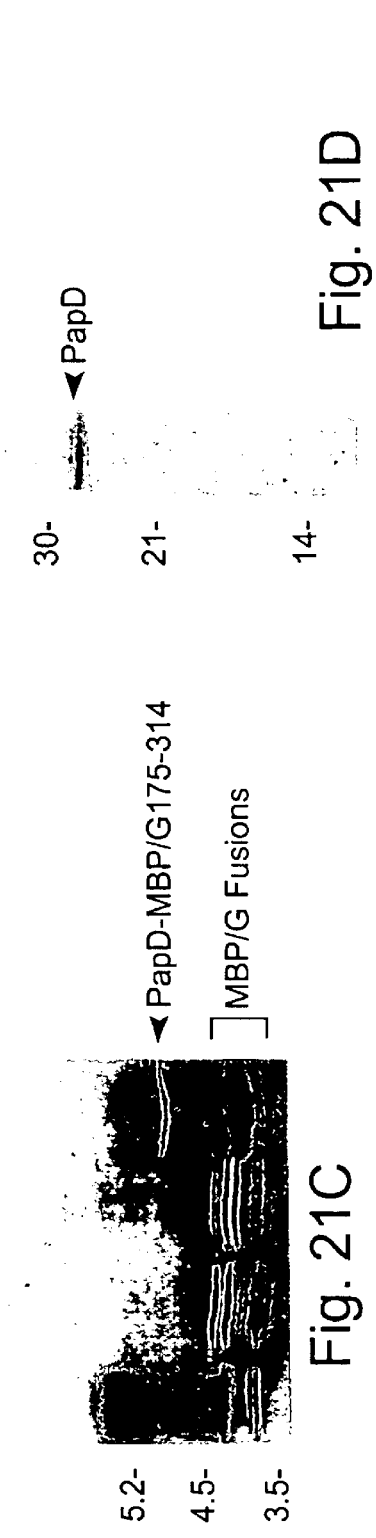
Fig. 21A
Fig. 21B
Fig. 21C
Fig. 21D

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 874 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli (ix) FEATURE:
        (A) NAME/KEY: CDS
        (B) LOCATION: 1..720

(ix) FEATURE:
        (A) NAME/KEY: sig_peptide
        (B) LOCATION: 1..63

(ix) FEATURE:
        (A) NAME/KEY: mat_peptide
        (B) LOCATION: 64..717

(x) PUBLICATION INFORMATION:
        (A) AUTHORS: Norgren, M.
            Baga, M.
            Tennet, J.M.
            Normark, S.
        (C) JOURNAL: Mol. Biol. Rep.
        (D) VOLUME: 12
        (F) PAGES: 169-178
        (G) DATE: 1987

(xi) SEQUENCE DESCRIPTION: SEQ ID NO: 1:

```
ATG ATT CGA AAA AAG ATT CTG ATG GCT GCC ATC CCC CTG TTT GTT ATA       48
Met Ile Arg Lys Lys Ile Leu Met Ala Ala Ile Pro Leu Phe Val Ile
-21 -20              -15                  -10

TCC GGG GCA GAC GCT GCT GTT TCG CTG GAC AGA ACC CGC GCG GTG TTT       96
Ser Gly Ala Asp Ala Ala Val Ser Leu Asp Arg Thr Arg Ala Val Phe
 -5               1               5                  10

GAC GGG AGT GAG AAG TCA ATG ACG CTT GAT ATC TCC AAT GAT AAC AAA      144
Asp Gly Ser Glu Lys Ser Met Thr Leu Asp Ile Ser Asn Asp Asn Lys
              15                  20                  25

CAA CTG CCC TAT CTT GCT CAG GCA TGG ATA GAA AAT GAA AAT CAG GAA      192
Gln Leu Pro Tyr Leu Ala Gln Ala Trp Ile Glu Asn Glu Asn Gln Glu
          30                  35                  40

AAA ATT ATT ACA GGG CCG GTT ATT GCC ACC CCT CCG GTT CAG CGC CTT      240
Lys Ile Ile Thr Gly Pro Val Ile Ala Thr Pro Pro Val Gln Arg Leu
      45                  50                  55

GAG CCG GGT GCG AAA AGC ATG GTC AGG CTG AGT ACC ACA CCG GAT ATC      288
Glu Pro Gly Ala Lys Ser Met Val Arg Leu Ser Thr Thr Pro Asp Ile
 60                  65                  70                  75

AGT AAA CTT CCT CAG GAC AGG GAA TCA CTG TTT TAT TTT AAT CTC AGG      336
Ser Lys Leu Pro Gln Asp Arg Glu Ser Leu Phe Tyr Phe Asn Leu Arg
              80                  85                  90

GAA ATA CCG CCG AGG AGT GAA AAG GCC AAT GTA CTG CAG ATA GCC TTA      384
Glu Ile Pro Pro Arg Ser Glu Lys Ala Asn Val Leu Gln Ile Ala Leu
          95                 100                 105

CAG ACC AAA ATA AAG CTT TTT TAT CGC CCG GCA GCA ATT AAA ACC AGA      432
Gln Thr Lys Ile Lys Leu Phe Tyr Arg Pro Ala Ala Ile Lys Thr Arg
     110                 115                 120

CCA AAT GAA GTA TGG CAG GAC CAG TTA ATT CTG AAC AAA GTC AGC GGT      480
Pro Asn Glu Val Trp Gln Asp Gln Leu Ile Leu Asn Lys Val Ser Gly
 125                 130                 135

GGG TAT CGT ATT GAA AAC CCA ACG CCC TAT TAT GTC ACT GTT ATT GGT      528
Gly Tyr Arg Ile Glu Asn Pro Thr Pro Tyr Tyr Val Thr Val Ile Gly
 140                 145                 150                 155

CTG GGA GGA AGT GAA AAG CAG GCA GAG GAA GGT GAG TTT GAA ACC GTG      576
Leu Gly Gly Ser Glu Lys Gln Ala Glu Glu Gly Glu Phe Glu Thr Val
              160                 165                 170
```

-continued

```
ATG CTG TCT CCC CGT TCA GAG CAG ACA GTA AAA TCG GCA AAT TAT AAT      624
Met Leu Ser Pro Arg Ser Glu Gln Thr Val Lys Ser Ala Asn Tyr Asn
            175                 180                 185

ACC CCT TAT CTG TCT TAT ATT AAT GAC TAT GGT GGT CGC CCG GTA CTG      672
Thr Pro Tyr Leu Ser Tyr Ile Asn Asp Tyr Gly Gly Arg Pro Val Leu
            190                 195                 200

TCG TTT ATC TGT AAT GGT AGC CGT TGC TCT GTG AAA AAA GAG AAA TAA      720
Ser Phe Ile Cys Asn Gly Ser Arg Cys Ser Val Lys Lys Glu Lys *
            205                 210                 215

TGTACCGCAA TAACGGTTAA ATGCGGGTGG GATATTATGG TTGTGAATAA AACAACAGCA    780

GTACTGTATC TTATTGCACT GTCGCTGAGT GGTTTCATCC ATACTTTCCT GCGGGCTGAA    840

GAGCGGGGTA TATACGATGA CGTCTTTACT GCAG                                874
```

(2) INFORMATION FOR SEQ ID NO: 2:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ile Arg Lys Lys Ile Leu Met Ala Ala Ile Pro Leu Phe Val Ile
-21 -20                 -15                 -10

Ser Gly Ala Asp Ala Ala Val Ser Leu Asp Arg Thr Arg Ala Val Phe
 -5              1               5                   10

Asp Gly Ser Glu Lys Ser Met Thr Leu Asp Ile Ser Asn Asp Asn Lys
            15                  20                  25

Gln Leu Pro Tyr Leu Ala Gln Ala Trp Ile Glu Asn Glu Asn Gln Glu
            30                  35                  40

Lys Ile Ile Thr Gly Pro Val Ile Ala Thr Pro Pro Val Gln Arg Leu
            45                  50                  55

Glu Pro Gly Ala Lys Ser Met Val Arg Leu Ser Thr Thr Pro Asp Ile
 60             65                  70                      75

Ser Lys Leu Pro Gln Asp Arg Glu Ser Leu Phe Tyr Phe Asn Leu Arg
            80                  85                  90

Glu Ile Pro Pro Arg Ser Glu Lys Ala Asn Val Leu Gln Ile Ala Leu
            95                  100                 105

Gln Thr Lys Ile Lys Leu Phe Tyr Arg Pro Ala Ala Ile Lys Thr Arg
            110                 115                 120

Pro Asn Glu Val Trp Gln Asp Gln Leu Ile Leu Asn Lys Val Ser Gly
            125                 130                 135

Gly Tyr Arg Ile Glu Asn Pro Thr Pro Tyr Tyr Val Thr Val Ile Gly
140             145                 150                     155

Leu Gly Gly Ser Glu Lys Gln Ala Glu Glu Gly Glu Phe Glu Thr Val
            160                 165                 170

Met Leu Ser Pro Arg Ser Glu Gln Thr Val Lys Ser Ala Asn Tyr Asn
            175                 180                 185

Thr Pro Tyr Leu Ser Tyr Ile Asn Asp Tyr Gly Gly Arg Pro Val Leu
            190                 195                 200

Ser Phe Ile Cys Asn Gly Ser Arg Cys Ser Val Lys Lys Glu Lys
            205                 210                 215
```

(2) INFORMATION FOR SEQ ID NO: 3:

(i) SEQUENCE CHARACTERISTICS:

(A) LENGTH: 30 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

GTCAAACACC GCCGGAACTC GTCCAGGCGA                                        30

(2) INFORMATION FOR SEQ ID NO: 4:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 4:

CGGGCGATAA AAAAGAGCTA TTTTGGTCTG                                        30

(2) INFORMATION FOR SEQ ID NO: 5:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 5:

GCGATAAAAA AGCATTATTT TCCTCTG                                           27

(2) INFORMATION FOR SEQ ID NO: 6:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 6:

Gly Lys Arg Lys Pro Gly Glu Leu Ser Gly Ser Met Thr Met Val Leu
1               5                  10                  15

Ser Phe Pro (2) INFORMATION FOR SEQ ID NO: 7:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 7:

Lys Pro Gly Glu Leu Ser Gly Ser Met Thr Met Val Leu Ser Phe Pro
1               5                  10                  15

(2) INFORMATION FOR SEQ ID NO: 8:

(i) SEQUENCE CHARACTERISTICS:

```
          (A) LENGTH: 11 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 8:

Ser Gly Ser Met Thr Met Val Leu Ser Phe Pro
1               5                   10

(2) INFORMATION FOR SEQ ID NO: 9:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 9:

Thr Met Val Leu Ser Phe Pro
1               5

(2) INFORMATION FOR SEQ ID NO: 10:

(i) SEQUENCE CHARACTERISTICS:
          (A) LENGTH: 19 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 10:

Gly Lys Arg Lys Pro Val Glu Leu Ser Gly Ser Met Thr Met Val Leu
1               5                   10                  15

Ser Ser Pro (2) INFORMATION FOR SEQ ID NO: 11:

(i) SEQUENCE CHARACTERISTICS:
          (A) LENGTH: 19 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 11:

Gly Lys Arg Lys Pro Gly Glu Leu Ser Gly Ser Met Thr Met Val Leu
1               5                   10                  15

Ser Phe Pro (2) INFORMATION FOR SEQ ID NO: 12:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 12:

Glu Glu Gly Lys Arg Lys Pro Gly Glu Leu Ser Gly Ser Met Thr Met
1               5                   10                  15
```

```
Val Leu Ser Phe
         20

(2) INFORMATION FOR SEQ ID NO: 13:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Gln Asn Leu Ile Ala Gly Pro Phe Ser Ala Thr Ala Thr Leu Val Ala
1               5                  10                  15

Ser Tyr Ser (2) INFORMATION FOR SEQ ID NO: 14:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Lys Lys Leu Glu Ala Gly Asn Tyr Phe Ala Val Leu Gly Phe Arg Val
1               5                  10                  15

Asp Tyr Glu (2) INFORMATION FOR SEQ ID NO: 15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Lys Ser Val Val Pro Gly Asp Tyr Glu Ala Thr Ala Thr Phe Glu Leu
1               5                  10                  15

Thr Tyr Arg (2) INFORMATION FOR SEQ ID NO: 16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Gly Ile Leu Asn Gly Gly Asp Phe Gln Thr Thr Ala Ser Met Ala Met
1               5                  10                  15

Ile Tyr Asn (2) INFORMATION FOR SEQ ID NO: 17:
```

```
    (i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Tyr Ala Leu Ala Pro Asn Ala Val Ile Pro Thr Ser Leu Ala Leu Leu
1               5                   10                  15

(2) INFORMATION FOR SEQ ID NO: 18:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Lys Ser Val Val Pro Gly Asp Tyr Glu Ala Thr Ala Thr Phe Glu Leu
1               5                   10                  15

Thr Tyr Arg (2) INFORMATION FOR SEQ ID NO: 19:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Leu Pro Ala Thr Asn Thr Leu Met Leu Ser Phe Asp Asn Val Gly Gly
1               5                   10                  15

(2) INFORMATION FOR SEQ ID NO: 20:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Asp Gln Ile Lys Gln Leu Pro Ala Thr Asn Thr Leu Met Leu Ser Phe
1               5                   10                  15

(2) INFORMATION FOR SEQ ID NO: 21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Tyr Lys Met Pro Tyr Asp Gln Ile Lys Gln Leu Pro Ala Thr Asn Thr
1               5                   10                  15
```

(2) INFORMATION FOR SEQ ID NO: 22:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

```
Gln His His Tyr Tyr Asp Leu Trp Gln Asp His Tyr Lys Met Pro Tyr
1               5                   10                  15
```

(2) INFORMATION FOR SEQ ID NO: 23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

```
CCCCCCTGCA GATCAGATTA AGCAGCTACC TGC                           33
```

(2) INFORMATION FOR SEQ ID NO: 24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
CCCCTGCAGT AAAAATATCT CTGCTCAGAA ATAC                          34
```

(2) INFORMATION FOR SEQ ID NO: 25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

```
CCATCGATGA ACAGCCAGTC AGATAATC                                 28
```

(2) INFORMATION FOR SEQ ID NO: 26:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

```
GGAAAGAGAA AACCCGGGGA GCTATCTGGT TCTATGACTA TGGTTCTGAG TTTCCCCTGA    60
T                                                                   61
```

```
(2) INFORMATION FOR SEQ ID NO: 27:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

CGATCAGGGG AAACTCAGAA CCATAGTCAT AGAACCAGAT AGCTCCCCGG GTTTTCTCTT      60

TCCTGCA                                                               67
```

TREATMENT OR PROPHYLAXIS OF DISEASES CAUSED BY PILUS-FORMING BACTERIA

This application is a divisional of application Ser. No. 08/640,877, filed Oct. 10, 1996, now U.S. Pat. No. 6,420,127, which is a divisional of application Ser. No. PCT/US94/13455, filed Nov. 18, 1994, which is a continuation in part of application Ser. No. 08/154,035, filed Nov. 18,1993, now abandoned.

This invention was made with US government support under grant number R01AI29549 (S.J.H.) and training grant AI07172, both awarded by NIH. The US government has certain rights in the invention.

The patent or application file contains at least one drawing executed in color. Copies of this patent or patent application publication with color drawing(s) will be provided by the Office upon request and payment of the necessary fee.

FIELD OF THE INVENTION

The present invention relates to methods for the treatment and/or prophylaxis of diseases caused by tissue-adhering pilus-forming bacteria by interaction with the binding between pilus subunits and periplasmic chaperones. The invention further relates to methods for identifying/designing substances capable of interacting with periplasmic chaperones and methods for identifying binding sites in periplasmic chaperones. Finally, the invention relates to novel substances capable of interacting with periplasmic chaperones as well as pharmaceutical preparations comprising substances capable of interacting with periplasmic chaperones.

BACKGROUND OF THE INVENTION

Pathogenic Gram-negative bacteria cause a number of pathological conditions such as bacteraemia, bacteria-related diarrhoea, meningitis and (very commonly) urinary tract infections, i.a. pyelonephritis, cystitis, urethritis etc.

Urinary tract infections are one of the major causes of morbidity in females. Despite the overall importance of urinary tract infections in women, there have been few efforts to apply novel strategies in order to treat and/or prevent these diseases. Commonly, conventional antibiotics are used to treat these infections, such as treatment with penicillins, cephalosporins, aminoglycosides, sulfonamides and tetracyclines; in the special case of urinary tract infections, urinary antiseptics such as nitrofurantoin and nalidixic acid are employed, too. However, emerging antibiotic resistance will in the future hamper the ability to successfully treat urinary tract infections. Multiple antibiotic resistance among these uropathogens is increasing. It has been estimated that the annual cost for evaluation and treatment of women with urinary tract infections exceeds one billion dollars. In addition, approximately one-fourth of the yearly 4 billion dollar cost attributed to nosocomial infections is a consequence of urinary tract infections. Among the causative agents of urinary tract infections, *Escherichia coli* clearly predominates among Gram-negative bacteria.

Pathogenic gram negative bacteria, notably *Escherichia coli, Haemophilus influenzae, Salmonella enteriditis, Salmonella typhimurium, Bordetella pertussis, Yersinia pestis, Yersinia enterocolitica, Helicobacter pylori,* and *Klebsiella pneumoniae* owe part of their infectability to their ability to adhere to various epithelial tissues. Thus, e.g. *E. coli* adhere to the epithelial cells in the upper urinary tract in spite of the flushing effect of unidirectional flow of urine from the kidneys.

As indicated above, the above mentioned bacteria are involved in a variety of diseases: Urinary tract infections (*E. coli*), acute diarrhoea (*E. coli, Y. enterocolitica* and *Salmonella* spp), meningitis (*E. coli* and *H. influenzae*), whooping cough (*B. pertussis*), plague (*Y. pestis*), pneumonia and other respiratory tract infections (*K. pneumoniae, H. influenzae*) and peptic ulcer (*H. pylori*).

The initiation and persistence of many bacterial infections such as those described above is thought to require the presentation of adhesins on the surface of the microbe in accessible configurations which promote binding events that dictate whether extracellular colonization, internalization or other cellular responses will occur. Adhesins are often components of the long, thin, filamentous, heteropolymeric protein appendages known as pili, fimbriae, or fibrillae (these three terms will be used interchangeably herein). The bacterial attachment event is often the result of a stereochemical fit between an adhesin frequently located at the pilus tip and specific receptor architectures on host cells, often comprising carbohydrate structures in membrane associated glycoconjugates.

Uropathogenic strains of *E. coli* express P and type 1 pili that bind to receptors present in uroepithelial cells. The adhesin present at the tip of the P pilus, PapG (pilus associated polypeptide G), binds to the Galα(1–4)Gal moiety present in the globoseries of glycolipids, while the type 1 adhesin, FimH, binds D-mannose present in glycolipids and glycoproteins. Adhesive P pili are virulence determinants associated with pyelonephritic strains of *E. coli* whereas type 1 pili appear to be more common in *E. coli* causing cystitis. At least eleven genes are involved in the biosynthesis and expression of functional P pili; the DNA sequence of the entire pap gene cluster has been determined. P pili are composite heteropolymeric fibers consisting of flexible adhesive fibrillae joined end to end to pilus rods. The pilus rod is composed of repeating PapA protein subunits arranged in a right handed helical cylinder. Tip fibrillae which extend from the distal ends of each pilus rod were found to be composed mostly of repeating subunits of PapE arranged in an open helical conformation. The PapG adhesin was localized to the distal ends of the tip fibrillae, a location which is assumed to maximize its ability to recognize glycolipid receptors on eukaryotic cells. Two minor pilus components, PapF and PapK, are specialized adaptor proteins found in the tip fibrillum. PapF links the adhesin moiety to the fibrillum while PapK joins the fibrillum to the pilus rod. The composite architecture of the P pilus fiber reveals the strategy used by uropathogenic *E. coli* to present the PapG adhesin to eukaryotic receptors. The rigid PapA rod extends the adhesin away from interference caused by LPS and other components at the bacterial cell surface while the flexible fibrillum allows PapG steric freedom to recognize and bind to the digalactoside moiety on the uroepithelium. With a few exceptions, the structural organization of type 1 pili is very similar to that described for P pili. In type 1 pili, the mannose binding fibrillar tip adhesin is known as FimH.

The assembly of virulence-associated pili in Gram-negative pathogens requires the function of periplasmic chaperones. Molecular chaperones are vital components of all living cells, prokaryotic and eukaryotic. Chaperones serve a variety of cellular functions including folding, import and export of proteins in various cellular compartments (Gething and Sambrook, 1992). Thus, a periplasmic chaperone is a molecular chaperone which exerts its action in the periplasmic space in bacteria.

PapD and FimC are the periplasmic chaperones that mediate the assembly of P and type 1 pili, respectively. Detailed structural analyses have revealed that PapD is the prototype member of a conserved family of periplasmic chaperones in Gram-negative bacteria. These chaperones have a function which is part of a general strategy used by bacteria to cap and partition interactive subunits imported into the periplasmic space into assembly competent complexes, making non-productive interactions unfavourable. Determination of the three-dimensional structure of PapD revealed that it consists of two immunoglobulin-like domains oriented in a boomerang shape such that a cleft is formed. PapD binds to each of the pilus subunit types as they emerge from the cytoplasmic membrane and escorts them in assembly-competent, native-like conformations from the cytoplasmic membrane to outer membrane assembly sites comprised of PapC. PapC has been termed a molecular usher since it receives chaperone-subunit complexes and incorporates, or ushers, the subunits from the chaperone complex into the growing pilus in a defined order.

With the exception of the type IV class of pili, all other genetically well characterized pilus systems in Gram-negative prokaryotes contain a gene analogous to PapD (Normark et al., 1986; Hultgren et al. 1991); cf. also table A. FanE, faeE, sfaE, ClpE and f17-D have been sequenced (Lintermans, 1990; Schmoll et al., 1990; Bertin Y et al., 1993; Bakker et al., 1991) and encode pilus chaperones required for the assembly of K99, K88, S and F17 pili, respectively, in *E. coli*. The assembly of *Klebsiella pneumoniae* type 3 pili and Haemophilus influenzae type b pili requires the mrkb and hifB gene products, respectively (Gerlach et al., 1989,; Allen et al., 1991). The structure-function relationships of all of these chaperones have been analyzed using their amino acid sequences and information from the crystal structure of PapD (Anders Holmgren et al., 1992). The results have provided insight into the molecular intricacies that have been evolutionarily conserved in this class of proteins and suggested significant structural similarities to immunoglobulins.

PapD is thus the prototype member of a family of periplasmic chaperone proteins which are necessary for the correct supramolecular assembly of bacterial pili. Chaperones such as PapD in *E. coli* are required to bind the above-mentioned pilus proteins imported into the periplasmic space, partition them into assembly competent complexes and prevent non-productive aggregation of the subunits in the periplasm (Dodson et al., 1993).

In the absence of an interaction with the chaperone, pilus subunits aggregate and are proteolytically degraded (Kuehn, Normark, and Hultgren, 1991). It has recently been discovered (Strauch, Johnson and Beckwith, 1989) that the DegP protease is greatly responsible for the degradation of pilin subunits in the absence of the chaperone. This discovery has allowed the elucidation of the fate of pilus subunits expressed in the presence or absence of the chaperone using monospecific antisera in western blots of cytoplasmic membrane, outer membrane and periplasmic proteins prepared according to standard procedures. Expression of papG or papA in the degP41 strain (a DegP⁻ *E. coli* strain) in the absence of a chaperone was toxic to the bacteria due to the accumulation of these proteins in the cytoplasmic membrane suggesting that the chaperone was required for subunit import into the periplasmic space. The severity of the growth defect was related to the level of expression of the pilin subunit, and was generally more dramatic with PapG than PapA. Co-expression of PapD under the control of the inducible arabinose promoter rescued the growth defect associated with subunit expression in the degP41 strain and allowed PapG to be imported into the periplasm.

Up to this time, little has been elucidated about the molecular recognition motifs or chaperones. Cytoplasmic chaperones such as SecB, GroEL and DNaK bind to a diverse group of unfolded target proteins in a sequence independent manner (Gething and Sambrook, 1992). Recently, it has been suggested that DNaK binds mainly via the target's peptide backbone (Landry et al., 1992) and that GroEL may rely more on side-chain hydrophobicity and the ability of the target sequence to form an amphipathic α-helix (Landiy and Gierasch, 1991). PapD differs, however, in that it seems to bind its target proteins in folded conformations (Kuehn et al., 1991).

The three-dimensional structure of PapD has previously been solved (Holmgren and Brändén, 1989). This has shown PapD to consist of two globular domains positioned such that the overall shape of the molecule resembles a boomerang with a cleft between the two domains. Each domain is a β-barrel structure formed by two antiparallel β-pleated sheets, packed tightly together to form a hydrophobic core, with a topology similar to that of an immunoglobulin fold. The N-terminal domain of PapD most resembles an Ig variable domain whilst the C-terminal domain of PapD resembles CD4 (Wang et al., 1990, Ryu et al., 1990) and the human growth hormone receptor (de Vos et al., 1992).

A structural alignment between PapD and several periplasmic chaperones predicted to have a similar immunoglobulin-like structure has identified invariant, highly conserved and variable residues within this protein family (Holmgren et al., 1992). Most conserved residues seem to participate in maintaining the overall structure and orientation of the domains towards one another. However, two conserved residues, Arg-8 and Lys-112 are surface exposed and oriented towards the cleft between the domains. Site-directed mutagenesis of the Arg-8 amino acid has shown that it form at least part of the pilus subunit binding pocket (Holmgren et al., 1992; Kuehn et al., 1993).

From a sequence analysis of a number of the above-mentioned pilus subunit proteins, it has been observed that they possess a number of common features including homologies at the C termini (see also example 2). It is thought that these similarities in sequence may be responsible for some function common to all the pilus proteins, such as binding to their periplasmic chaperone. Indeed, the C-terminal region of the P-pili adhesin PapG has already been shown to be important in the in vivo binding to PapD (Hultgren et al., 1989). Table A lists 16 periplasmic proteins, all involved in assembly of cell surface structures in pathogenic bacteria and all with significant homology with PapD.

TABLE A

| Organism | Chaperone | Structure Assembled | Reference |
| --- | --- | --- | --- |
| *E. coli* | PapD | P pili | Lund et al., 1987 |
| *E. coli** | FimC | Type 1 pili | Klemm et al., 1992 |
| *E. coli* | Sfae | S pili | Schmoll et al., 1990 |
| *E. coli* | FaeE | K88 pili | Bakker et al., 1991 |
| *E. coli* | FanE | K99 pili | Bakker et al., 1991 |
| *E. coli* | CS3-1 | CS3 pili | Jalajakumari et al., 1989 |
| *E. coli* | F17D | F17 pili | Lintermans et al., 1990 |

TABLE A-continued

| Organism | Chaperone | Structure Assembled | Reference |
|---|---|---|---|
| E. coli | ClpE | CS31 A | Bertin et al., 1993 |
| E. coli | EcpD | not identified | Raina et al., 1993 |
| E. coli | CssC | Antigen CS6 | |
| E. coli | NfaE | Nonfimbrial adhesin 1 | |
| E. coli | AggD | Aggregative Adherence Fimbria 1 | |
| K. pneumoniae | MrkB | Type 3 pili | Allen et al., 1991 |
| B. pertussis | FimB | Type 2 & 3 pili | Locht et al., 1992; Willems et al. 1992 |
| S. enteriditis | SefB | unknown pili | Clouthier et al., 1993 |
| S. typhimurium | PefD | PEF | |
| H. influenzae | HifB | unknown pili | Smith et al., 1993 |
| Y. enterocolitica | MyfB | Myf fibrillae | Iriarte et al., 1993 |
| Y. pestis | PsaB | pH6 antigen | Lindler et al., 1992 |
| Y. pestis | Caf1M | F1 envelope antigen | Galyov et al., 1991 |
| P. mirabilis | MrpD | MR/P Fimbriae | |
| ? | YehC | ? | |

*This chaperone is present in all *Enterobacteriaceae*, since all members of this family produce type 1 pili.

In summary, the three-dimensional structure of PapD as well as the function of PapD and other periplasmic chaperones are known, whereas the exact motif of binding between PapD and the pilus subunits has been unknown until now.

DISCLOSURE OF THE INVENTION

According to the present invention, it has been realized that the above-mentioned characteristics of PapD and other related chaperones make them interesting targets for drugs designed primarily to reduce the pathogenicity of bacteria which adhere by means of pili; for example, a drug which blocks the binding between a chaperone and the pilus-subunits (thereby interfering with the assembly of the intact pilus) will interfere with the formation of intact pili, thereby reducing bacterial capacity to adhere to host epithelium.

In order to design such a drug it is of great value that the motif of binding between the chaperone and the pilus protein(s) is known in detail, in order to develop the method to effectively identify compounds capable of blocking this binding.

An aspect of the current invention relates to a method for the treatment and/or prophylaxis of diseases caused by tissue-adhering pilus-forming bacteria, comprising preventing, inhibiting or enhancing binding between at least one type of pilus subunit and at least one type of molecular chaperone in the pilus-forming bacteria, which molecular chaperone binds pilus subunits during transport of these pilus subunits through the periplasmic space and/or during the process of assembly of the intact pilus.

As used herein, the term "pilus", "fimbria", or "fibrilla", relates to fibrillar heteropolymeric structures embedded in the outer membrane of many tissue-adhering pathogenic bacteria, notably the pathogenic gram negative bacteria. In the present specification the terms pilus, fibrillum and fimbria will be used interchangeably. A pilus is, as explained above, composed of a number of "pilus subunits", which constitute distinct functional parts of the intact pilus. A very important pilus subunit is the "adhesin", the pilus subunit which is responsible for the tissue-binding capacity of the bacterium.

By the term "molecular chaperone" is meant a molecule which in living cells has the responsibility of binding to peptides in order to mature the peptides in a number of ways. Many molecular chaperones are involved in the process of folding of peptides into their native conformation whereas other molecular chaperones are involved in the process of export out of or import into the cell of peptides. Specialized molecular chaperones are "periplasmic chaperones", which are bacterial molecular chaperones exerting their main actions in the "periplasmic space" (the space between the inner and outer bacterial membrane). Periplasmic chaperones are involved in the process of correct assembly of intact pili. When used herein, the simple term "chaperone" designates a molecular, periplasmic chaperone if nothing else is indicated.

When using the phrase "one type of" is meant that the pilus subunit or the chaperone in question is of one distinct species. However, especially the fact that there is extensive homology between different species of periplasmic molecular chaperones renders it likely that the interference with one type of chaperone using e.g. a compound will make it possible to also use the compound in interference with other chaperones.

The phrase "preventing, inhibiting or enhancing binding between pilus subunits and at least one molecular chaperone in the pilus-forming bacteria" indicates that the normal interaction between a chaperone and its natural ligand, i.e. the pilus subunit, is being affected either by being completely or substantially completely prevented, or by being inhibited, or expressed in another manner, reduced to a such an extent that the binding of pilus subunits to the chaperone is measurably lower than is the case when the chaperone is interacting with the pilus subunit at conditions which are substantially identical (with regard to pH, concentration of ions and other molecules) to the native conditions in the periplasmic space. Similarly, the enhancement of binding between the chaperone and the pilus subunit should be such that the binding of pilus subunits to the chaperone is measurably higher than is the case when the chaperone is interacting with the pilus subunit at conditions which are substantially identical (with regard to pH, concentrations of ions and other molecules) to the native conditions in the periplasmic space. Measurement of the degree of binding can be determined in vitro by methods known to the person skilled in the art (microcalorimetry, radioimmunoassays, enzyme based immuno assays, etc).

It should, on the basis of the above, be clear that prevention or inhibition of the normal interaction between a pilus subunit and a chaperone should have a substantially limiting effect on pilus assembly. However, an enhancement of the binding between pilus subunits and chaperones may also prove to be devastating to a bacterium. As will appear from example 2, different pilus subunits bind to PapD with different affinities and affecting this narrowly balanced system may also cause a limitation on the rate and efficiency of pilus assembly.

It is believed that even modest changes in the binding between pilus subunits and chaperones can have dramatic impact on the efficiency of pilus assembly, and thus on the ability of the bacteria to adhere. For example, if the change in the binding between a chaperone and one pilus subunit is such that the normal order of affinities between the chaperones and the pilus subunits which normally bind thereto is altered, then the normal assembly of the pilus should be disturbed, since the order of assembly of the pilus may be dependent i.a. on the affinities between the pilus subunits and the chaperone: The pilus subunits with the highest affinities to the chaperone may be incorporated before other pilus subunits with lesser affinities.

Thus, prevention, inhibition or enhancement of binding between pilus subunits and a periplasmic molecular chaperone have the effect of impairing pilus assembly, whereby the infectivity of the microorganism normally expressing the pili is reduced.

Prevention, inhibition or enhancement of the binding between pilus subunits can be accomplished in a number of ways. A preferred method according to the invention of treatment and/or prophylaxis of diseases caused by tissue-adhering pilus-forming bacteria is to administer an effective amount of a substance to a subject in need thereof, the substance being capable of interacting with at least one type of molecular chaperone which binds pilus subunits during transport of these pilus subunits through the periplasmic space and/or during the process of assembly of the intact pilus, in such a manner that binding of pilus subunits to the molecular chaperone is prevented, inhibited or enhanced.

The substance can be any compound which has one of the above mentioned effects on the interaction between chaperones and pilus subunits and thereby on the assembly of the pilus. Especially interesting substances are those which are likely to interact with the pilus subunit binding part of the chaperone, but interaction with other sites in the chaperones may also cause prevention, inhibition or enhancement of the binding between pilus subunits and the chaperone. This can be an effect of direct steric blocking of the normal binding between the subunit and the chaperone, but it may also be an effect of a conformational change in the chaperone. A method of identifying substances to be used in the method of the invention is disclosed below.

The interaction between the substance and the chaperone may be a covalent as well as a non-covalent binding to the chaperone by the substance.

By the term "subject in need thereof" is in the present context meant a subject, which can be any animal, including a human being, who is infected with, or is likely to be infected with, tissue-adhering pilus-forming bacteria which are believed to be pathogenic.

By the term "an effective amount" is meant an amount of the substance in question which will in a majority of patients have either the effect that the disease caused by the pathogenic bacteria is cured or, if the substance has been given prophylactically, the effect that the disease is prevented from manifesting itself. The term "an effective amount" also implies that the substance is given in an amount which only causes mild or no adverse effects in the subject to whom it has been administered, or that the adverse effects may be tolerated from a medical and pharmaceutical point of view in the light of the severity of the disease for which the substance has been given.

The route of administration of the substance could be any conventional route of administration, i.e. oral, intraveneous, intramuscular, intradermal, subcutaneous etc. The oral route is preferred.

The dosage of such a substance is expected to be the dosage which is normally employed when administering antibacterial drugs to patients or animals, i.e. 1 $\mu$g–1000 $\mu$g per kilogram of body weight per day. The dosage will depend partly on the route of administration of the substance. If the oral route is employed, the absorption of the substance will be an important factor. A low absorption will have the effect that in the gastro-intestinal tract higher concentrations, and thus higher dosages, will be necessary. Also, the dosage of such a substance when treating infections of the central nervous system (CNS) will be dependent on the permeability of the blood-brain barrier for the substance. As is well-known in the treatment of bacterial meningitis with penicillin, very high dosages are necessary in order to obtain effective concentrations in the CNS.

It will be understood that the appropriate dosage of the substance should suitably be assessed by performing animal model tests, wherein the effective dose level (e.g. $ED_{50}$) and the toxic dose level (e.g. TD50) as well as the lethal dose level (e.g. $LD_{50}$ or $LD_{10}$) are established in suitable and acceptable animal models. Further, if a substance has proven efficient in such animal tests, controlled clinical trials should be performed. Needless to state that such clinical trials should be performed according to the standards of Good Clinical Practice.

Although the preferred way of preventing, inhibiting or enhancing the binding between pilus subunits and chaperones is to administer a substance with the above mentioned effects on the chaperone, other ways are possible. For instance, substances interacting with one type of pilus subunit could also have the effects described above, and for the same reasons. However, as the interaction with the chaperone is likely to exert effects on the assembly into the pilus of most, if not all, pilus subunits constituting the intact pilus, it is expected that the interaction with the chaperone will be the most efficient in terms of hampering bacterial infectivity.

As will appear from the examples below, most of the data on binding between chaperones and pilus subunits have been obtained by studying the interaction between the PapD chaperone from *E. coli*. However, since many tissue adhering bacteria have been found to express pili which share substantial homologies in their C-terminal part, and since substantial homologies have been demonstrated between the various periplasmic chaperones which until now have been isolated (see table A), it is justified to assume that some substances and classes of substances will be capable of interacting with the majority of existing periplasmic chaperones and thus be useful in the treatment and/or prophylaxis of diseases caused by the bacteria harbouring these chaperones when the substance is administered to patients infected with the bacteria.

Thus, the method of the invention for the treatment and/or prophylaxis is especially intended to be used in patients which are infected by bacteria selected from the group consisting of *Haemophilus* spp, *Helicobacter* spp, *Pseudomonas aeruginosa*, *Mycoplasma* spp, and all members of the *Enterobacteriacieae* family, including *Escherichia* spp, *Salmonella* spp, *Bordetella* spp, *Yersinia* spp, *Proteus* spp and *Klebsiella* spp. In this connection, especially the bacteria selected from the group consisting of *E. coli, Y. pestis, Y. enterocolitica, B. pertussis, K. pneumoniae, S. typhimurium, S. typhi, S. paratyphii, Helicobacter pylori, Proteus mirabilis* and *Haemophilus influenzae* are regarded as infectants which cause infections which can be treated and/prevented by the use of the method according to the invention.

Accordingly, in important aspects of the invention, the binding of a pilus subunit to a chaperone selected from the group consisting of PapD, FimC, SfaE, FaeE, FanE, Cs3-1, F17D, ClpE, EcpD, Mrkb, FimB, SefB, HifB, MyfB, PsaB, PefD, YehC, MrpD, CssC, NfaE, AggD, and Caf1M is prevented, inhibited or enhanced. It is especially preferred that the binding of PapD to at least one pilus subunit is affected.

As stated above, in a preferred embodiment of the invention, the prevention, inhibition or enhancement of the binding is accomplished by interacting with, in the molecular chaperone, a binding site which is normally involved in binding to pilus subunits during transport of these pilus subunits through the periplasmic space and/or during the process of pilus assembly.

As mentioned, in connection with the present invention, the binding motif between PapD and a peptide which constitute the 19 amino acids of the C-terminal of PapG (G1'-19'), a pilus subunit, has been determined. As is described in detail herein, other chaperones share substantial homologies with PapD in this binding site. Thus, such a binding site is of great interest as a target for drugs which are intended to interact with periplasmic chaperones. Therefore, in a preferred embodiment of the above described methods of the invention, the binding site which is affected is one which binds G1'-19'.

Thus, an important aspect of the invention is a method as described above, wherein the binding site is a binding site to which the carboxyl terminal part of a pilus subunit is capable of binding, and which comprises site points substantially identical to the invariant residues Arg-8 and Lys-112 in PapD, and a polypeptide fragment which is capable of interacting with a β-strand of the carboxyl terminal part of the pilus subunit thereby stabilizing the binding of said subunit at the Arg-8 and Lys-112 site points of the binding site. An especially preferred aspect of the invention is a method as described above, where the binding side is the G-protein binding site of PapD as described herein.

The term "site-point" refers to a chemical group with well defined physical/chemical characteristics such as size, charge, hydrophobicity/hydrophilicity, polarity, direction of hydrogen bonds as well as a 3-dimensional position (distance and angle) relative to other such chemical groups. Thus, site-points which are "substantially identical" to Arg-8 and Lys-112, are chemical groups which substantially share the same well-defined physical/chemical characteristics as these two amino acids.

The term "invariant residues" refer to amino acid residues which can be found in a number of proteins without there being any variation with regard to the precise type of the amino acid and without there being any substantial variation in their function in the proteins. The presence of invariant residues in a large number of related proteins normally is an indication of the biological importance of such residues, since mutations lacking these residues apparently lacks the function of the intact protein, too. As described herein, it has been found that all periplasmic molecular chaperones share the amino acid residues which are equivalent to Arg-8 and Lys-112. It is believed that these two residues therefore are of considerable importance to pilus-forming bacteria.

"A polypeptide fragment capable of interacting with a β-strand of the carboxyl terminal part of a pilus subunit" indicates that part of the chaperone (which is also a part of the binding site) is capable of interacting with a β-strand of the pilus subunit. This interaction serves as a stabilizing factor in the binding between the pilus subunit and the chaperone and is considered a very important part of the total motif of binding between the chaperone and the pilus subunit. Further, it has recently been rendered probable by the inventors that the β-strand serves as a template for the correct folding of the pilus subunit (cf. example 10).

As explained herein, the C-terminal part of many, if not all, known pilus subunits, share substantial homologies, which is another indication of the importance of the 3-dimensional structure of the pilus subunit as well as of the chaperone in order for the binding to take place and be stable.

As appears from the examples, another binding site residing in domain 2 of PapD has been identified. This binding site interacts with fusion protein MBP-G1'-140' as well as with a short peptide constituted of the C-terminal amino acid residues 125' to 140' of PapG. Thus, also this binding site is of great interest as a target for drugs which are intended to interact with periplasmic chaperones. Therefore, a preferred embodiment of the above described methods of the invention is a method wherein the binding site which is affected is one which binds either of the two above-described peptides.

It will be understood that the above-described methods comprising administration of substances in treating and/or preventing diseases are dependent on the identification or de novo design of substances which are capable of exerting effects which will lead to prevention, inhibition or enhancement of the interaction between pilus subunits and periplasmic molecular chaperones. It is further important that these substances will have a high chance of being therapeutically active.

Thus, an aspect of the invention relates to a method for identifying a potentially therapeutically useful substance capable of interacting with a periplasmic molecular chaperone, thereby preventing, inhibiting or enhancing the interaction between a periplasmic molecular chaperone and a pilus subunit, the method comprising at least one of the following steps:

1) testing a candidate substance in an assay in which the possible prevention, inhibition or enhancement by the substance of the interaction between the periplasmic molecular chaperone and the pilus subunit is determined by
   a) adding the substance to a system comprising the periplasmic molecular chaperone or an analogue thereof in an immobilized form and the pilus subunit or an equivalent thereof in a solubilized form and determining the change in binding between the pilus subunit or equivalent thereof and the periplasmic molecular chaperone or analogue thereof caused by the addition of the substance, or
   b) adding the substance to a system comprising the pilus subunit or an equivalent thereof in an immobilized form and the periplasmic molecular chaperone or an analogue thereof in a solubilized form and determining the change in binding between the pilus subunit or equivalent thereof and the periplasmic molecular chaperone or analogue thereof caused by the addition of the substance, or
   c) adding the substance to a system comprising the pilus subunit or an equivalent thereof as well as the periplasmic molecular chaperone or an analogue thereof in solubilized form and determining the change in binding between the pilus subunit or equivalent thereof and the periplasmic molecular chaperone or analogue thereof caused by the addition of the substance, or
   d) adding the substance to a system comprising the pilus subunit or an equivalent thereof as well as the periplasmic molecular chaperone or an analogue thereof in solubilized form and measuring the change in binding energy caused by the addition of the substance, and identifying the substance as potentially therapeutically useful if a significant change in the binding energy between the pilus subunit or equivalent thereof and the periplasmic molecular chaperone or analogue thereof is observed, and identifying the substance as potentially therapeutically useful if a significant change in the binding or binding energy between the pilus subunit or equivalent thereof and the periplasmic molecular chaperone or analogue thereof is observed;

2) testing a candidate substance in an assay in which the possible prevention, inhibition or enhancement of the interaction between the periplasmic molecular chaperone and the pilus subunit is determined by adding the substance to a system comprising living tissue-adhering pilus-forming bacteria followed by determination of the growth rate of the bacteria, a reduction in growth rate compared to a corresponding system wherein the substance has not been added being indicative of prevention, inhibition or enhancement of the binding between the periplasmic molecular chaperone and the pilus subunit, or adding the substance to a system comprising living tissue-adhering pilus-forming bacteria followed by a determination of the tissue adhesion of the bacteria, a reduction in tissue adhesion compared to a corresponding system wherein the substance has not been added being indicative of prevention, inhibition or enhancement of the binding between the periplasmic molecular chaperone and the pilus subunit, and identifying the substance as potentially therapeutically useful if a reduction in growth rate or tissue adhesion is observed after the addition of the substance; and 3) administering, to an experimental animal, a substance which has been established in vitro to prevent, inhibit or enhance the interaction between a periplasmic molecular chaperone and a pilus subunit, the experimental animal being inoculated with tissue-adhering pilus-forming bacteria before, simultaneously with or after the administration of the substance, and electing as a substance suitably capable of interacting with a periplasmic molecular chaperone, a substance preventing and/or curing and/or alleviate disease caused by the bacteria.

By the term "an equivalent of a pilus subunit" is meant a compound which has been established to bind to the chaperone in a manner which is comparable to the way the pilus subunit binds to the chaperone, e.g. by the demonstration of the pilus subunit and the equivalent competing for the binding to the chaperone. Preferred equivalents of pilus subunits are G1'-19'WT, MBP-G1'-140' and G125'-140', which are all described in detail herein.

The term "an analogue of a chaperone" denotes any substance which has the ability of binding at least one pilus subunit m a manner which corresponds to the binding of said chaperone to a pilus subunit. Such an analogue of the chaperone can be a truncated form of the intact chaperone (e.g. one of the two domains of PapD) or it can be a modified form of the chaperone which may e.g. be coupled to a probe, marker or another moiety. Finally, the analogue of the chaperone can be an isolated, but partially or fully functional, binding site of the chaperone or a synthetic substance which mimics such as binding site.

The immobilization mentioned above may be simple non-covalent binding to an adhering surface or a host or receptor molecule such as an antibody, or covalent binding to a spacer molecule such as a polymer or a peptide.

In the above mentioned step 1a), the pilus subunit or the equivalent thereof being bound to the periplasmic molecular chaperone or an analogue thereof can be detected in a number of ways, e.g. by the pilus subunit or the equivalent thereof being labelled, or by means of a labelled ligand (such as an antibody) capable of reacting with the pilus subunit or the equivalent thereof, or by means of a refractive index based determination of the extend of binding, such as the Pharmacia BiaCore® assay.

Accordingly, in step 1b) the periplasmic molecular chaperone or the analogue thereof being bound to the pilus subunit or the equivalent thereof may be detected by the periplasmic molecular chaperone or the analogue thereof being labelled, by means of a labelled ligand (e.g. antibody) capable of reacting with the periplasmic molecular chaperone or the analogue thereof, or by means of a refractive index based determination of the extend of binding, such as the Pharmacia BiaCore® assay.

In step 1c) the periplasmic molecular chaperone or the analogue thereof being bound to the pilus subunit or the equivalent thereof may be detected by separation of pilus subunit/chaperon complexes (e.g. by ultracentrifugation, ultrafiltration, liquid chromatography, such as size exclusion chromatography, or electrophoresis). Described below is a method relying on the changes in fluorescence of a short PapG fragment when this fragment is bound to PapD. This method is a preferred assay in the method of the invention.

The determination of binding energy in step 1c) is preferably performed in a microcalorimetric system using the well-known technique of microcalorimetry.

The above-indicated steps serve 3 purposes. The types of assays in step 1) are intended to shed light over the ability of the candidate substance of interacting with the chaperone. In the instances wherein labelled substances, chaperones or antibodies are used, the label could be a radioactive label, a fluorescent or light absorbing label, an enzyme such as horse-radish peroxidase, a ligand such as biotin, or any other conventional labelling system known to the person skilled in the art. The detection of the labelled compound is then dependent on the choice of label: radioactivity may be measured in a liquid-scintillation counter, a gamma counter, or any other convenient detection system for radioactivity, enzyme-labels are detected by the presence or absence of a specific substrate for the enzyme (optical density assessment, chemical reactivity of the remaining substrate or of the product etc.), fluorescent labels may be detected by fluorescence microscopy or simple measurement of the fluorescent emission, light-absorbing labels may be detected by measurement of absorbtion of light of a characteristic wavelength, and biotin may be detected by its binding to streptavidin.

The separation of high molecular complexes by ultracentrifugation or ultrafiltration in 1) may be detected by one of the components of the complex being labelled as described above; it is thus possible to detect the ratio between bound and unbound pilus subunit/equivalent, but the detection step may also rely on the binding of antibodies to one of the components of the complex, and the subsequent detection of this antibody. Any conventional chromatographic technique may be employed (HPLC, FPLC, size exclusion, etc) The separation by electrophoresis may e.g. be performed by capillary electrophoresis.

The assays in step 2) all relate to the effects of the candidate substance on bacterial activity in vitro. The demonstration of a reduction in growth rate of the bacteria or a demonstration of reduced adherence to cells or synthetic surfaces in an assay of course cannot be contributed to the effect of interaction with chaperones only, but a demonstration of this kind should provide a good estimate of the potential therapeutical usefulness of such a substance.

The determination of growth rate may be performed by counting of colonies on solid agar plates striped with the bacteria, by counting bacterial density in liquid growth media ($OD_{600}$ determination), by measuring fluorescence of substances such as NAD(P)H, ATP, or amino acids, which are contained in the bacterial cells only, or by any other convenient detection system known to the person skilled in the art. The determination of adherence of the bacteria may be performed in a similar manner after the adhering bacteria have been isolated. A determination of adherence is preferably performed by measuring the ability of the bacteria to agglutinate red blood cells or receptor-coated latex beads, by measuring the bacterial adhesion to receptor-coated microtiter plates, or by measuring the bacterial adhesion to other synthetic surfaces.

In a preferred embodiment of the method described above, the living, tissue adhering pilus-forming bacteria are of a protease deficient strain, the protease being one which is at least partially responsible for the degradation of pilus subunits. One especially preferred type of strain is the degP41 strain of *E. coli*. As described herein, the degP41 strain lacks activity of the DegP protease which is responsible for degradation of pilus subunits in the *E. coli* when these are not rescued into periplasmic space by PapD, and degP41 strains are thus especially sensitive to changes in the efficiency of PapD, as the accumulation of pilus subunits is toxic to the cell. It is believed that equivalent proteases exist in other pilus expressing bacteria.

The animal study in step 3) is performed in order to demonstrate the potential therapeutic usefulness of the candidate substance in vivo. Further, as already mentioned above, such animal studies should also establish the a priori values regarding effective dosage and toxicity before the candidate substance finally is tested in human beings in controlled clinical trials. The animal studies should also provide information regarding the convenient formulation of the substance in a pharmaceutical preparation as well as the preferred route of administration, as it is possible to obtain, from the animal model, data for absorbtion of the substance as well as data for the metabolism and excretion of the substance. The experimental animal is preferably a mouse, a rat, a cat, a dog, a monkey, a horse, a cow, a pig, or a chicken.

The term "suitably capable of interacting with a molecular chaperone" is intended to indicate that a substance, apart from being capable of interacting with a molecular chaperone, also is capable of exerting effects in an in vivo system, i.e. that the substance in addition to its binding capability also exhibits compatibility with a biological system, i.a. a patient.

Although the above-indicated in vivo studies, especially the experiments in animal models, are the best indicators of the potential therapeutical usefulness of a substance in the prevention, inhibition, or enhancement of the binding between a chaperone and a pilus subunit, it should not be forgotten that the in vitro assays outlined above serve as important leads when developing compounds with a therapeutical potential. If one relied only on in vivo assays, it is very likely that compounds which in fact exhibit the desired effect on the chaperone/pilus subunit interaction would be screened out by the in vivo assays, because these compounds could lack e.g. the ability to penetrate biological membranes. When using the in vitro assays, a much greater chance of finding a lead compound is maintained.

The evaluation of the effect of a substance tested in the in vitro assays described herein (cf. in this connection especially the examples) depends on a number of factors. It will be understood by the skilled person that a small molecule could be added in rather high molar concentrations in order to exert an effect on the chaperone/pilus subunit interaction (and even then the small molecule may still be an interesting lead compound), whereas larger molecules may exert marked effects even in rather low molar concentrations. In general, when any in vitro assay described herein is regarded as having a positive result when testing a candidate substance (i.e. that the substance tested shows a "significant" effect), the following condition should be fulfilled: The compound should exert a significant effect on pilus subunit/chaperone interaction (or on an interaction in an equivalent system which correlates well to pilus subunit/chaperone interaction), the significant effect being one which with no doubt can be attributed to the interaction between the substance and the chaperone and which is not an unspecific interaction between the chaperone and the substance (due to e.g. radical changes in the physical and chemical environment when the substance is added). One way of excluding unspecific interactions as the reason for the exerted effect is to use at least one control which is a chemically comparable substance (with respect to molecular mass, charge/polarity and gross 3-dimensional conformation (globular, fibrillar etc.). If the control does not result in substantially the same effect in the assay as the substance, it can be concluded that the substance must be regarded as an assay positive substance.

The assays described in the examples are all good examples of assay types, which could serve as the test system in the above-described method of the invention. However, it is preferred that the method described in example 10 employing a fluorescence labelled variant of a pilus subunit is used in step 1c). This assay may shortly be described as follows:

adding the substance to a first system comprising the periplasmic molecular chaperone or an analogue thereof, subsequently adding a pilus subunit or an equivalent thereof which has been labelled with an environmentally sensitive fluorescent probe, determining the fluorescent emission at a particular wavelength which is indicative of the amount of binding between the periplasmic molecular chaperone or the analogue thereof and the pilus subunit or the equivalent thereof, and comparing the determined fluorescent emission to fluorescent emission determined in a corresponding second system containing substantially the same concentrations of the molecular chaperone or the analogue thereof and the pilus subunit or the equivalent thereof but substantially no substance, a significant difference in fluorescent emission between the first and second system being indicative of interaction between the periplasmic molecular chaperone or the analogue thereof and the substance.

The advantage of this assay is that it may be employed for quantitative determinations of the effect of the tested substance on the chaperone/pilus subunit system. By using this assay the inventors have e.g. determined the constant of binding between a PapG analogue and PapD. The quantitative determinations may be performed by performing the determination of fluorescent emission in the second system a plurality of times at varying molar ratios between the pilus subunit or the equivalent thereof and the periplasmic chaperone and the equivalent thereof, whereupon the constant of binding between the pilus subunit or equivalent thereof and the periplasmic molecular chaperone or analogue thereof is assessed from the determined fluorescent emission data. From the data obtained in this way it is also possible to determine the binding constant of the substance in a parallel manner, which will appear from claim 11.

It will be understood that the above-indicated method for identifying a potentially therapeutically useful substance is dependent on the actual presence of the substance. Normally, it is necessary to either purify or synthesize the candidate substance before it is subjected to the above-mentioned method. However, since many such candidate substances are likely to be tested before a substance which is suitably capable of interacting with a chaperone will be identified, it is of interest to identify such substances before they are subjected to the method above, thereby diminishing the resources spent on purification and/or synthesis steps.

Hence, the invention also relates to a method for identifying and/or designing a substance, X, capable of interacting with a chaperone, e.g. binding to the chaperone, with a predicted binding energy equal to or better than a predetermined threshold value, the method comprising 1) selecting a substance, A, which could potentially interact with a site in the chaperone, and providing a 3-dimensional structural representation thereof,
2) predicting the binding free energy between the substance A and the site in the chaperone,
3) if the predicted binding free energy between the substance A and the site in the chaperone is equal to or better than the predetermined threshold value, then identifying the substance A as the substance X,
4) if the predicted binding free energy between the substance A and the site in the chaperone is not equal to or better than a predetermined threshold value, then modifying the 3-dimensional structural representation and predicting the binding free energy between the thus modified substance, B, and the site in the chaperone, and
5) repeating step 4 until the predicted binding free energy determined between the resulting substance, X, and the site in the chaperone is equal to or better than the predetermined threshold value.

It is possible to expand the above-mentioned method with two further steps, wherein the actual binding free energy is determined, in order to establish that the experimental binding free energy also is better than the predetermined threshold value. By performing the following two steps 6) providing a sample of the chemical substance X and a sample of the chaperone and measuring the binding free energy between the chemical substance X and the chaperone (e.g. by microcalometry as mentioned above), and establishing that the measured binding free energy between the chemical substance X and the chaperone is equal to or better than the predetermined threshold value, and optionally
7) subjecting the substance X to the method mentioned above for identifying a substance suitably capable of interacting with a chaperone, in order to verify that the substance X is a potentially therapeutically useful substance capable of interacting with a chaperone, it is thus verified that the binding free energy between the candidate substance and the chaperone actually is better than the predetermined threshold value. Step 7) further establishes that the candidate substance stands good chances of being therapeutically useful.

The phrase "predicting the binding free energy" is meant to imply that the binding free energy is determined by calculation rather than by performing experimental work determining the actual binding free energy. One (theoretical) way of predicting binding free energy is by performing free energy perturbation (FEP) calculations on the interacting substances, but because of the vast amount of calculations such an approach would have as a result it is preferred that the empirical approximative method described below is employed.

The term "better than" is intended to mean that the binding free energy has a value which is higher than the binding free energy which has been chosen as the threshold value, meaning that the $\Delta G$ is numerically higher than the threshold value selected. Or in other words: The term is intended to mean that the binding between the substance and the chaperone is more favourable energetically than the situation were the substance and the chaperone are suspended independently in solution.

In order to predict the binding energy in the above-indicated method, according to the invention it is especially preferred to use the following method:

Assessing the average energy difference, $<\Delta V_{X-s}^{el}>$, defined as $<V_{X-s}^{el}>_B - <V_{X-s}^{el}>_A$, between the contribution from polar interactions to the potential energy between the chemical substance X and its surroundings (denoted s) in two states, one state (A) being where the chemical substance is surrounded by solvent, the other state (B) being where the chemical substance, bound to a periplasmic molecular chaperone or an analogue thereof, is surrounded by solvent, assessing the average energy difference, $<\Delta V_{X-s}^{vdw}>$, defined as $<V_{X-s}^{vdw}>_B - V_{X-s}^{vdw}>_A$, between the contribution from non-polar interactions to the potential energy between the chemical substance X and its surroundings (denoted s) in two states, one state (A) being where the chemical substance is surrounded by solvent, the other state (B) being where the chemical substance, bound to a periplasmic molecular chaperone or an analogue thereof, is surrounded by solvent, and calculating the absolute binding free energy as an adjusted combination of the two above-mentioned average energy differences.

In the mathematical equations herein, the symbol $<\,>$ means molecular dynamics average. The index X-s means compound-solvent (or compound-surrounding), the letter "X" denoting the chemical substance X. Normally the substance X will function as an inhibitor of the binding between the periplasmic chaperone and pilus subunits, but as discussed herein, it is also a possibility that the compound or drug will affect the chaperone in such a way that the binding between pilus subunits and the chaperone is enhanced. The superscript "el" designates the polar or electrostatic energy, while the superscript "vdw" indicates "van der Waals", another designation for the non-polar interactions. The symbol $\Delta$ indicates that the quantity in state A is subtracted from the quantity in state B.

In the present context the term "an analogue of a periplasmic molecular chaperone" should be understood, in a broad sense, any substance which mimics (with respect to binding characteristics) an interesting part of a periplasmic molecular chaperone (e.g. the pilus subunit binding part(s)), and the interaction of which with a chemical substance or a group or plurality of chemical substances, e.g. drug candidates, is to be studied. Thus, the analogue may simply be any other chemical compound regarded as capable of interacting with the chemical substance in a manner which mimics the binding between the chaperone and a pilus subunit in vivo, but most often the analogue will be a relatively large molecule, in other words a macromolecule such as a protein or an oligonucleotide, which is relatively large compared to the chemical substance; although the chemical substance interacting with the analogue, of course, in itself be a macromolecule. In the present context, the periplasmic molecular chaperone or analogue thereof is preferably the periplasmic chaperone or an analogue thereof which exhibits at least one interesting binding characteristic relevant for the assembly of pili.

The basis for the above-indicated approach for determining the binding free energy is explained in the following:

As a starting point is taken the linear response approximation for electrostatic forces which for polar solutions as a result yields quadratic free energy functions in response to the development of charges. This is, e.g., the familiar result from Marcus' theory of electron transfer reactions (Marcus, 1964). For a system with two states, A and B, given by two potential energy functions $V_A$ and $V_B$ one obtains, within the approximation of harmonic free energy functions of equal curvature, the relationship (see Lee et al., 1992 and references therein):

$$\lambda = <V_B - V_A>_A - \Delta G_{AB} = <V_A - V_B>_B + \Delta G_{AB} \quad (a)$$

where $\Delta G_{AB}$ is the free energy difference between B and A, $\lambda$ the corresponding reorganisation energy and $<>_i$ denotes an average evaluated near the minimum of the potential i. Thus, $$\Delta G_{AB} \cong \tfrac{1}{2}(<\Delta V>_A + <\Delta V>_B) \quad (b)$$

where $\Delta V$ now denotes the energy difference $V_B - V_A$. If the hydration of a single ion is considered, this can be shown to give $\Delta G_{sol}^{el} = \tfrac{1}{2} <V_{X\text{-}s}^{el}>$, i.e. that the electrostatic contribution to the salvation energy equals half of the corresponding ion-solvent interaction energy (Warshel and Russell, 1984; Roux et al., 1990). Returning now to the binding problem, this result may be exploited in the following manner: For each salvation process, i.e. salvation of the substance in water and inside the protein, two states are considered where the first has the substance in vacuum and a non-polar cavity (given, e.g., by Lennard-Jones potential) already made in the given environment. The second state corresponds to the intact substance surrounded by water or the solvated protein. The linear response approximation will then again give that $\Delta G_{bind}^{el} \cong \tfrac{1}{2} <V_{X\text{-}s}^{el}>$, where $V_{X\text{-}s}^{el}$ is the solute-solvent electrostatic term. Hence, the electrostatic contribution to the binding free energy can be approximated by $\Delta G_{bind}^{el} \cong \tfrac{1}{2} <V_{X\text{-}s}^{el}>$ (where the $\Delta$ now refers to the difference between protein and water) and thus obtained from two MD simulations of the solvated substance and of the substance-protein complex.

The validity of the linear response results in the case of ionic salvation has been confirmed, e.g., in the study by Roux et al. (1990). Some additional calculations were also performed on simple systems that corroborate the approximation of equation b. These tests were carried out by comparing the free energy obtained from FEP/MD simulations of charging $Na^+$ and $Ca^{2+}$ ions in a spherical water system (Åqvist, 1990) with the corresponding $<V_{X\text{-}s}^{el}>$ from 75 ps MD trajectories. This yielded factors relating $<V_{X\text{-}s}^{el}>$ to $\Delta G_{sol}^{el}$ of 0.49 for $Na^+$ and 0.52 for $Ca^{2+}$, both values being close to the predicted result of ½. A similar test on the charging of a methanol molecule, given by the OPLS potential (Jorgensen, 1986) in water gave a $\Delta G_{sol}^{el}/<V_{X\text{-}s}^{el}>$ ratio of 0.43.

A crucial question is how to account for the contribution of non-polar interactions and hydrophobic effects to the free energy of binding which was termed $\Delta G_{bind}^{vdw}$. In the ideal case, it should be possible to estimate this contribution from the non-polar (or van der Waals) interaction energies. The liquid theories of Chandler and coworkers (Chandler et al., 1983; Pratt and Chandler, 1977) have been successfully used to analyze hydrophobic effects and to calculate free energies of transfer for some non-polar molecules (Pratt and Chandler, 1977), but no analytical treatment of that kind seems possible for salvation in an inhomogeneous environment such as a protein's active site. However, it has been noted that the experimental free energy of salvation for various hydrocarbon compounds, such as n-alkanes, depends approximately linearly on the length of the carbon chain both in their own liquids as well as in water (Ben-Naim and Marcus, 1984). MD simulations of n-alkanes solvated in water and in a non-polar van der Waals solvent have been carried out, which indicate that also the average solute-solvent interaction energies vary approximately linearly with the number of carbons in the chain (the relationships being different in different solvents, of course). It thus seem possible that a simple linear approximation of $\Delta G_{bind}^{vdw}$ from $<\Delta V_{X\text{-}s}^{vdw}>$ might be able to account for the non-polar binding contribution. For instance, if $\sigma$ is considered some appropriate measure of the size of the solute and if the solute-solvent van der Waals interaction energies and the corresponding non-polar free energy contributions (both in water and protein) depend linearly on $\sigma$, such that $$<V_p^{vdw}> = \alpha_p \sigma, \; <V_w^{vdw}> = \alpha_w \sigma, \; \Delta G_p^{vdw} = \beta_p \sigma \text{ and } \Delta G_w^{vdw} = \beta_w \sigma$$

then $$\Delta G_{bind}^{vdw} = \frac{\beta_p - \beta_w}{\alpha_p - \alpha_w} <\Delta V_{X\text{-}s}^{vdw}>$$

is obtained. Since it seems difficult to derive a factor relating the two quantities in a reliable way from purely theoretical considerations, the approach is taken to empirically try to determine such a relationship which is capable of reproducing experimental binding data. Thus, the free energy of binding is in one embodiment of the invention approximated by $$\Delta G_{bind} = \tfrac{1}{2} <\Delta V_{X\text{-}s}^{el}> + \alpha <\Delta V_{X\text{-}s}^{vdw}> \quad (1)$$

the parameter $\alpha$ being determined by empirical calibration. Although, as discussed above, a theoretical prediction of the coefficient for $<\Delta V_{X\text{-}s}^{el}>$ is ½, it may be practically useful to also treat this coefficient as an empirical parameter. This would lead to the free energy of binding being approximated by $$\Delta G_{bind} = \beta <\Delta V_{X\text{-}s}^{el}> + \alpha <\Delta V_{X\text{-}s}^{vdw}> \quad (1b)$$

where both parameters, $\alpha$ and $\beta$, are determined by empirical calibration.

Finally, in some cases, it seems suitable to add an additional constant term to Equation 1, so that the equation becomes $$\Delta G_{bind} = \tfrac{1}{2} <\Delta V_{X\text{-}s}^{el}> + \alpha <\Delta V_{X\text{-}s}^{vdw}> + c \quad (2)$$

where c is a constant reflecting extrapolation to zero size of the chemical substance, that is, where the regression line is distinctly offset from origin when moving towards zero size of the chemical substance. The parameter c may also be used to correct for possible systematic errors due to e.g. the neglect of induced polarisation, possible force field deficiencies etc. In these cases, c will normally assume a value between −10 and 10 kcal/mol, typically between −3 and 3 kcal/mol, such as between −2 and 2 kcal/mol, e.g. between −1 and 1 kcal/mol. However, it is anticipated that in many cases, c can suitably be set to zero, as the extent of deviation will be of minor importance for the usefulness of the predicted values.

If also the electrostatic coefficient i treated as an empirical parameter, the approximation of the binding free energy assumes its most general form, namely $$\Delta G_{bind} = \beta <\Delta V_{X\text{-}s}^{el}> + \alpha <\Delta V_{X\text{-}s}^{vdw}> + c \quad (2b)$$

where now both $\alpha$, $\beta$ and c are to be determined by empirical calibration.

While the solvent used in the above method is suitably and most often an aqueous solvent like water, it is within the scope of the invention to take any other suitable solvent as a starting point, including, e.g., methanol, ethanol, acetone, acetonitrile, chloroform, hexane, etc., or mixtures thereof or combinations of such solvents or mixtures thereof with water. The selection of the solvent will be of little importance to the predicted values as long as the solvent is one which is able to dissolve or solvate the receptor molecule and the substance (in the present context this means that a sufficient amount of the periplasmic molecular chaperone or analogue thereof can be homogeneously mixed with the solvent without precipitation so as to allow the determination of binding energies by some suitable method), but there may be cases where it is advantageous to modify the solvent environment (e.g. by modulating the ionic strength) in which the interaction of the substance and the receptor molecule is to take place. If the environment in which the interaction between the chemical substance, such as a drug, and a periplasmic molecular chaperone or an analogue thereof is to take place in the actual use of the drug is the human body, it might be particularly suitable to imitate e.g. human plasma as the solvent.

A thorough discussion of the above-referenced method for determining the binding free energy between two molecules can be found in International Patent Application No. PCT/IB94/00257 and in Åqvist et al, 1994. These two documents are hereby incorporated by reference.

The above referenced method for determining the binding free energy has been employed in example 3 in order to identify compounds which stands a high chance of binding to the binding site of PapD; this means that calculations as the above described have been performed as the last theoretical step before compounds have actually been synthesized.

It will be understood that the above mentioned methods for identifying substances capable of interacting with chaperones will prove especially efficient in identifying substances which are of potential pharmaceutical value if the site to which they bind is known to be involved in pilus assembly.

Therefore, it is preferred that the site with which the substance may potentially interact, and to which the binding free energy is predicted, is the pilus subunit binding part of a molecular chaperone, such as the pilus subunit binding site of a molecular chaperone selected from the group consisting of PapD, FimC, SfaE, FaeE, FanE, Cs3-27, F17D, ClpE, EcpD, Mrkb, FimB, SefB, HifB, MyfB, PsaB, PefD, YehC, MrpD, CssC, NfaE, AggD and Caf1M, or an analogue of such a pilus subunit binding site, since the pilus subunit binding sites in these chaperones show extensive homologies. It is especially preferred that the binding site is the pilus subunit binding site of PapD or an analogue thereof.

As will appear from the examples, an important part of the chaperone binding motif has been discovered and a peptide corresponding to this motif has been synthesized and co-crystallized with PapD to provide a structural basis for the mechanism of action of PapD. The molecular details of the PapD-adhesin recognition interface clearly demonstrate the function of the conserved cleft in the entire pilus chaperone superfamily in subunit binding and in shuttling virulence determinants to the surface of pathogenic bacteria. The PapD-peptide crystal structure essentially represents a "snapshot" of a fundamental process in bacterial pathogenesis: the interaction of an adhesin with a chaperone, which is a prerequisite to adhesin presentation on the microbial surface.

Thus, the inventors of the present invention have by the use of X-ray crystallography elucidated the mechanism of binding between PapD and the pilus subunit PapG thereby identifying an essential part of a defined binding site responsible for the binding between pilus subunits and their periplasmatic chaperones, and thus providing a method to enable drug design of chaperone inhibiting anti-bacterial compounds.

Having determined the location of a promising binding site for inhibitory ligands as described above (see details in examples 1 and 2), the computer programs "PLIM" and "PLIM_DBS" (developed by Symbicom AB) have been used to find templates for families of compounds capable of binding to the binding site.

PLIM is a Protein Ligand Interaction Modeller that constructs putative ligands for a protein using thermodynamic criteria. It calculates the energy of interaction between the protein and sample probes that are successively placed at different points on a regular grid around the molecule. For each position and orientation the interaction energy between the probe and the atoms of the protein is calculated. The energies are stored, and the best positions for a particular probe are written out (the basic calculations are described by Goodford (1985) and Boobbyer (1989) and implemented in the commercially available program GRID; the PLIM implementation is somewhat different in that the energy values are converted to discrete points that are associated with the chemical probe, enabling easy output to e.g. data base searching programs). The program then builds up the ligand by incorporating selected probe atoms at positions of energy minima on the grid. The user selects which atoms and groups should be used as probes, and which criteria should be used to determine those that will be incorporated into the ligand. The energy is calculated as the sum of electrostatic, Van der Waals and hydrogen-bonding contributions as described herein.

The PLIM runs result in a number of suggested positions and orientations of favourable chemical groups in the region near the binding site. These groups which have physical properties like charge, hydrogen bonding directionality and extended atom radia, will hereafter be denoted "site points".

A search for potential ligands is then made by searching a database for known molecular structures that match the positions of these groups of site points, using PLIM_DBS.

The core of PLIM_DBS is an algorithm for subgraph isomorphism (cf. Ullman (1976) and Brint (1987)), where three sitepoints are represented as a distance matrix ("the pattern matrix"). The program looks for this distance pattern in the distance matrix formed from every entry in the database. If the pattern is found, the entry is superimposed on to the sitepoints and if the corresponding atom types match the entry and its orientation is saved in a hit-list. Added to this basic scheme a number of options regarding surface complementarity can be used, i.e. only entries which are matching the protein surface with respect to hydrophobic and steric properties are saved.

PLIM_DBS is thus a database searcher which hunts through a collection of 3-dimensional molecule coordinate sets, looking for entries that contain a certain pattern of atoms. This pattern is specified in terms of atom type, and of spatial position and orientation; for instance a search may be made for compounds containing an sp3 carbon atom that is 4.2 Å from a sp2 oxygen and 5.1 Å from a hydroxyl group that in turn is 5.6 Å from the oxygen. The strictness of the search can be adjusted by the user by varying the tolerance on the distance criteria and the atom-type matching, determining, for instance, whether a sp2 carbon that is a little more than 4.2 Å from an oxygen should be considered as a hit. Those hits that are found are then ranked according to a score that reflects how well the target atoms superimpose on the real molecule, and also on how complementary the molecular surface of the compound is to that of the binding pocket of the protein.

The result from a PLIM_DBS search is a list of molecular structures and their atomic coordinates, superpositioned on to the sitepoints, and given a score ("goodness of fit").

The procedure does not try to optimize the positioning of the structures, nor does it perform any molecular mechanics or dynamics calculations. Both protein and the extracted structures are treated as rigid bodies.

The structures from the database search are displayed in the context of the protein and its surface on a graphics system using a commonly available molecular modelling package. Usually the structures show some unfavourable interactions with the protein, or lack groups to fill out e.g. hydrophobic pockets. Hence, the structures form the database search are regarded as templates, to be modified and improved by an organic chemist. This process also involves choosing compounds which are easy to synthesize, which is of particular interest if the synthesis capacity is limited.

The best of these database hits are thus examined visually using a computer-graphic modelling system, and the most promising of these are selected according to a wealth of physico-chemical reasoning.

The templates are modified using a small molecule 3D builder (MacMimic). Each template gives rise to a compound class, e.g. denoted "hdo". Each modification assigned a specific number (e.g. hdo_3) and the coordinates and a description are stored in a tree structure, using the program ARVS_JAKT developed by Symbicom. The design is performed in a collaboration between protein structure experts and organic chemists, in order to provide the best tools possible for the chemists who will actually synthesize the compounds.

The efficacy of these modifications is finally assessed using molecular-dynamics free energy calculations as described herein to study the stability of the protein-ligand complex (Åqvist et al., 1994; Åqvist and Medina, 1993).

In order to maximize the efficiency of the above-mentioned methods for identifying/designing substances which are capable of interacting with a molecular chaperone, it is preferred that the substance A is likely to be a substance which is capable of binding to the selected binding site.

In view of the above-described modus operandi for selecting substances which should interact with chaperones like PapD, this can, according to the invention, be accomplished when the substance A is selected by performing the following steps:

co-crystallizing the periplasmic molecular chaperone or the analogue thereof with a ligand capable of interacting with a site in the periplasmic molecular chaperone or the analogue thereof and establishing the three-dimensional conformation of the periplasmic molecular chaperone or the analogue thereof and the ligand when interacting by means of X-ray crystallography, using the above-established conformation of the periplasmic molecular chaperone or the analogue thereof to establish a 3-dimensional representation of the site in the periplasmic molecular chaperone or the analogue thereof interacting with the ligand during binding, selecting a number of distinct chemical groups, X1, and determining the possible spatial distributions of the X1 chemical groups which maximizes the binding free energy between the chemical groups and the site in the chaperone or the analogue interacting with the ligand, extracting, from a database comprising three-dimensional representations of molecules, a molecule which has the X1 chemical groups in the possible spatial distributions determined above, optionally modifying the 3-dimensional representation of the molecule extracted from the database, and identifying the optionally modified molecule as the substance A.

According to the invention the above-indicated steps are especially preferred when the ligand is a pilus subunit or a part thereof with which the chaperone normally interacts during transport of the pilus subunit through the periplasmic space and/or during pilus assembly.

By the use of the above-mentioned method for identifying substances capable of interacting with the periplasmic chaperones, several classes of substances have been identified which have proved promising in the design phase.

Drug design efforts for inhibitors/enhancers to PapD have concentrated on the region of the molecule where the G-peptide is observed to bind. This region will now be described in detail, using one of the putative inhibitors (bpy_9, see below) as a reference structure.

The binding site is dominated by the central charged side chains of Arg-8 and Lys-112, which bind to the sulphate moiety of bpy_9. Adjacent to this is a small, shallow hydrophobic pocket formed by the side-chains of Ile-154, Ile-194, and Thr-7, against which the 2-ethyl group of bpy_9 packs (Pocket 1). A group as large as a phenyl ring could be accommodated here, attached to sugar position 2, and with possible substituents that could receive or donate a hydrogen bond to Thr-7, or donate to the backbone carbonyl of 198.

There is also a larger pocket comprising residues Leu-4, Ile-111, Thr-7 and Thr-109, in which the phenyl ring of bpy_9 nestles (Pocket 2). A group as large as naphthalene could be substituted on the 6-position of the carbohydrate scaffold to fill this sub-site, with substituents that could form a hydrogen bond to Thr-109, or to any of the polar backbone atoms of residues Leu-4, Arg-6, or Lys-110. Then there is a long, shallow patch that includes Tyr-87, and the aliphatic regions of Lys-110 and Lys-112, which could accommodate a tricyclic system such as 2-phenanthryl substituted on position 3 of the sugar (Patch 3). Substituents to hydrogen bond to Tyr-87 or the backbone of Lys-110 can be considered, as well as negatively charged groups to complement the side chains of Lys-110 and Lys-112. Tyr-87 is a potential charge-transfer donor to a electron deficient π-system such as a nitroaryl.

Models of several homologous chaperones (SfaE, MrkB, HifB and FimC) have been made from the PapD structure, and differences between the model structures has influenced the design of inhibitors, such that proposed ligands should bind to all the structures looked at. For example, it is tempting to complement the charged side chain of Arg-200 with an acidic group in the ligand, but since two of the other structures have an Asp at this position, the residue is not considered as a good candidate. Arg-8 is fully conserved, as is Lys-112, Thr-7 and Ile-11. Tyr-87 becomes a Trp in three structures, but the overall nature of patch 3 is not changed by this. PapD is actually alone with its Thr-Lys sequence at 109–110, all of the four other structures being Ser-Arg here, but again, these conservative changes do not significantly alter design criteria.

Although substances which interact with the binding site responsible for binding to G-proteins are obvious candidates as inhibitors/enhancers of periplasmic chaperones, it will be understood that molecules capable of interacting with other sites in periplasmic chaperones are interesting in this aspect, too. It is highly possible that an interaction with another site than the one binding G-protein in i.e. PapD may cause PapD to either be prevented, inhibited or enhanced in its action as a periplasmic chaperone.

As mentioned above, a family of substances (called the bpy family herein) is an important aspect of the invention. Thus, the invention relates to novel compounds of the general formula:

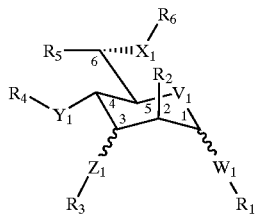

I wherein $V_1$ is O, S, SO, $SO_2$, $CH_2$, C(OH)H, CO or CS;
$W_1$ is O, S, $SO_2$, $SO_3$, $CH_2$ or NH;
$R_1$ is H; $C_{1-24}$ alkyl, $C_{1-24}$ alkenyl or $C_{1-24}$ alkynyl, which alkyl, alkenyl and alkynyl may be substituted with one or more substituents independently selected from OH, —$CONH_2$, —$CSNH_2$, —CONHOH, —CSNHOH, —NHCHO, —$NHCONH_2$, —$NHCSNH_2$, —$NHSO_2NH_2$ and $SO_2NH_2$; acyl; or —$(CH_2CH_2O)_s$—H, wherein s=1,2,3;
$R_2$ is a group of the formula

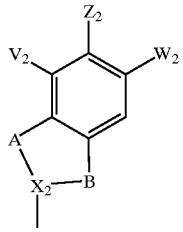

wherein

A is —CH—$(CH_2)_n$—, or —CH=CH—$(CH_2)_{n-1}$— (n>0) or

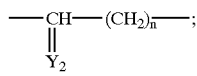

B is —$(CH_2)_m$— or =CH—$(CH_2)_{m-1}$— (m>0);
$X_2$ is N, CH or C (when B is =CH—$(CH_2)_{m-1}$—; and
$Y_2$ is O, S, NH, $H_2$ or H (n=1); and
4>m+n>0, n<3, and m<3;

or $R_2$ is a group of the formula

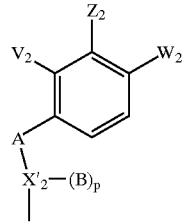

wherein

A is —CH—$(CH_2)_n$—, or —CH=CH—$(CH_2)_{n-1}$— (n>0) or

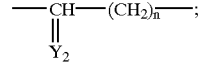

$Y_2$
B is —$(CH_2)_m$— or =CH—$(CH_2)_{m-1}$— (m>0); and
$X'_2$ is O, NH, $CH_2$ or S (when p=0); N or CH (p=1); or C (when p=1 and B is =CH—$(CH_2)_{m-1}$—);
$V_2$, $Z_2$ and $W_2$ are independently H, OH, —$CONH_2$, —$CSNH_2$, —CONHOH, —CSNHOH, —NHCHO, —$NHCONH_2$, —$NHCSNH_2$, —$NHSO_2NH_2$, —$SO_2NH_2$, or $V_2$ and $Z_2$ or $Z_2$ and $W_2$ together form —NHC(O)NH—, —C(O)NHC(O)—, —NHS($O_2$)NH—, —C(O)NHO—, —C(S)NHO—, —S($O_2$)NHO—, or —S ($O_2$)NHC(O)—;
4>m+n>0, n<3, and m<3;
or $R_2$ is a group —$W_5$—($C_{1-5}$ alkyl or $C_{2-5}$ alkenyl or $C_{2-5}$ alkynyl) wherein $W_5$ is a bond or is selected from —O—, —S—, —$SO_2$—, and —NHC(O)—, and the $C_{1-5}$ alkyl, $C_{2-5}$ alkenyl or $C_{2-5}$ alkynyl moiety may be substituted with up to three groups selected independently from OH, —$CONH_2$, —$CSNH_2$, —CONHOH, —CSNHOH, —NHCHO, —$NHCONH_2$, —$NHCSNH_2$, —$NHSO_2NH_2$ and —$SO_2NH_2$;
-$Z_1$-$R_3$ is —$SO_2$(OH), —PO(OH)$_2$, —$OSO_2$(OH), —$NHSO_2$(OH), —NH—CO—COOH, —SPO(OH)$_2$, —$CH_2$COOH, tetrazol-5-yl or tetrazol-5-ylmethyl, or salts thereof;
or $Z_1$ is —O—, —S—, —NH—, or —$CH_2$—, and $R_3$ is a group of the formula:

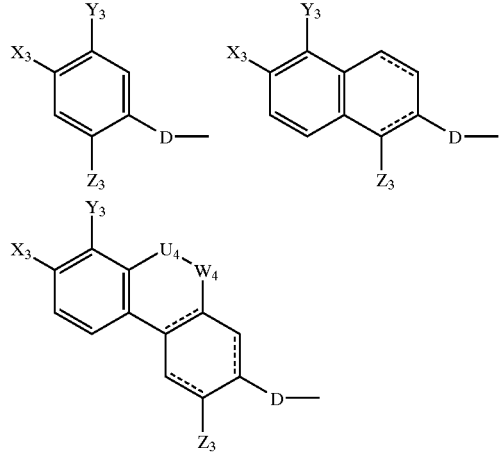

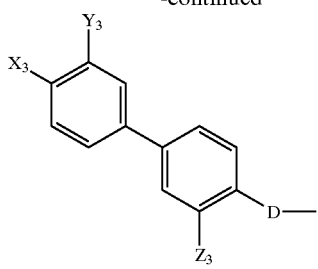

D is —CH$_2$—, —CO—, —SO$_2$—, —NH—SO$_2$—, —NH—CO—, —O—PO(OH)— or a salt thereof;

Z$_3$ is H, OH, —CONH$_2$, —CSNH$_2$, —CONHOH, —CSNHOH, —NHCHO, —NHCONH$_2$, —NHCSNH$_2$, —NHSO$_2$NH$_2$, —SO$_2$NH$_2$—, —SO$_2$(OH), —PO(OH)$_2$, —OSO$_2$(OH), —NHSO$_2$(OH), —COOH, tetrazolyl-5-yl or tetrazolyl-5-ylmethyl or a salt thereof, with the proviso that when D is —CH$_2$—, —CO—, —SO$_2$—, —NHSO$_2$— or —NHCO—, then Z$_3$ is —SO$_2$(OH), —PO(OH)$_2$, —OSO$_2$(OH), —NHSO$_2$(OH), —COOH, tetrazolyl-5-yl or tetrazolyl-5-ylmethyl or a salt thereof;

X$_3$ and Y$_3$ independently are H, NO$_2$, SO$_2$NH$_2$, CONH$_2$, CF$_3$ or F; and U$_4$—W$_4$ is —CHCH—, —CH$_2$CH$_2$—, —C(OH)CH—, —CHC(OH)—, —CH(OH)CH$_2$—, —CH$_2$CH(OH)—, —CH(OH)CH(OH)—, —C(O)NH—, —NHC(O)—;

Y$_1$ is —O— or —S—;

R$_4$ is H or, when Y$_1$ is S, S(CH$_2$)$_q$N(R$_9$)$_3^+$ and q is an integer 2–4, where R$_9$ is H or CH$_3$;

R$_5$ is H; C$_{1-6}$ alkyl, C$_{2-6}$ alkenyl or C$_{2-6}$ alkynyl, and the C$_{1-6}$ alkyl, C$_{2-6}$ alkenyl or C$_{2-6}$ alkynyl moiety may be substituted with OH, —CONH$_2$, —CSNH$_2$, —CONHOH, —CSNHOH, —NHCHO, —NHCONH$_2$, —NHCSNH$_2$, —NHSO$_2$NH$_2$ or —SO$_2$NH$_2$; or aryl, aryl(C$_{1-2}$)alkyl, heterocyclyl, or heterocyclyl(C$_{1-2}$)alkyl which may optionally be substituted in the aryl or heterocyclyl moieties with one, two or three substituents selected independently from OH, F, Cl, NH$_2$, CONH$_2$, NHCOH, and SO$_2$NH$_2$;

X$_1$ is —O—, —S— or —NH—;

R$_6$ is H or, when X$_1$ is NH, acyl, HOCNH-Val-Met-, HOCNH-Ile-(S,S)-dioxo-methionyl- or HOCNH-Val-(pyran-4-on-2-yl)-ala-nyl-;

or a salt of such a compound.

Another family of substances called the hdo-family has also been synthesized. Hence, the invention also relates to novel compounds of the general formula

II

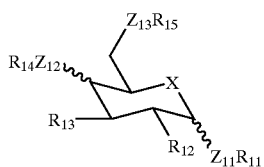

wherein

X is O, P, P(O), S, SO, SO$_2$, CH$_2$, C(OH)H, or a group NQ$_{11}$, wherein Q$_{11}$ is H, OH, C$_{1-24}$ acyl or C$_{1-24}$ alkyl;

Z$_{11}$ is a bond, O, CH$_2$, S, SO, SO$_2$, or a group NQ$_{12}$, wherein Q$_{12}$ is H, C$_{1-24}$ acyl or C$_{1-24}$ alkyl;

R$_{11}$ is H; C$_{1-24}$ alkyl, C$_{2-24}$ alkenyl, or C$_{2-24}$ alkynyl, which may be substituted with one or more substituents independently selected from —OH, —COOH, —F, —Cl, —CONH$_2$, —CSNH$_2$, —CONHOH, —CSNHOH, —NHCHO, —NHCONH$_2$, —NHCSNH$_2$, —NHSO$_3$NH$_2$ and —SO$_2$NH$_2$; acyl; or —(CH$_2$CH$_2$O)$_s$—H, wherein s=1, 2, or 3;

or R$_{11}$ is CH=CH—(CH$_2$)$_{n'}$—Q$_{13}$ or —(CH$_2$)$_{n'}$—Q$_{13}$, wherein Q$_{13}$ is an aryl or a heteroaryl group substituted with —OH, —COOH, —F, —Cl, —CONH$_2$, —CSNH$_2$, —CONHOH, —CSNHOH, —NHCHO, —NHCONH$_2$, —NHCSNH$_2$, —NHSO$_3$NH$_2$ and —SO$_2$NH$_2$, and wherein n'≧0;

R$_{12}$ and R$_{13}$ are independently OH, H, F, Cl, OW$_{11}$, or O(CO)W$_{11}$, wherein W$_{11}$ is C$_{1-24}$ alkyl, C$_{2-24}$ alkenyl or C$_{2-24}$ alkynyl, or an aryl or a heteroaryl group substituted with —OH, —COOH, —F, —Cl, —CONH$_2$, —SNH$_2$, —CONHOH, —CSNHOH, —NHCHO, —NHCONH$_2$, —NHCSNH$_2$, —NHSO$_3$NH$_2$ and —SO$_2$NH$_2$;

Z$_{12}$ is a bond, O, S, or CH$_2$;

R$_{14}$ is —(CH$_2$)$_{n''}$—Q$_{14}$, wherein Q$_{14}$ is an aryl group or a heteroaryl group substituted with —OH, —COOH, —F, —Cl, —CONH$_2$, —CSNH$_2$, —CONHOH, —CSNHOH, —NHCHO, —NHCONH$_2$, —NHCSNH$_2$, —NHSO$_3$NH$_2$ and —SO$_2$NH$_2$, and wherein n''=0, 1, 2, or 3;

Z$_{13}$ is a bond, O, CH$_2$, S, SO, SO$_2$, NQ$_{14}$Q$_{15}$, wherein Q$_{14}$ is H, C$_{1-24}$ acyl or C$_{1-24}$ alkyl, and Q$_{15}$ is CO or —C(O)W$_{12}$, wherein W$_{12}$ is O or NW$_{13}$, wherein W$_{13}$ is H, OH, C$_{1-24}$ acyl or C$_{1-24}$ alkyl;

R$_{15}$ is H; C$_{1-24}$ alkyl, C$_{2-24}$ alkenyl or C$_{2-24}$ alkynyl, which alkyl, alkenyl and alkynyl may be substituted with one or more substituents independently selected from, —OH, —COOH, —F, —Cl, —CONH$_2$, —CSNH$_2$, —CONHOH, —CSNHOH, —NHCHO, —NHCONH$_2$, —NHCSNH$_2$, —NHSO$_3$NH$_2$ and —SO$_2$NH$_2$; acyl or —(CH$_2$CH$_2$O)$_s$—H, wherein s=1, 2, or 3;

or R$_{15}$ is CH=CH—(CH$_2$)$_{n'}$—Q$_{13}$, or —(CH$_2$)$_{n'}$—Q$_{13}$, wherein Q$_3$ is as defined above and wherein n'≧0;

or a salt of such a compound.

In the present context, the terms "C$_{1-5}$, C$_{1-6}$ and C$_{1-24}$ alkyl" is intended to mean alkyl groups with 1–5, 1–6 and 1–24 carbon atoms, respectively, which may be straight or branched or cyclic such as methyl, ethyl, propyl, isopropyl, butyl, isobutyl, tert.butyl, hexyl, octyl, dodecyl, cyclopentyl, cyclohexyl, etc.

Further, as used herein, the terms "C$_{2-5}$, C$_{2-6}$ and C$_{2-24}$ alkenyl" is intended to mean mono- or polyunsaturated alkyl groups with 2–5 and 2–24 carbon atoms, respectively, which may be straight or branched or cyclic in which the double bond(s) may be present anywhere in the chain or the ring, for example vinyl, 1-propenyl, 2-propenyl, hexenyl, decenyl, 1,3-heptadienyl, cyclohexenyl etc. Some of the substituents exist both in a cis and a trans configuration. The scope of this inventions comprises both the cis and trans forms.

In the present context, the terms "C$_{2-5}$, C$_{2-6}$ and C$_{2-24}$ alkynyl" is intended to mean a straight or branched alkyl group with 2–5 and 2–24 carbon atoms, respectively, and incorporating one or more triple bond(s), e.g. ethynyl, 1-propynyl, 2-propynyl, 2-butynyl, 1,6-heptadiynyl, etc.

The terms "C$_{1-6}$ and C$_{1-24}$ alkoxy" designate alkyl groups as defined above comprising an oxy function.

In the present context, the term "aryl" is intended to mean phenyl and naphthyl. The term "heteroaryl" is intended to mean a cyclic aromatic system, wherein at least one non-carbon atom contributes to the π bonding system.

Examples of substituted aryl groups are: 3-nitrophenyl, 3-hydroxyphenyl, 4-hydroxyphenyl, 3,4-dihydroxyphenyl, 3-carboxamidophenyl, 3-formamidylphenyl, 3-acetamidylphenyl, 3-fluoronaptht-2-yl, 7-fluoronaphthyl, 3,7-difluoronaphthyl, 3-hydroxynaphthyl, 7-hydronaphthyl, 3,7-dihydroxynaphthyl, 3-fluoro-7-hydroxynaphthyl, 7-fluoro-3-hydroxynaphthyl, 4-fluoronaphth-2-yl, 6-fluoronaphth-yl, 8-fluoronaphth-2-yl, 4,6-difluoronaphth-2-yl etc.

Examples of heterocyclic and heteroaryl groups are pyrrolyl, furanyl, 2,3-dihydrofuranyl, tetrahydrofuranyl, thienyl, 2,3-dihydrothienyl, tetrahydrothienyl, imidazolyl, oxazolyl, thiazolyl, pyrazolyl, indolyl, pyrazinyl, dioxolanyl, dioxanyl, 1,3,5-trioxanyl, tetrahydrothiapyranyl, dithiolanyl, pyrazolidinyl, iminazolidinyl, sym-triazinyl, sym-tetrazinyl, quinazolinyl, pteridinyl, isoindolyl, 1,2,4-triazolyl, 1,2,3-triazolyl, benzimidazolyl, indazolyl, benzofuranyl, isobenzofuranyl, benzothiophenyl, thienothiophenyl, isoxazolyl, 1,2,5-oxadiazolyl, isothiazolyl, 1,3,4-thiadiazolyl, benzoxazolyl, benzothiazolyl, azaindolyl, oxoindolyl, hydroxyindolyl, N-oxyisoquinolyl etc.

In the present context, the term "acyl" (e.g. $C_{1-24}$ acyl) is intended to designate the acyl residue of a carboxylic acid or a sulphonic acid moiety comprising a carbonyl or sulphonyl group and an organic moiety. Examples of acyl groups include $C_{1-24}$ alkanoyl (e.g. formyl, acetyl, propionyl, butyryl, isobutyryl, valeryl, isovaleryl, pivaloyl and hexanoyl), $C_{1-24}$ alkenoyl (e.g. acryloyl, metacryloyl, crotonoyl, isocrotonoyl, 2-pentenoyl, 3-pentenoyl, 2-methylpentenoyl, 3-pentenoyl, 3-phenylpropenoyl, 2-phenyl-trans-propenoyl, 2,4-hexadienoyl), $C_{1-24}$ alkynoyl (e.g. propyonyl, 2-butynoyl, 3-butynoyl, 2-methyl-3-butynoyl, 2,2-dimethylbutynoyl, 2-pentynoyl, 3-pentynoyl, 2-pentyn-4-trans-enoyl), $C_{1-24}$ alkoxycarbonyl (e.g. methoxycarbonyl, ethoxycarbonyl, propoxycarbonyl, butoxycarbonyl and t-butoxycarbonyl), $C_{1-24}$ alkenyloxycarbonyl (e.g. cis-2-butenyloxycarbonyl, 1-methyl-2-propenyloxycarbonyl, 1,1-dimethyl-2-propenyloxycarbonyl, trans-2-butenyloxycarbonyl), aroyl (e.g. benzoyl), heterocyclylcarbonyl (e.g. 2-furoyl, 3-furoyl, 2-furanoyl, 3-furanoyl, 2-pyrrolcarboxyl, 3-pyrrolcarboxyl, 2-thenoyl, 3-thenoyl, 2-indolcarboxyl, 3-indolcarboxyl, 1-naphthanoyl and 2-naphthanoyl), etc.

The term "salt" is intended to comprise a salt such as an organic acid addition salt (e.g. acetate, valerate, salicylate, galacturonate, gluconate, tannate, triflouroacetate, maleate, tartrate, methanesulfonate, benzenesulfonate, formiate, thiocyanate and toluenesulfonate), an inorganic acid addition salt (e.g. hydrochloride, hydrobromide, hydroiodide, dihydrochloride, dihydrobromide, dihydroiodide, sulphate, hydrogensulphate, halosulphate such as iodosulphate, nitrate, phosphate, and carbonate) or a salt with an amino acid (e.g. arginine, aspartic acid and glutamic acid) or a metal salt such as an alkali metal salt (e.g. sodium salt and potassium salt) and an earth alkali metal salt (e.g calcium salt and magnesium salt), an ammonium salt, an organic alkali salt (e.g. trimethylamine salt, triethylamine salt, pyridine salt, picoline salt, dicyclohexylamine salt and N,N'-dibenzylethylenediamine salt), and hydrates thereof.

When the substituent $R_5$ designates heterocyclyl, it is preferred that the substituent designates a heterocyclyl group of the formula

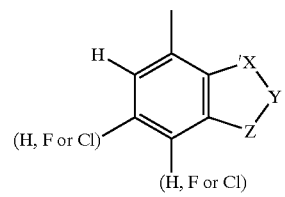

wherein 'X is —CH—, —CH$_2$—, —O—, —N—, —S—, —S→O, —N→O or —CO—, Y is —CH— or —NH—, and Z is —CH—, —CH$_2$—, —O—, —S—, —N—, —CO—, —S→O or —N→O, especially a group selected from the group consisting of inden-7-yl, benzofuran-4-yl, isobenzofuran-4-yl, thionaphthen-4-yl, isothionaphthen-4-yl, 2-oxo-inden-7-yl, 2-oxo-inden-4-yl, inden-4-yl, benzofuran-7-yl, isobenzofuran-7-yl, thionaphten-7-yl, isothionaphthen-7-yl, 1-oxothionaphthen-4-yl, 1-oxothionaphthen-7-yl, anthran-4-yl, anthran-7-yl, thioanthran-4-yl, thioanthran-7-yl, benzthiozol-4-yl, benzthiozol-7-yl, 2H-2-isobenzo-1,3-dion-7-yl, isobenzofuran-5-yl, isobenzofuran-6-yl, 3H-2-oxo-benzofuran-5-yl, 3H-2-oxobenzofuran-6-yl, 3H-2-oxothionaphthen-5-yl, 3H-2-oxothionaphthen-6-yl, indol-5-yl, indol-6-yl, 3H-2-oxoindol-5-yl, 3H-2-oxoindol-6-yl, 3H-2-oxobenzoxazol-5-yl, 3H-2-oxobenzoxazol-6-yl, benzothiazol-5-yl, benzothiazol-6-yl, 2-oxobenzo-1,3-dithiol-5-yl, 2-oxobenzo-1,3-dithiol-6-yl, 3H-2-oxobenzimidazol-5-yl, 3H-2-oxobenzimidazol-6-yl, benzoxathiol-5-yl, benzoxathiol-6-yl, 3H-2-oxobenzthiazol-5-yl and 3H-2-oxobenzthiozol-6-yl.

It is also preferred that the substituent $R_5$ is a group of the formula

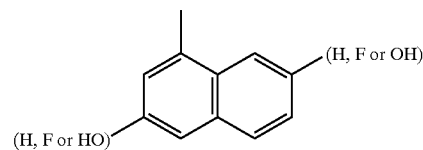

or that $R_5$ is a group of the formula

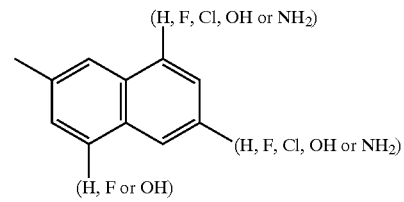

With respect to the substituent $R_2$ being heterocyclyl, it is especially preferred that it is selected from the group consisting of isobenzofuran-5-yl, isobenzofuran-6-yl, 3H-2-oxo-benzofuran-5-yl, 3H-2-oxo-benzofuran-6-yl, 3H-2-oxothionaphthen-5-yl, 3H-2-oxothionaphthen-6-yl, indol-5-yl, indol-6-yl, 3H-2-oxoindol-5-yl, 3H-2-oxoindol-6-yl, 3H-2-oxobenzoxazol-5-yl, 3H-2-oxobenzoxazol-6-yl, benzothiazol-5-yl, benzothiazol-6-yl, 2-oxobenzo-1,3-dithiol-5-yl, 2-oxobenzo-1,3-dithiol-6-yl, 3H-2-oxobenzimidazol-5-yl, 3H-2-oxobenzimidazol-6-yl, benzoxathiol-5-yl, benzoxathiol-6-yl, 3H-2-oxobenzthiazol-5-yl and 3H-2-oxobenzthiozol-6-yl.

The exact number of substituents present on an alkyl, alkenyl or alkynyl moiety $R_1$ will be dependent on the length of the carbon chain, the purpose of the substituents being to cause the entire group $R_1$ to be compatible with water since, in the chaperone-ligand-complex such as the PapD-ligand complex, the group $R_1$ will extend into the surrounding aqueous medium. Thus, for a fairly short carbon chain such as up to four carbon atoms, it is contemplated that one of the above polar substituents will be sufficient, in particular when the substituent is located terminally whereas, for longer chains, a larger number of substituents, such as a substituent for every other carbon atom, may be required.

The 4,6-O-(4'-Methoxy)phenylmethylidene-α-D-glucohexopyrano-side or 4,6-O-(4'-Methoxy)phenylmethylidene-β-D-glucohexopyranoside glycosides:

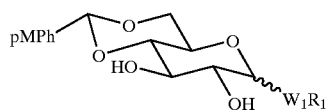

A (used here as preferred examples, but other arylmethylidene or vinylidene acetals may be used) can be prepared as follows: Peracylated glucose is reacted with, e.g. hydrogen bromide or hydrogen chloride in a suitable solvent such as, e.g. acetic acid or dichloromethane, to form per-O-acylated glycosyl bromide or chloride (O-acylation and glycosyl halide synthesis: M. L. Wolfrom and A. Thompson, *Methods in Carbohydrate Chemistry*, Vol. 2, 211–215, ed. by R. L. Whistler and L. Wolfrom, Academic Press, New York, 1963; G.Hewit and G. Fletcher Jr., ibid, 226–228; and R. U. Lemieux, ibid, 223–224).

The suitably protected, when necessary, aglycone alcohol or thiol (H—$W_1R_1$-$PG_1$ or H—$W_1R_1$) (protecting groups: *Protective Groups in Organic Synthesis*, Editors T. W. Greene and P. G. M. Wuts, John Wiley & Sons, Inc., New York, 1991) is reacted with the per-O-acylated glucose using a Lewis acid such as borontrifluoride etherate (R. J. Ferrier and R. H. Furneaux, *Carbohydr. Res.*, 52 (1976) 63–68; J. Dahmen, T. Frejd, G. Grönberg, T. Lave, G. Magnusson, and G. Noori, *Carbohydr. Res* 116 (1983) 303–307) or trimethylsilyltrifluoromethanesulphonate (T. Ogawa, K. Beppu, S. Nakabayashi, *Carbohydr. Res.*, 93 (1981) C6–C9) as promoters. The reaction is carried out in a suitable solvent such as chloroform, dichlorometane, or toluene. When the monosaccharide derivative in question is a per-O-acylated glycosyl bromide or chloride, promoters such as silver trifluoromethane sulphonate or mercury (II) salts (H. Paulsen, *Angew. Chem. Int. Ed. Engl.*, 21 (1982) 155–173) can be used and the reactions are carried out in a suitable solvent such as dichlorometane or toluene. The glucose $W_1R_1$ or $W_1R_1PG_1$-glycosides are obtained after de-O-acylation using sodium methoxide (A. Thompson, M. L. Wolfrom, and E. Pascu, page 215–220, *Methods in Carbohydrate Chemistry*, Vol II, Editors: R. L. Whistler and M. L., E. Wolfrom, Academic Press, New York, 1963) in methanol or in methanol containing a co-solvent such as dichlormethane or tetrahydrofurane.

The 4,6-(4'-methoxy)benzylidene acetals are then obtained by reaction with 4-methoxybenzaldehyde dimethyl acetal and acid in a polar non-protic solvent such as e.g. dimethyl formamide, acetonitrile or tetrahydrofurane (J. J. Patroni et al., *Aust. J. Chem.* 1988, (41),91–102; for other methods of acetal formation, see for example A. N. de Belder, 1979, *adv. Carbohydr. Chem. Biochem.*, 34, 179 and references cited therein).

The epoxides B1 or B2

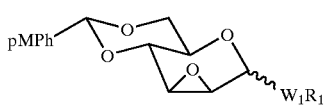

B₁

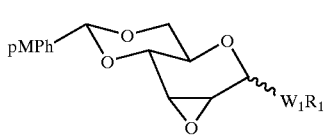

B₂ are then obtained through sulphonate esters: The manno epoxides B1 can be prepared by reacting the glucoside derivative A with sodium hydride and p-toluenesulphonylimidazol in dimethylformamide (D. Hicks and B. Fraser-Reid; *Synthesis* 1974, 203) or with sodium hydride and p-toluenesulphonyl chloride in tetrahydrofurane (V. S. Murthy et al, *Synthetic Commun.* 1993, 23(3), 285–289).

The allo epoxides B2 can be prepared by reacting the glucoside derivative A with methylsulphonyl or p-toluenesulphonyl chloride in pyridine and treating the resulting methylsulphonate diester with sodium ethoxide in ethanol (Y. Ali, A. C. Richardson, *Carbohydrate Res.* 1967, 5, 441–448; N. Richtmeyer, *Methods in Carbohydrate Chemistry*, Vol 1,107).

The epoxides B1 or B2 can be reacted with suitable nucleophilic reagents to yield the diaxially substituted allo hexopyranosides C1 and C2

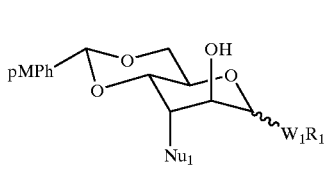

C₁

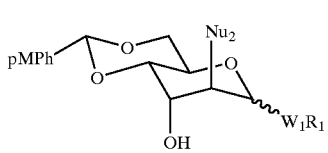

C₂

(for general references on the use of epoxides, see e.g. J. Gorzynski Smith, Synthesis, 1984, 8, 629–656 Masamune S., Choy W., Petersen J S, and Sita L R, *Angew. Chem. Int. Ed. Engl.*, 1985, 24, 1–76; A. S. Rao et al., Tetrahedron Lett., 1983, 39, 2323).

When the first atom of $R_2$ and $Z_1$ (as defined above) connected to the carbohydrate moiety in the desired final product is a nitrogen (=the nucleophilic atom), then the preferred nucleophile $Nu_1$ or $Nu_2$ is azide ($N_3^-$). The epoxide is treated with sodium azide and ammonium chloride in boiling 2-methoxyethanol (R. D. Guthrie and D. Murphy; *J.Chem.Soc.* 1963, 5288–5294).

When the nucleophilic atom is oxygen or sulphur, the preferred general method of epoxide opening involves treatment with suitably protected alcohol or thiol in the presence of neutral alumina in ether (G. H. Posner and D. Z. Rogers, *J. Am. Chem. Soc.* 1977, 99, 8208; G. H. Posner, D. Z. Rogers and A. Romero, *Isr. J. Chem.* 1979, 18, 259; and G. H. Posner, M. Hulce and R. K. Rose, *Synth. Commun.* 1981, 11, 737).

When the nucleophilic atom is carbon, the most commonly used reagents are organomagnesium, organolithium, organocopper, organoaluminium and organoboron compounds (J. Gorzynski Smith, *Synthesis*, 1984, 8, 629–656 and references cited therein).

When the product is an allo hexopyranoside C1, the 2-hydroxy function can either be blocked with a protective group that allows for the introduction of the $R_2$ functionality at a later stage (preferred if $R_2$ is an ester, not shown in figure), or the suitably protected, when necessary, functionality $R_2$ is introduced to produce D1

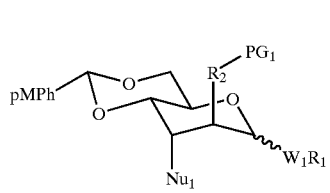

D1

For example, OH-groups to ethers or esters (*Protective Groups in Organic Synthesis*, Editors T. W. Greene and P. G. M. Wuts, John Wiley & Sons, Inc., New York, 1991); OH-groups to carbonates (J. March, *Advanced organic Chemistry-Reaction Mechanisms, and Structure*, 3rd Edn. John Wiley & Sons, New York, 347 (1985), and references cited therein); OH-groups to carbamates (J. March, *Advanced Organic Chemistry-Reaction Mechanisms, and Structure*, 3rd Edn. John Wiley & Sons, New York, 791–792 (1985), and references cited therein); OH-groups to alkyl-groups via exomethylene derivatives and subsequent hydrogenation or via other routes (H. O. H. House, *Modern Synthetic Reactions*, 2nd Edn. W. A Benjamin, Inc., Menlo Park, Calif., 1–130 (1972), and references cited therein; J. Yoshimura, *Adv. Carbohydr. Chem. Biochem.*, 42 (1984) 69–134); and exchange of OH-groups for heterocyclic groups, via different routes (A. R. Katritzky, *Handbook of Heterocyclic Chemistry*, Pergamon Press, Oxford, 1985).

When the product is an allo hexopyranoside C2, the 3-hydroxy function is blocked with a protective group that allows for the introduction of the $Z_1$-$R_3$ functionality at a later stage resulting in intermediates of the type D2

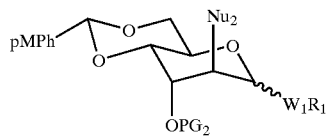

D2

(*Protective Groups in Organic Synthesis*, Editors T. W. Greene and P. G. M. Wuts, John Wiley & Sons, Inc., New York, 1991) or transformed to a manno hexopyranoside intermediate D3

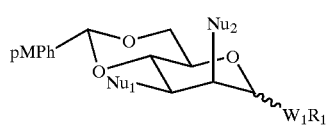

D3 where $Nu_1$ is a protected or masked form of the functionality $Z_1$. OH-groups to ethers or esters (*Protective Groups in Organic Synthesis*, Editors T. W. Greene and P. G. M. Wuts, John Wiley & Sons, Inc., New York, 1991); OH-groups to azido-groups: J. March, *Advanced Organic Chemistry-Reaction Mechanisms, and Structure*, 3rd Edn. John Wiley & Sons, New York, 380, (1985), and references cited therein; H. H. Baer, *Pure Appl. Chem.*, 61(7) (1989) 1217–1234, and references cited therein; OH-groups to aminogroups via azides or other routes (March, *Advanced Organic Chemistry-Reaction Mechanisms, and Structure*, 3rd Edn. John Wiley & Sons, New York, 1106, 798–800 (1985), and references cited therein; H. H. Baer, *Pure Appl. Chem.*, 61(7) (1989) 1217–1234, and references cited therein).

The 4,6-O-acetal function is then reductively opened to yield either the function $R_6$ in the case when $R_6$ is an ether, or the intermediates F1, F2 or F3 with a hydroxy function on position 6 (reductive opening of acetals, see Garegg P J and Hultberg H, *Carbohydr. Res.* 1981, 93, c10–11; Garegg P J, Hultberg H, and Wallin S, *Carbohydr. Res.* 1982, 108, 97–101; Liptak A, Jodal I, Nanasi P, *Carbohydr. Res.* 1975, 44, 1–11; Baker D C, Horton D, Tindall C G, *Methods in Carbohydr. Chem.*, 1976 Vol 6, 3–6; Mikami T, Asano H, Mitsunobu O, *Chem. Lett.* 1987, 10, 2033–2036; Ek M, Garegg P J, Hultberg H, Oscarsson S, *J. Carbohydr. Chem.* 1983,2, 305–311; Hunter R, Bartels B, Michael J P, *Tetrahedron Lett.* 1991, 32, 1095–1098; Rao S P, Grindley T B, *Carbohydr. Res.* 1991, 218, 83–93; Hunter,R. Bartels,B. *J. Chem. Soc. Chem. Commun.* 1991, 2887–2888).

For example, the intermediates of type D1, D2 or D3 are treated with sodium cyanoborohydride and chlorotrimethylsilane in acetonitrile, (R. Johansson and B.Samuelsson, *J. Chem. Soc. Perkin Trans.* 1, 1984, 2371–2374) or borane-trimethylamine complex and aluminium trichloride. The regiochemical outcome of the reaction is often solvent-dependent (Ek M, Garegg P J, Hultberg H, Oscarsson S, *J. Carbohydr. Chem.* 1983, 2, 305–311).

The aldehyde intermediates of type G1, G2 or G3

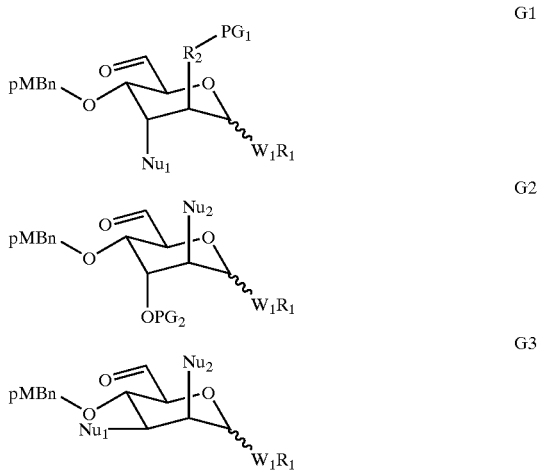

are obtained by oxidation of the corresponding 6-alcohol intermediates of type D1, D2 or D3, preferably by the Swern procedure. (Mancuso A J, Swern D, *Synthesis*, 1981, 165–185; Tidwell T, *Synthesis*, 1990, 857–870; for other oxidation methods, see A. H. Haines, 1988, *Methods for the Oxidation of Organic Compounds*, Chapter 2, Academic Press, San Diego, and references cited therein).

In the next step a carbon nucleophile is added to the aldehyde function of the intermediates of type G1, G2 or G3. Preferably, a suitably protected alkyllithium or aryllithium reagent or a gringard reagent is added to the aldehyde in an ether or hydrocarbon solvent to produce the secondary alcohols H1, H2 and H3:

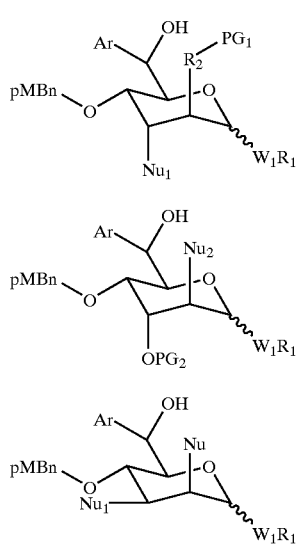

For reactions of aldehydes with organolithium and organomagnesium compounds, see J. March, *Advanced Organic Chemistry-Reaction Mechanisms, and Structure*, 3rd Edn. John Wiley & Sons, New York, 347 (1985), and references cited therein.

For reactions of aldehydes with organolithium and organomagnesium and other carbon nucleophils, see Evans D A, *Aldrichim. Acta*, 1982, 15, 23, and references cited therein.

For specific examples on the use and preparation of arylsubstituted phenyllithium and grignard reagents, see Ames M M, Castagnoli Jr. N, *J. Labelled Compd.*, 1974,10 (2), 195–205; DE 3807910 A1; Mills R J, Snieckus V, *Polynucl. Aromat. Hydrocarbons*, [*Pap. Int. Symp.*], 8th, Meeting 1983, 913–24. Edited by: Cooke M and Dennis A J, Battelle Press 1985: Columbus, Ohio; Iriye R, Furukawa K, Nishida R, Kim C, Fukami H, *Biosci. Biotechnol. Biochem.* 1992, 56(11), 1773–5; Comber M F, Sargent M V U, *J. Chem. Soc., Chem. Commun.*, 1991, (3), 190–2; Hirai T, Yoshizawa A, Nishiyama I, Fukumasa M, Shiratori N, Yokoyama A, EBP 341686 A2; Leeson P D, Emmett J C, Shah V P, Showell G A, Novelli R, Prain H D, Benson M G, Ellis D, Pearce N J, Underwood A H, *J. Med. Chem.* 1989, 32(2), 320–36); Meltzer P C, Liang A Y, Brownell A L, Elmaleh D R, Madras B K, *J. Med. Chem.*, 36(7), 855–62; Willard A K, Novello F C, Hoffman W F, Cragoe Jr E J. U.S. Pat. No. 4,459,423.

For substituted phenyllithium reagents that can be further elaborated into heterocyclic compounds, see: Lang H J, Muschaweck R, AU 514406 B2; Lang H J, Muschaweck R, Hropot M, HU 19761; Lang H J, Muschaweck R, Hropot M, DE 2737195.

For heteroaromatic aryllithiums and grignard reagents, see: Yang Y, Martin A R, Nelson D L, Regan J, *Heterocycles*, 1992, 34(6), 1169–75.

For examples of other organometallic reagents for the stereoselective synthesis of secondary alcohols from aldehydes:

Homoallyl alcohols with crotylmolybdenum complexes: Faller J W, John J A, Mazzieri M R, *Tetrahedron Lett.* 1989, 30, 1769–1772.

Homoallyl alcohols with titanium complexes: Riediker M, Duthaler R O, *Angew. Chem. Int. Ed. Engl.*, 1989, 28, 494–495.

3-Pyrollyl alcohols with silyl protected 3-lithiopyrrole: Bray B L, Mathies P H, Naef R, Solas D R, Tidwell T T, Artis D R, Muchowski J M, *J. Org. Chem.*, 1990, 55, 6317–6328.

Allylic alcohols with E-vinylalane: A P Kozikowski and Jiang-Ping Wu, *Tetrahedron Lett.* 1990, 30, 4309–4312 and references cited therein.

Trans-allylic diols with vinyistannanes: Corey E J, Wollenberg R H, *J. Org. Chem.*, 1975, 40, 2265–2266.

Pyrrolidine carbinols with α-lithio pyrrolidine amidines: Sanner M A, *Tetrahedron Lett.* 1989, 30, 1909–1912.

Organozinc reagents: Furstner A, *Synthesis*, 1989, 571–590, and references cited therein.

Thereafter, the substituent on the 3-position ($Nu_1$ or $OPG_1$) is transformed into a nucleophile in order to install the negatively charged functionality $Z_1$-D-$R_3$.

The secondary 6-alcohols H1, H2 and H3 are first protected, (*Protective Groups in Organic Synthesis*, Editors T. W. Greene and P. G. M. Wuts, John Wiley & Sons, Inc., New York, 1991) or transformed to amino functions in the cases where $X_1$-$R_6$ forms a peptide functionality (OH-groups to aminogroups via azides or other routes: See for examples March, *Advanced Organic Chemistry-Reaction Mechanisms, and Structure*, 3rd Edn. John Wiley & Sons, New York, 1106, 798–800 (1985), and references cited therein; H. H. Baer, *Pure Appl. Chem.*, 61(7) (1989) 1217–1234, and references cited therein).

For peptide synthesis, see Gross and Meienhofer, *The Peptides*, 3 vol., Academic Press, New York,1979–1981; Grant G A et al., *Synthetic Peptides, A Users Guide*, 1992, W. A. Freeman and Company, New York, and references cited therein).

The 3-position is deprotected to an alcohol, thiol or amine intermediate I1, I2 or I3

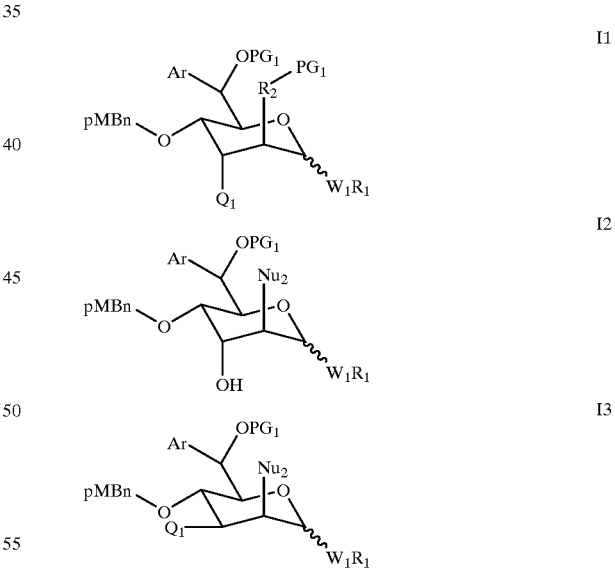

(*Protective Groups in Organic Synthesis*, Editors T. W. Greene and P. G. M. Wuts, John Wiley & Sons, Inc., New York, 1991, and references cited therein).

For example, treatment of I1, where $R_2$-$PG_1$ is a combination of ether functions and $Q_1$ is azide, with gaseous hydrogen sulphide in pyridine and water (T. Adashi, Y. Yamada, I. Inoue and M. Saneyoshi, *Synthesis*, 1977, 45). For other methods of azide reductions, see Poopeiko N E, Pricota T I, Mikhailopulo I A, *Synlett*, 1991, 5, 342; Samano M C, Robins M J, *Tetrahedron Lett.* 1991, 32, 6293–6296;

Rakotomanomana N, Lacombe J-M, Pavia A, *Carbohydr. Res.*, 1990, 197, 318–323; Malik A A, Preston S B, Archibald T G, Cohen M P, Baum K, *Synthesis*, 1989, 450–451; Maiti S, Spevak P, Reddy N, *Synt. Commun.* 1988, 18, 1201–1206; Bayley H, Standring D N, Knowles J R, *Tetrahedron Lett.*, 1978, 39, 3633–3634).

The intermediates I1, I2 or I3 are sulphated with sulphur trioxide-pyridine or -triethylamine complex to obtain the intermediates J2, J4 and J6

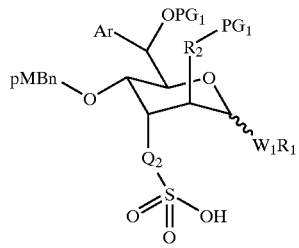
J2

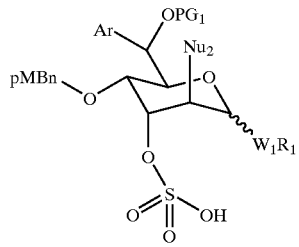
J4

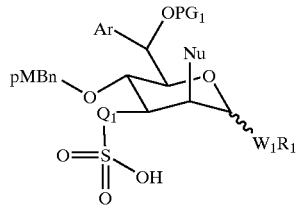
J6

(see, for example J. Basten, G. Jaurand, B. Olde-Hanter, M. Petitou and C. A. A. van Boeckel, *Bioorg. Med. Chem. Lett*, 1992, 2(9), 901–904 and references cited therein; J.Basten, G. Jaurand, B. Olde-Hanter, P. Duchaussoy, M. Petitou and C. A. A. van Boeckel, *Bioorg. Med. Chem. Lett*, 1992, 2(9), 905–910, and references cited therein; Böcker,T. Lindhorst,T K. Thiem,J. Vill, V. *Carbohydr. Res.* 1992, 230, 245–256) or coupled to form the phosphoester intermediates J1, J3 and J5

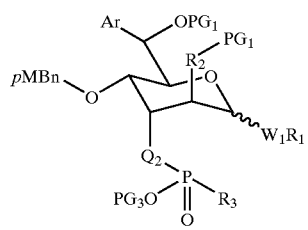
J1

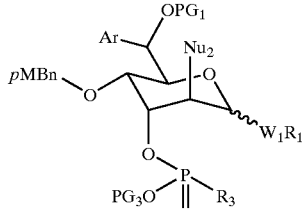
J3

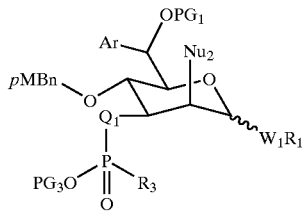
J5

Since the phosphorus-nitrogen bond is known to be acid labile, the intermediates leading to phosphodiester endproducts are preferred (M. Selim and T. N. Thanh, *C. R. Seances Acad. Sci*, 1960, 250, 2377).

For example, the alcohol intermediates I1, I2 or I3 are treated with 2,2,2-trichloroethyl 2-chlorophenyl phosphochloridate in chloroform and pyridine to form the phosphate triesters. The 2,2,2-trichloroethyl group is removed by treatment with zinc powder and the resulting phosphate diester is activated with 3-nitro-1-(2,4,6-triisopropylbenzenesulphonyl)-1,2,4-triazol e and coupled with the alcohol $R_3$—OH to form the intermediates J1, J3 and J5. The 2-chlorophenyl group is removed by treatment with pyridine-2-aldoxime and N,N,N,N-tetramethylguanidine in moist pyridine (see for example P. J. Garegg, R. Johansson, I. Lindh and B. Samuelsson, *Carbohydr. Res.* 1986, 150, 285–289).

Alternatively, by the phosphite triester approach, alcohol intermediates I1, I2 or I3 are treated with phenyl chloro-N,N-diisopropylphosphoramidite in acetonitrile to form carbohydrate phosphoamidites. After purification by chromatography, these are exposed to an alcohol $R_3$—OH in the presence of a mild acid, such as pyridinium p-toluenesulphonate and treated with tert-butyl hydroperoxide to form phosphate diesters J1, J3 and J5 ($PG_3$=H) (H-N. Caro, M. Martín-Lomas and M. Bernabé, *Carbohydr. Res.* 1993, 240, 119–131, and references cited therein).

For a review on phospodiesters in DNA synthesis, see Narang S, *Tetrahedron*, 1983, 39, 1–22 and D. W. Hutchinson, 1991, Chapter 3 in *Chemistry of Nucleosides and Nucleotides*, vol 2, ed. B. Townsend, Plenum Press, New York, and references cited therein. For other examples on carbohydrate phosphodiester synthesis, see for example Ichikawa Y, Sim M M, Wong C H, *J. Org. Chem.* 1992, 57, 2943–2946 and Schmidt R R, Braun H, Jung K-H, *Tetrahedron Lett.* 1992, 33, 1585–1588. For synthesis of modified phosphodiester linkages, See R. S. Varma, 1993, *Synlett*, 621–636, and references cited therein.

To obtain arylphosphonic acid esters and amides J1, J3 and J5, where $R_3$ is an alkyl or aromatic group the arylphosphonic acid $R_3$—$PO_3H_2$ is coupled to the alcohol intermediates I1, I2 or I3, for example, with a carbodiimide reagent, or treatment of the phosphonic dichlorides with the alcohol intermediates I1, I2 or I3 in pyridine (T. H. Siddal III, and C. A. Prohaska, *J. Am. Chem.* 1962, 84, 3467).

The alkylphosphonic triesters are formed from trialkyphosphites and alkyl halides by the Arbuzov reaction (Arbuzov, *Pure Appl. Chem.* 1964, 9, 307–335, J. March, *Advanced Organic Chemistry-Reaction Mechanisms, and Structure*, 3rd Edn. John Wiley & Sons, New York, 347 (1985), and references cited therein).

For the preparation of arylphosphonic triesters via phosphorus trichloride, see for example: K. Sasse, *Methoden der Organichen Chemie* (Houben-Weyl), 4th ed., Vol. 12/1, Georg Thieme, Stuttgart, 1963, p. 314 and p. 392 and references cited therein; G. M. Kosolapoff, *Org. React.* 6, 273 (1951), and references cited therein; L. D. Freedman and G. O. Doak, *Chem. Rev.* 1957, 57, 479, and references cited therein.

For the preparation of arylphosphonic triesters via organomagnesium or organolithium reagents, see for example: K. Sasse, *Methoden der Organichen Chemie* (Houben-Weyl), 4th ed., Vol. 12/1, Georg Thieme, Stuttgart, 1963, p. 372, and references cited therein; G. M. Kosolapoff, *Org. React.* 6, 273 (1951), and references cited therein.

Intermediates J1, J2, J3, J4, J5 and J6 are deprotected to form the final products (*Protective Groups in Organic Synthesis*, Editors T. W. Greene and P. G. M. Wuts, John Wiley & Sons, Inc., New York, 1991, and references cited therein) and transformed to their sodium or potassium salts.

It is justified to assume that the compounds described above are capable of interacting with sites in PapD and other periplasmic chaperones. In order to establish that this is really the case, assays like those described in the examples should be performed.

Thus, a preferred compound of the invention is a compound as described above, which causes a prevention, inhibition or enhancement of the binding of G1'-19'WT to PapD, and/or causes a prevention, inhibition or enhancement of the binding of the fusion peptide MBP-G1'-140' to PapD and/or causes a prevention, inhibition or enhancement of the binding of the peptide G125'-140' (which have the sequence SEQ ID NO: 20) to PapD and/or is capable of inhibiting the restoration of the PapD-PapG complex normally caused by the addition of access PapD.

The assay used to establish that a substance exhibits one of the above effects is preferably one of the assays described in the examples herein. Of course, also other assays as those discussed above in the methods of the invention may be utilized in order to establish that the compound actually is capable of inhibiting pilus assembly.

One important point which should be taken into consideration when setting up an assay, is the role the chaperones are playing in vivo. They bind to the pilus subunits already during the transport through the cell membrane of the subunits and it is therefore assumed, that the pilus subunits are more or less unfolded (i.e. not in their final folded conformation) when they bind to the chaperone. It has been observed by the inventors that the kinetics of binding between completely folded pilus subunits (or analogues thereof) and the chaperone PapD is a slow process, although it is known that the process of pilus assembly is relatively fast in vivo. In order to speed up the rate of assembly of the chaperone/pilus subunit complex in vitro it is contemplated that more or less severe denaturing conditions could be imposed on the pilus subunits (or the analogues thereof) prior to the assay. Such denaturing could be obtained by subjecting the pilus subunits to physical stress (e.g. to elevated temperature, pressure changes, radiation etc.) or to changes in the chemical environment (e.g. changes in ionic strength, changes in pH, or the addition of denaturing compounds or disulphide reducing compounds.

The expression "denaturing compound" refers to a compound which when present as one of the solutes in a liquid phase comprising polypeptide molecules may destabilize folded states of the polypeptide molecules leading to partial or complete unfolding of the polypeptide chains. The denaturing effect exerted by a denaturing compound increases with increasing concentration of the denaturing compound in the solution, but may furthermore be enhanced or moderated due to the presence of other solutes in the solution, or by changes in physical parameters, e.g. temperature or pressure.

As examples of suitable denaturing compounds to be used may be mentioned urea, guanidine-HCl, di-$C_{1-6}$alkylformamides such as dimethylformamide and di-$C_{1-6}$-alkylsulphones.

Examples of disulphide reducing compounds are glutathionyl-2-thiopyridyl disulphide, 2-thiocholyl-2-thiopyridyl disulphide, 2-mercaptoethanol-2-thiopyridyl disulphide and mercaptoacetate-2-thiopyridyl disulphide.

A set of observations confirm the assumption that the pilus subunits are more or less unfolded while bound to the chaperone: As described in Kuehn et al., 1991, it is possible to restore the PapD-PapG complex after denaturation by adding access PapD. Further, preliminary results obtained by capillary electrophoresis show that denaturation of the fusion protein MBP-G1'-140' gives a single form of the fusion protein, whereas two forms of the fusion protein are observed in capillary electrophoresis before denaturation, one major which is unable to interact with PapD and one minor which is capable of interacting with PapD. It is therefore contemplated that the denatured fusion protein may serve as a superior substrate in the different competitive assays described herein as does the non-denatured form of the fusion protein.

Thus, in a preferred embodiment of the invention, the compound of the invention causes a prevention, inhibition or enhancement of the binding of a denatured form of either a pilus subunit or an analogue thereof to PapD, and/or causes a prevention, inhibition or enhancement of the binding of a denatured form of MBP-G1'-140' to PapD and/or causes a prevention, inhibition or enhancement of the binding of a denatured form of G125'-140' to PapD.

As will appear from the examples, compounds which should be capable of interacting with PapD and other chaperones have already been identified and synthesized. These compounds which are all pyranosides are also an important part of the invention:

Ethyl 2,3-O-Dibenzoyl-4-O-benzyl-1-thio-β-D-glucohexopyrano-side;

Ethyl 6-O-acetyl-2,3-O-dibenzoyl-4-O-benzyl-1-thio-β-D-gluco-hexopyranoside;

Methylglycolyl 6-O-acetyl-2,3-O-dibenzoyl-4-O-benzyl-β-D-glucohexopyranoside;

2-(Hydroxy)ethyl 4-O-benzyl-β-D-glucopyranoside;

Sodium glycolyl 4-O-benzyl-β-D-glucohexopyranoside;

Methyl 2-O-ethyl-4,6-O-(4'-methoxy)phenylmethylene-α-D-mannohexopyranoside;

Methyl 2-O-ethyl-3-O-dimethyl-t-butylsilyl-4,6-O-(4'-methoxy)phenylmethylene-β-D-mannohexopyranoside;

Methyl 2-O-ethyl-3-O-dimethyl-t-butylsilyl-4,-O-(4'-methoxy)-benzyl-α-D-mannohexopyranoside;

methyl 2-O-ethyl-3-O-dimethyl-t-butylsilyl-6-O-(4'-methoxy)-benzyl-α-D-mannohexopyranoside;

Methyl 2-O-ethyl-3-O-dimethyl-t-butylsilyl-4,—O-(4'-methoxy)-benzyl-6(S)-phenyl-α-D-mannohexopyranoside;

Methyl 2,3-anhydro-4,6-O-p-methoxybenzylidene-α-D-mannopyranoside;

Methyl 3-azido-4,6-O-p-methoxybenzylidene-α-D-altropyranoside;

Methyl 3-azido-2-O-ethyl-4,6-O-p-methoxybenzylidene-α-D-altropyranoside;
Methyl 3-azido-3-deoxy-2-O-ethyl-4-O-p-methoxybenzyl-α-D-altro-pyranosid;
Methyl 3-azido-6-O-benzoyl-3-deoxy-2-O-ethyl-4-O-p-methoxy-benzyl-α-D-altropyranoside;
Methyl 6-O-benzoyl-3-deoxy-2-O-ethyl-4-O-p-methoxybenzyl-3-sulfamino-α-D-altropyranoside sodium salt;
Methyl 6-O-benzoyl-3-deoxy-2-O-ethyl-3-sulfamino-α-D-altropyranoside ammonium salt;
Methyl 3-azido-6-O-pivaloyl-3-deoxy-2-O-ethyl-4-O-p-methoxy-benzyl-α-D-altropyranoside;
Methyl 6-O-pivaloyl-3-deoxy-2-O-ethyl-4-O-p-methoxybenzyl-3-sulfamino-α-D-altropyranoside sodium salt;
Methyl 6-O-pivaloyl-3-deoxy-2-O-ethyl-3-sulfamino-α-D-altro-pyranoside ammonium salt;
Methyl 6-O-pivaloyl-3-deoxy-2-O-ethyl-4-O-p-methoxybenzyl-3-tbutyloxamido-α-D-altropyranoside;
Methyl 6-O-pivaloyl-3-deoxy-2-O-ethyl-3-oxamido-α-D-altro-pyranoside ammonium salt;
Methyl 3-azido-6-O-pyrrol-3'-ylcarboxyl-3-deoxy-2-O-ethyl-4-O-p-methoxybenzyl-α-D-altropyranoside; and
Methyl 6-O-pyrrol-3'-ylcarboxyl-3-deoxy-2-O-ethyl-3-sulfamino-α-D-altropyranoside ammonium salt.

Other compounds are of course also possible as interactors with sites in chaperones. As is evident from example 7, modified peptides also may prove to be useful in the methods of the invention.

As will be clear from the above, the identification of a site in the chaperone which may be affected so as to interfere with pilus assembly is a critical starting point in the methods described herein for the identification, isolation and synthesis of compounds capable of interacting with periplasmic chaperones.

Thus, the invention also relates to a method for identifying a binding site in a molecular chaperone, comprising
co-crystallizing the periplasmic molecular chaperone or an analogue thereof with a ligand binding to the periplasmic molecular chaperone or the analogue thereof,
resolving the three-dimensional structure of the chaperone/ligand interaction, thereby resolving the three-dimensional structure of the periplasmic molecular chaperone or the analogue thereof when binding to the ligand,
determining the site-point(s) involved in the intermolecular interaction between the periplasmic molecular chaperone or the analogue thereof and the ligand, and
identifying the thus determined site-point(s) of the periplasmic molecular chaperone or the analogue thereof as a binding site in the periplasmic molecular chaperone or the analogue thereof.

By the term "ligand" as used herein, is meant a substance which exhibit binding to a host or receptor molecule (in this connection a chaperone). The binding is not a non-specific interaction, which means that a binding motif between the ligand and the host or receptor molecule exists. In other words, when bringing a sample of the ligand and a sample of the host or receptor molecule in contact with each other the complexes formed between the ligand and the host or receptor molecule will substantially all reflect the same intermolecular interactions.

As mentioned above one embodiment of the invention is to administer a substance which is capable of preventing, inhibiting or enhancing binding between pilus subunits and molecular chaperones.

Accordingly the invention relates to a pharmaceutical composition, comprising, as an active compound, a substance capable of interacting with at least one type of periplasmic molecular chaperone which binds pilus subunits during transport of these pilus subunits through the periplasmic space and/or during the process of assembly of the intact pilus, in such a manner that binding of pilus subunits to the periplasmic molecular chaperone is prevented, inhibited or enhanced, in combination with at least one pharmaceutically acceptable carrier or excipient. Preferably such a substance is a substance according to the invention or a substance identified/designed according to the methods of the invention.

The pharmaceuticals and pharmaceuticals discussed herein are thus, according to the invention, for the treatment and/or prophylaxis of the same conditions as those discussed when disclosing the method of treatment of the invention and caused by the same bacterial species.

Therefore, a pharmaceutical composition, comprising, as an active compound, a substance used in the therapeutic methods of the invention, a substance according to the invention or a substance identified according to the methods of the invention, in combination with at least one pharmaceutically acceptable carrier or excipient, is a part of the invention.

Such pharmaceutical compositions of the invention could also comprise at least one additional pharmaceutical substance, which i.a. could enhance the pharmaceutical effects exerted by the substance of the invention or the substance identified according to the invention.

Additional pharmaceutical substances could be steroid hormones, disinfectants, anti-pyrretics, etc. Preferably such an additional substance could be an antibacterial agent.

Such an anti-bacterial agent could conveniently be selected from the group consisting of penicillins, cephalosporins, aminoglycosides, sulfonamides, tetracyclines, chloramphenicol, polymyxins, antimycobacterial drugs and urinary antiseptics.

The invention also relates to a substance employed in the methods of the invention as well as a substance of the invention and a substance idexnified according to the methods of the invention for use as a pharmaceutical. It is preferred that the pharmaceutical is for antibacterial treatment and/or prophylaxis, especially treatment and/or prophylaxis of diseases caused by tissue-adhering pilus forming bacteria, apd it is especially preferred that the pharmaceutical is for treatment and/or prophylaxis of urinary tract infection.

Finally, the invention relates to the use of a substance employed in the methods of the invention as well as a substance of the invention and of a substance identified according to the methods of the invention for the preparation of a pharmaceutical composition for the treatment and/or prophylaxis of bacterial infection.

LEGENDS TO FIGURES

The patent or application file contains at least one drawing executed in color. Copies of this patent or patent application publication with color drawing(s) will be provided by the Office upon request and payment of the necessary fee.

FIG. 1: PapD binds to pilus subunit-related peptides coated in ELISA microtiter plates and in solution. A and B: The peptides from Table 1 were coated on microtiter wells and tested for their ability to bind to PapD in an ELISA assay described in example 2. Water insoluble peptides were dissolved in 2.5% acetic acid (AA) which had no effect on the binding of G1'-19'WT to PapD in this assay. Each group represents the average of duplicate wells.

FIG. 2: Binding of pilus subunit-related peptides provides protection against enzymatic proteolysis and blocks binding of PapD to PapG.

A Upper: PapD (15 µg) was incubated with PBS (lane D) or with 1.5 µg trypsin (lane D and Tr) at 37° C. for 20 minutes and applied to 20% SDS-PAGE. Coomassie blue stained bands corresponding to full length PapD (PapD), trypsin (Tr, the $NH_2$-terminal fragment of PapD (N), and the COOH-terminal fragment of PapD starting at residue 100 (C) are indicated).

A Lower: The rate of trypsin cleavage of PapD decreased upon preincubation with the G1'-19'WT, G1'-16'WT or K1'-19'WT peptides, but the G2'-21'amide peptide had no effect. 50 µg of purified PapD was preincubated for 15 min at 25° C. with a 20-fold molar excess of G1'-19'WT, G1'-16'WT, K1'-19'WT or G2'-21'amide peptides (any trypsin cleavage sites in these peptides occur at their amino termini where they were predicted not to interfere with PapD), or an equivalent volume of water. Each sample was then incubated at 37° C. with 3.2 µg of trypsin. Aliquots were removed after 0, 5, 10, 20, 30 and 40 min and boiled in SDS-PAGE sample buffer to stop the digestion. The samples were applied to 15% SDS-PAGE gels and the amount of full-length PapD remaining was determined by densitometry of Coomassie blue stained bands corresponding to full-length PapD which are shown.

B: PapD incubated with the G1'-19'WT, G1'-16'WT, K1'-19'WT, and G2'-21'amide was added to reduced, denatured PapD-PapG and the amount of PapD-PapG complex restored in each sample was quantitated as described in example 2. The % inhibition represents the amount of the PapD-PapG complex restored with peptide-treated PapD compared to the amount of PapD-PapG complex restored with untreated PapD. The graph represent the average of 4 experiments. PapD and PapD-PapG complex were prepared as described in F. Lindberg et al, *J. Bacteriol.* 171, 6052 (1989) and S. J. Hultgren et al., Proc. Natl. Acad. Sci. USA 86, 4357 (1989).

Figure 3:
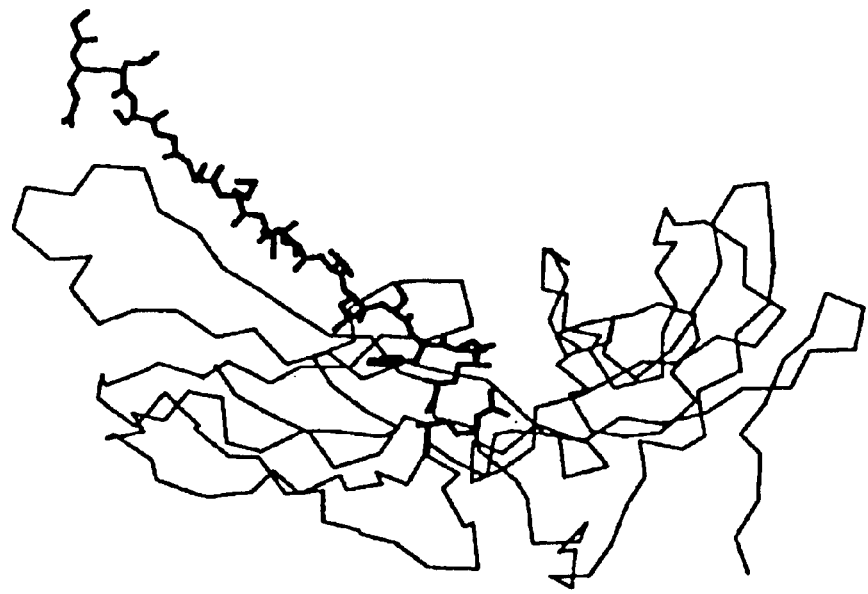
Figure 3:

FIG. 3 Stereoscopic view of the three-dimensional structure of PapD co-crystallized with the G1-19WT peptide determined to 3.0 Å resolution. The peptide is bound in an extended conformation along the G1 β strand in the cleft of PapD with the terminal carboxylate group forming hydrogen bonds with residues Arg-8 and Lys-112 of PapD.

Figure 4:
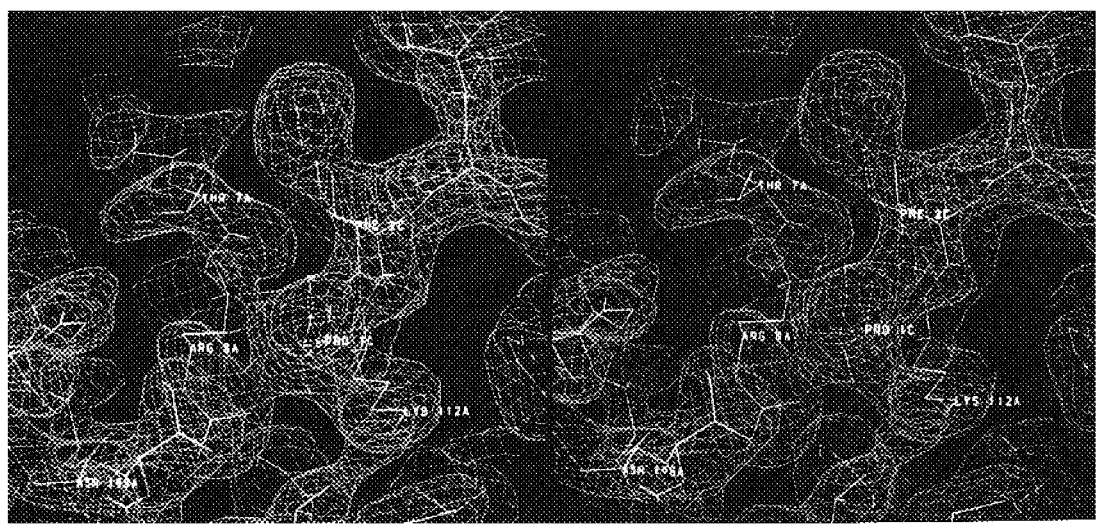

FIG. 4 Stereoscopic view of the 3.0 Å resolution electron density of the G1-19WT peptide COOH-terminus and neighbouring PapD residues, superimposed on the refined structure. The electron density map was calculated with coefficients (2|Fo|−|Fc|) and contoured at 1σ.

Figure 5:

FIG. 5 Stereoscopic view of a PapD-peptide complex showing its interaction with a twofold non-crystallographically related complex.

Figure 6:
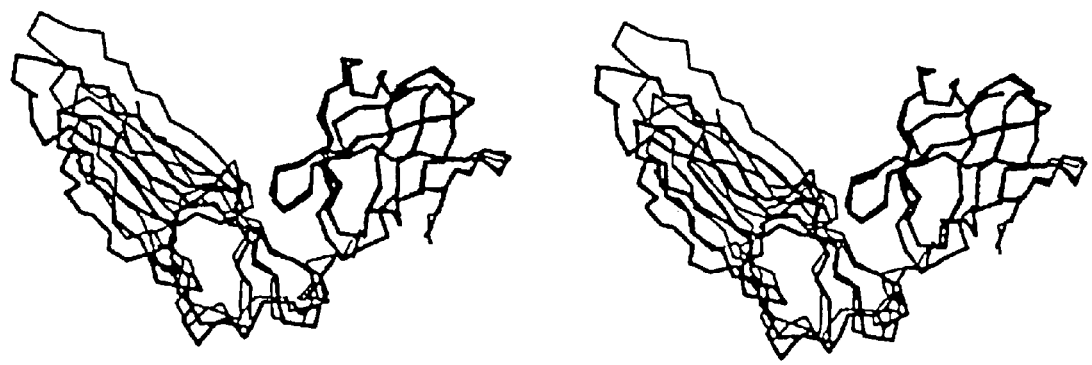

FIG. 6 Superposition of COOH-terminal domains of native PapD (thick lines) and complexed PapD (thin lines) showing the 13° difference in the hinge bend angle between the two structures. The structures were superimposed using the LSQ option in the graphics program O. The resulting rms for 98 Cα atoms of the COOH terminal domaip was 0.66Å.

Figure 7:
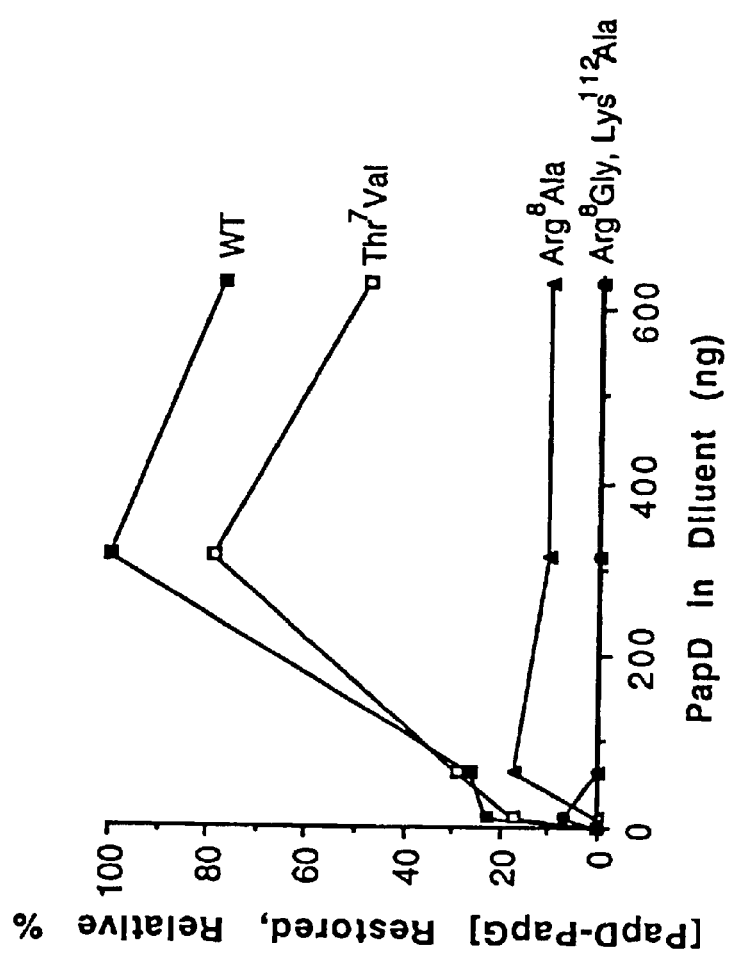

FIG. 7: Ability of PapD Arg-8, Lys-112 and Thr-7 mutants to bind PapG and restore the PapD-PapG complex in vitro. 0.4 µg of PapD-PapG complex was reduced and denatured as described in FIG. 2B. The denatured PapD-PapG complex was then diluted with 0–630 ng purified wild type (WT) or mutant PapD. The amount of PapD-PapG restored in the samples was determined as in FIG. 2B and was graphed as a percentage of the greatest amount of PapD-PapG restored. The values graphed represent the average of 3 experiments. Wild type and mutant PapD and the PapD-PapG complex were purified as described in F. Lindberg et al, J. Bacteriol. 171, 6052 (1989) and S. J. Hultgren et al., Proc. Natl. Acad. Sci. USA 86, 357 (1989).

Figure 8:
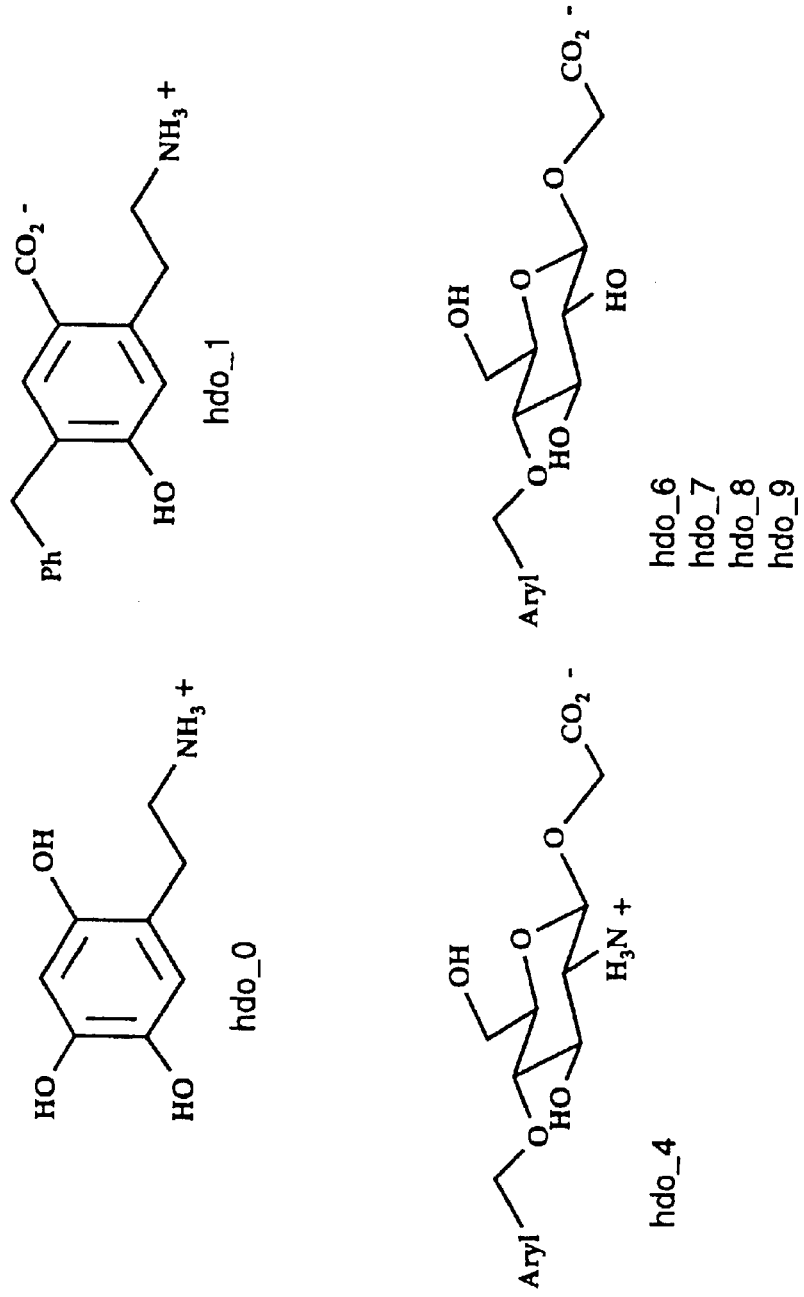

FIG. 8: 6-hydroxydopamine, hdo__0, and other members of the hdo family. hdo__0 Was used as starting-point for the construction of a family of compounds intended to bind to the binding-site of PapD. hdo__4: "Aryl" denotes 3,4-dihydroxyphenyl.

hdo__6: "Aryl" is a 3,4-dihydroxyphenyl group.

hdo__7: "Aryl" is a 3-hydroxyphenyl group.

hdo__8: "Aryl" is a 3-nitrophenyl group.

hdo__9: "Aryl" is a phenyl group.

Figure 9A:
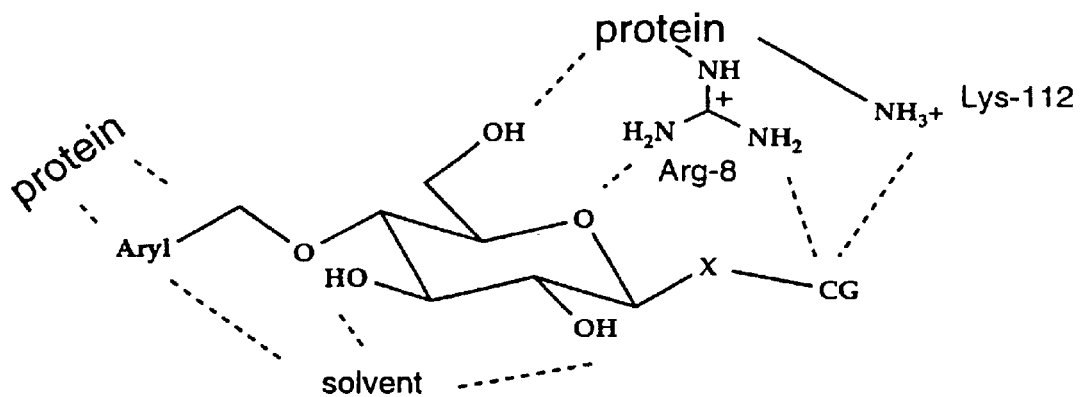
Figure 9B:
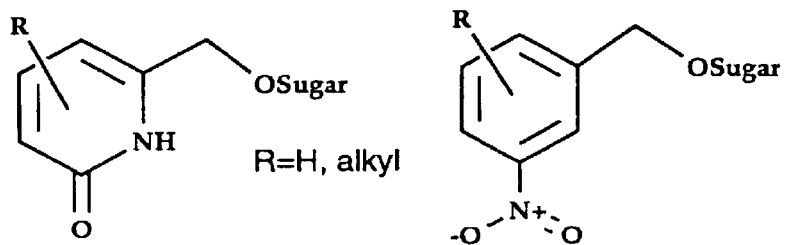
Figure 9C:
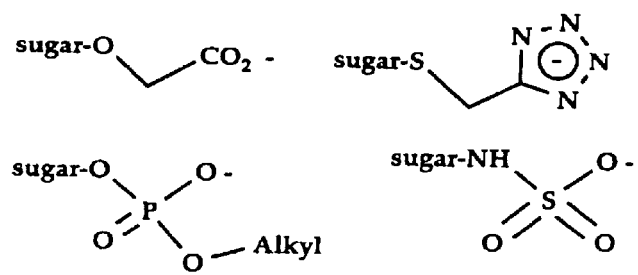

FIG. 9: The hdo family and its interaction with PapD.

A: "Aryl" is a phenyl group, a heteroaromatic ring, or a substituted phenyl group with polar substituents unsymmetrically in order to obtain hydrophobic contact with the protein on one side and interaction with solvent water on the other.

B: Examples of "Aryl" wherein R is hydrogen or alkyl; "X" is an oxygen atom, a sulphur atom, or a amino group; and CG" is a negatively charged group, such as a carboxyl group, a tetrazoyl group, a phosphate group, a phosphate ester or a sulphate group.

C: Examples of the group CG.

Figure 10:
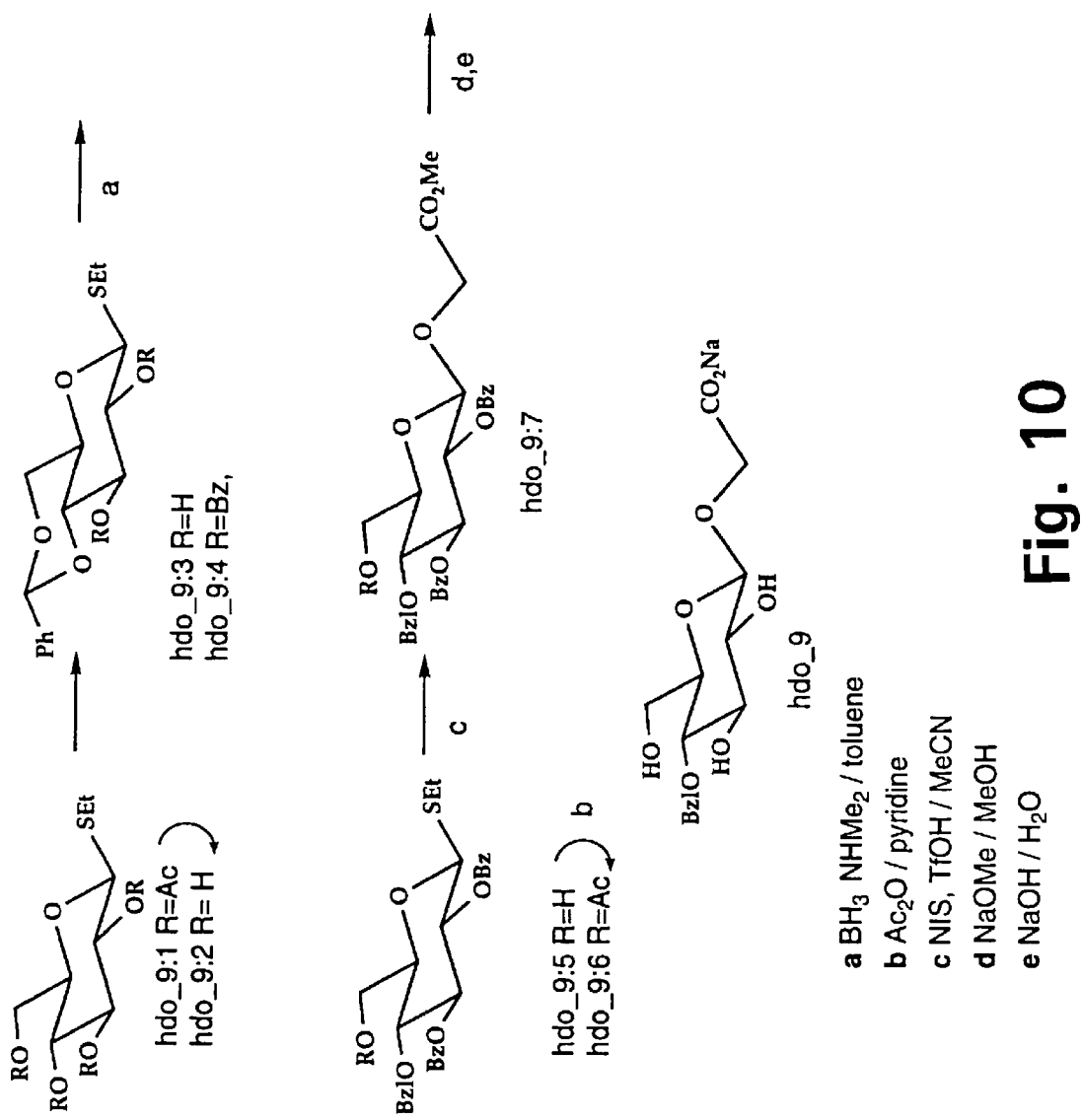

FIG. 10: General reaction scheme for the production of various members of the hdo family.

Figure 11:
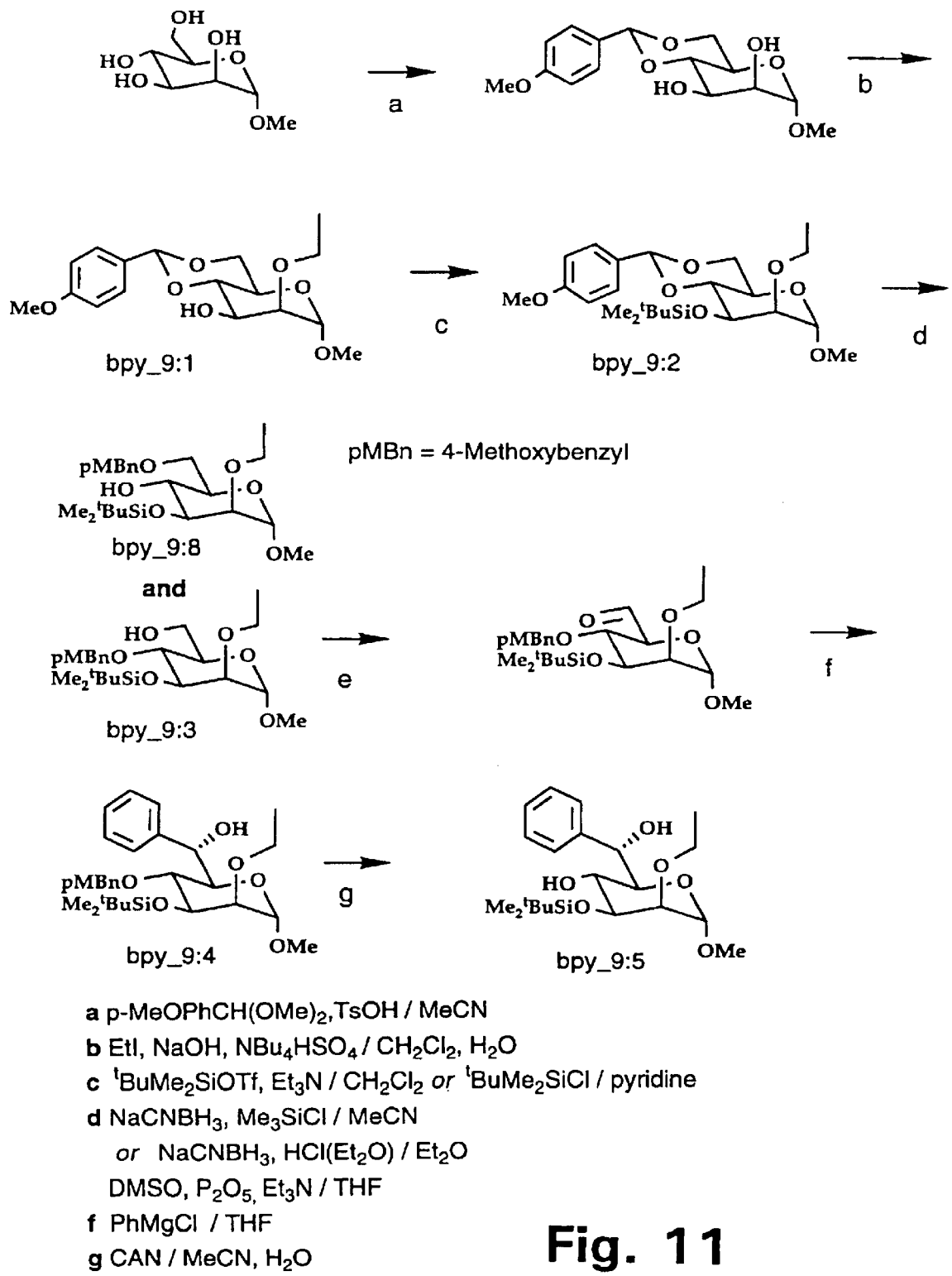

FIG. 11: General reaction scheme for the production of various members of the bpy family.

Figure 12:
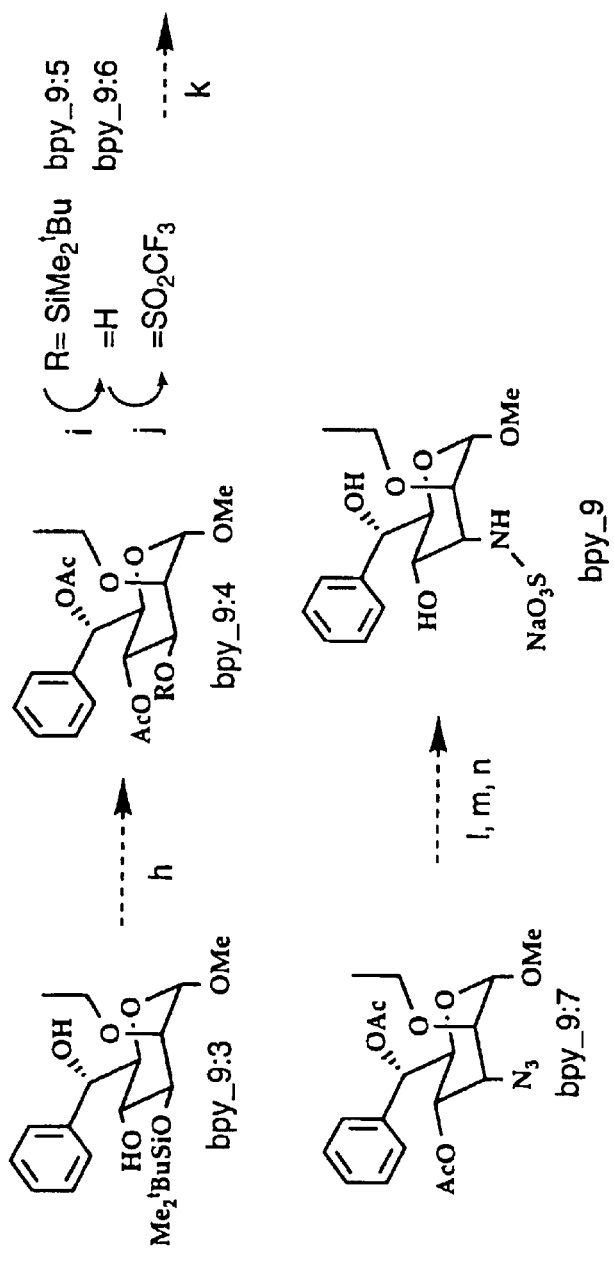

FIG. 12: General reaction scheme for the'production of various members of the bpy family.

Figure 13:
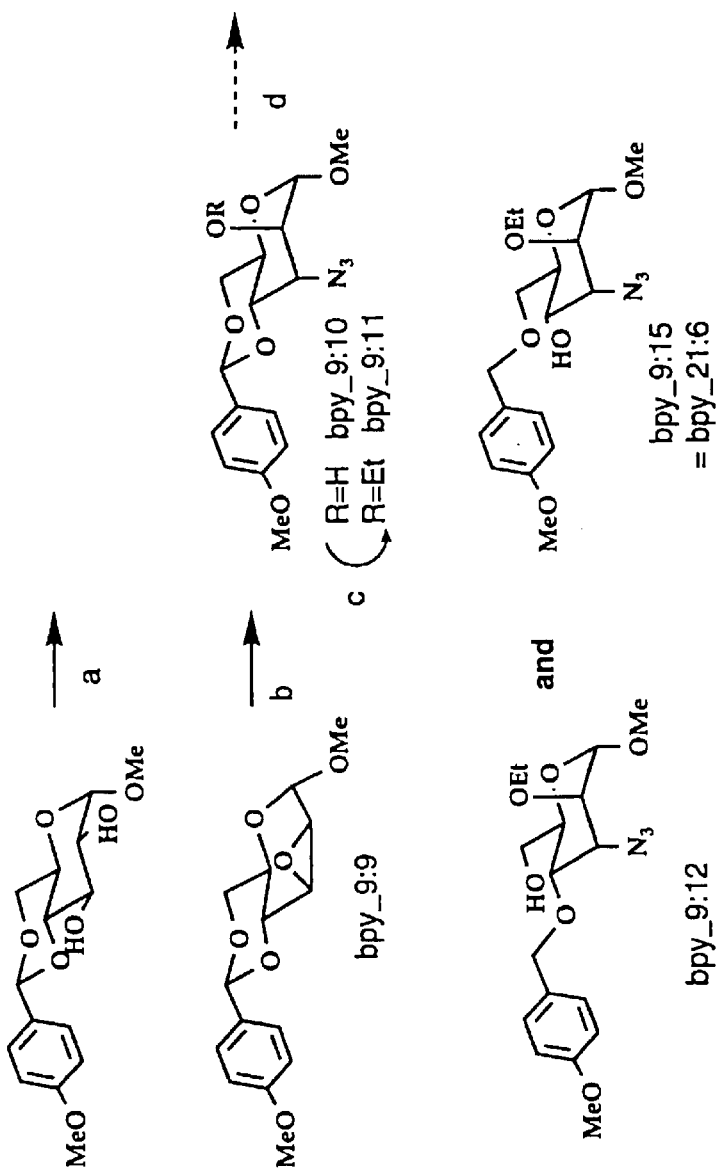

FIG. 13: General reaction scheme for the production of various members of the bpy family.

Figure 14:
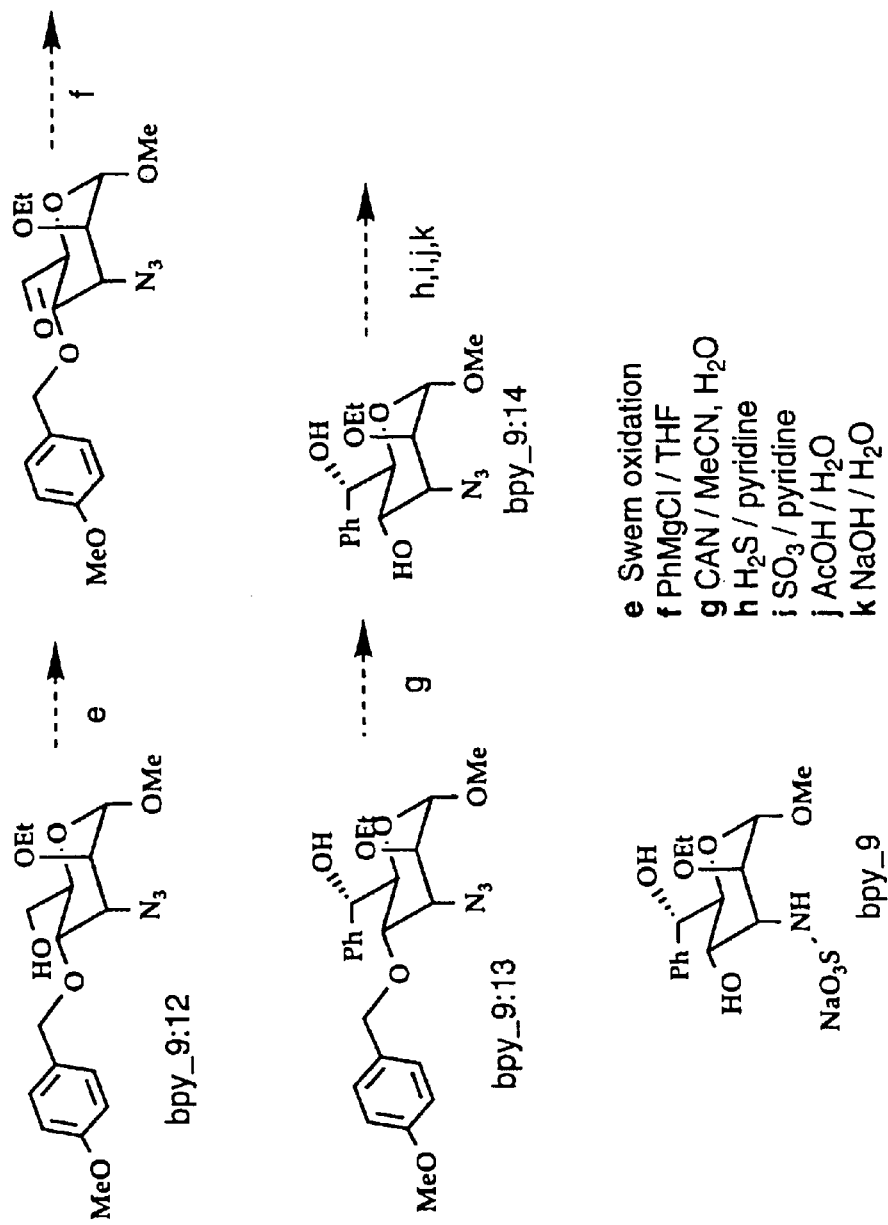

FIG. 14: General reaction scheme for the production of various members of the bpy family.

Figure 15:
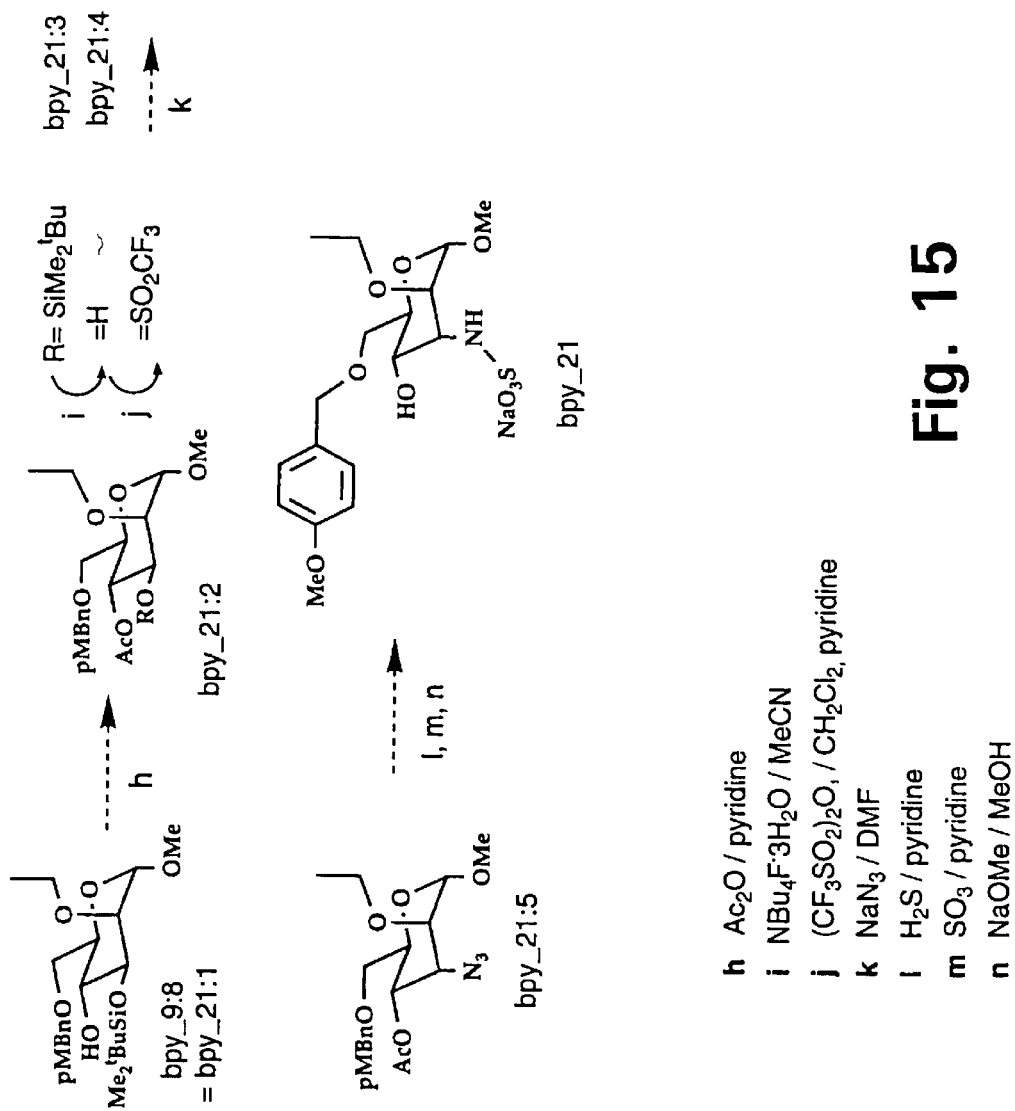

FIG. 15: General reaction scheme for the production of various members of the bpy family.

Figure 16:
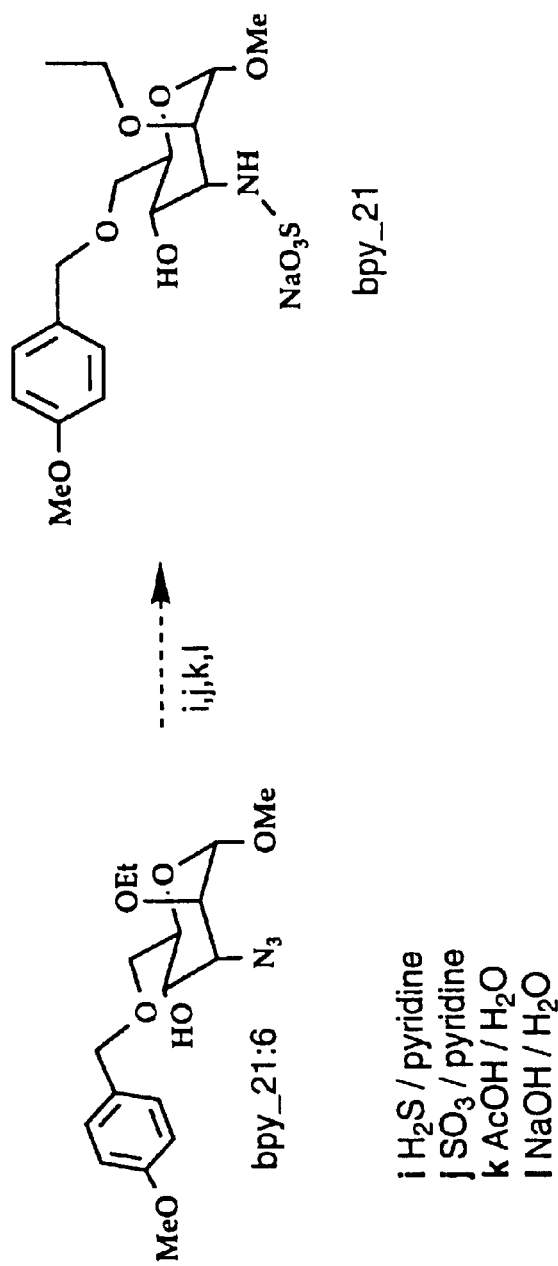

FIG. 16: General reaction scheme for the production of various members of the bpy family.

Figure 17:
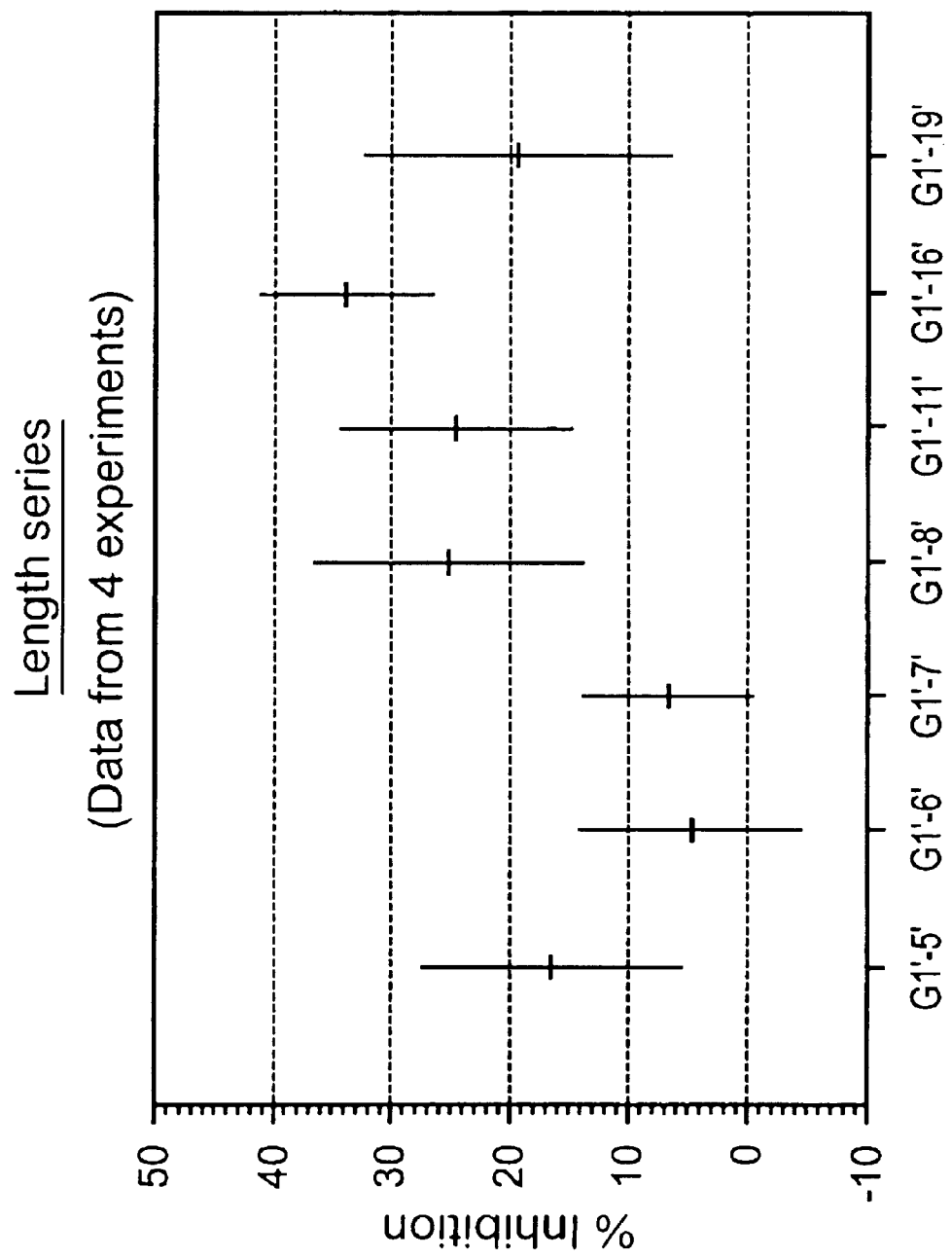

FIG. 17: Graph over the inhibitory effect of different lengths of C-terminal peptide fragments of PapG on the binding between PapD and the fusion protein MBP-G1'-140'.

The G1'-8' fragment exhibits a significantly higher inhibitive effect on the binding than does the shorter G1'-6' and G1'-7' fragments.

Figure 18:
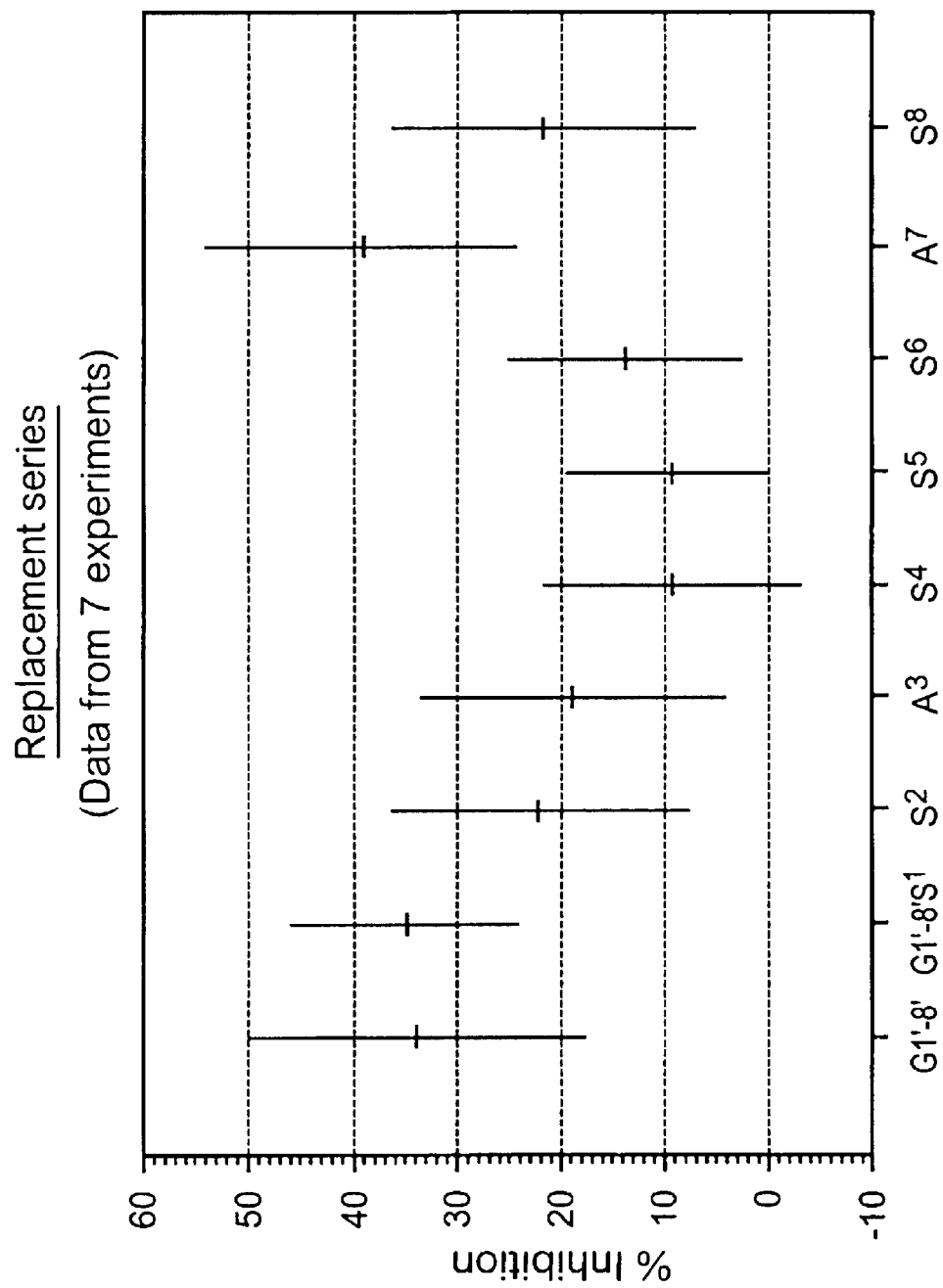

FIG. 18: Graph over the inhibitory effect of different analogues of G1'-8' (wherein the 8 amino acid residues one at a time has been replaced by serine (S) or Alanine (A)) on the binding between PapD and the fusion protein MBP-G1'-140'.

The effect of the replacements of residues 4', 5' and 6' in G1'-8' reveals that these residues are important in the interaction with PapD, as the replacement of these residues results in less inhibitory peptides.

Figure 19:
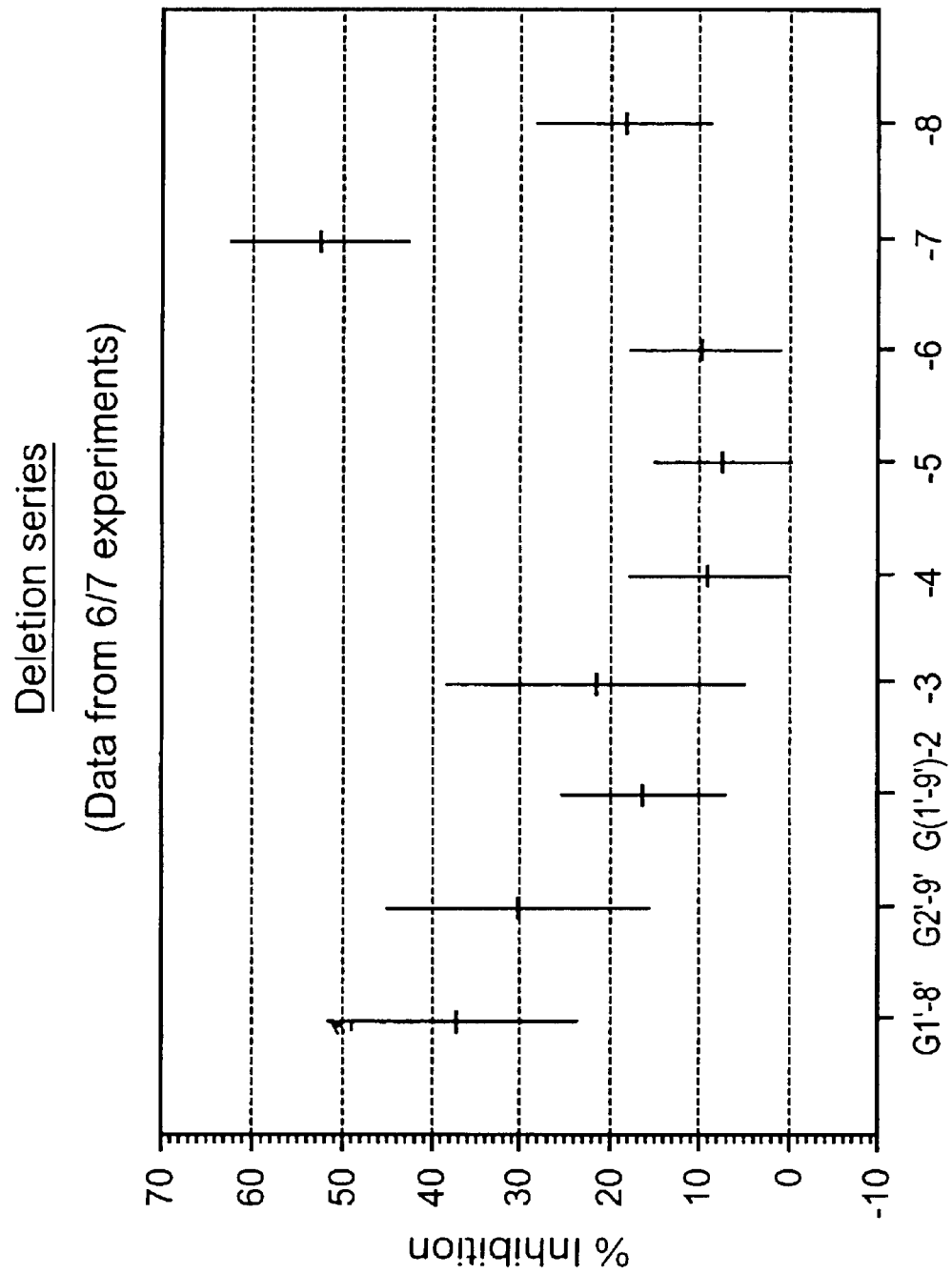

FIG. 19: Graph over the inhibitory effect of different analogues of G1'-8' (wherein the 8 amino acid residues one at a time has been deleted simultaneously with the addition of an N-terminal serine) on the binding between PapD and the fusion protein MBP-G1'-140'.

Also in this experiment, the significance of amino acid residues 4', 5', and 6' are emphasized, as the deletions at these positions leads to less inhibitory peptides.

Figure 20:
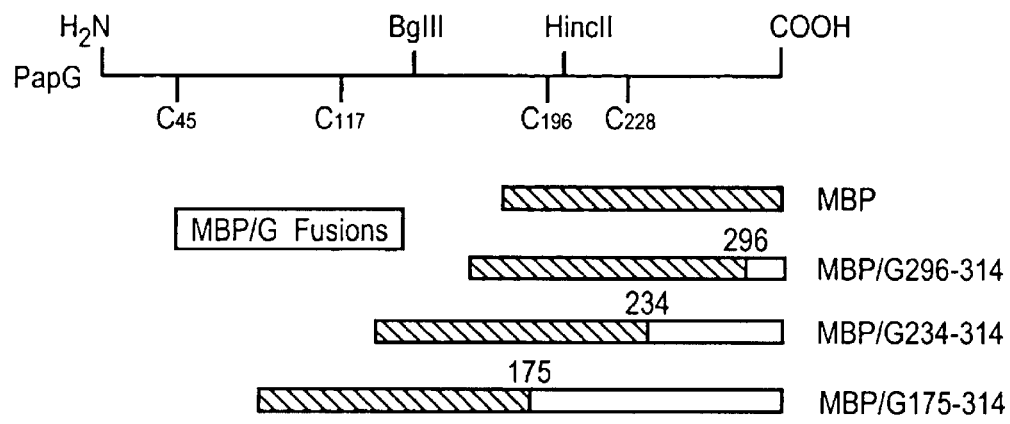
Figure 20:
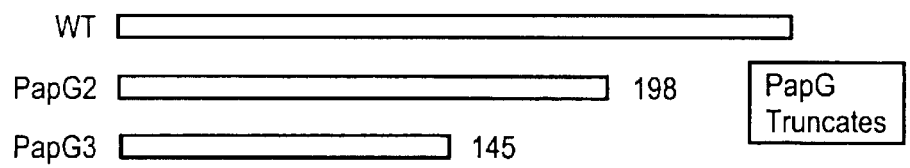
Figure 20:
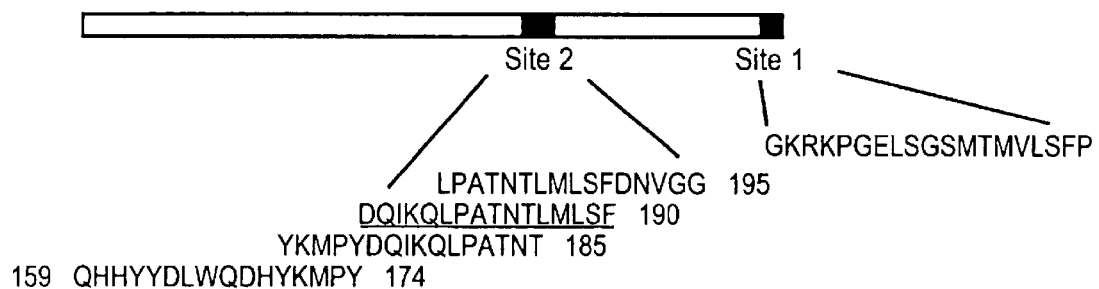

FIG. 20: MBP/G fusion constructs, PapG-truncates and synthetic peptides used in example 10.

The open box indicates the primary sequence of PapG. The positions of the four Cys residues are shown. The hatched bar represents MBP. The starting and ending residues of PapG fused onto the COOH-terminus of MBP are noted for each fusion. The terminating residue for each PapG-truncate is also indicated. The names of the M3P/G fusion proteins are listed. In the lower portion of the figure, the solid boxes localize the PapD interactive sites and the sequences of the four peptides used in the example are listed (cf. also SEQ ID NOS: 19–22).

FIG. 21: PapD-MBP/G interactions in vivo. Periplasmic extracts containing PapD and each MBP/G fusion were subjected to amylose affinity chromatography. The eluates were analyzed on A) a 12.5% Coomassie blue stained SDS polyacrylamide gel; B) a western blot using anti-PapD antiserum; or C) a silver stained IEF gel. In FIGS. 21A, B and C, samples were purified form periplasmic extracts containing PapD and MBP (lane 1), PapD and MBP-G1'-19' (lane 2), PapD and MBP-G1'-81' (lane 3), PapD and MBP-G1'-140' (lane 4). The position of co-purified PapD is indicated. MBP alone and MBP/G fusion truncates also co-purified with the MBP/G fusions. The molecular weight of the slowest migrating bands on SDS-PAGE correspond to each full length MBP/G fusion protein. On the IE F gel (C) several bands could be seen for the same reasons. A unique band at pI 5.2 was detected in FIG. 2C, lane 4. This band was excised, boiled in SDS sample buffer and analyzed by western blotting with anti-PapD and anti-MBP antisera. It was composed of both MBP-G1'-140' and PapD (FIG. 2D, lane 1).

Figure 22A:
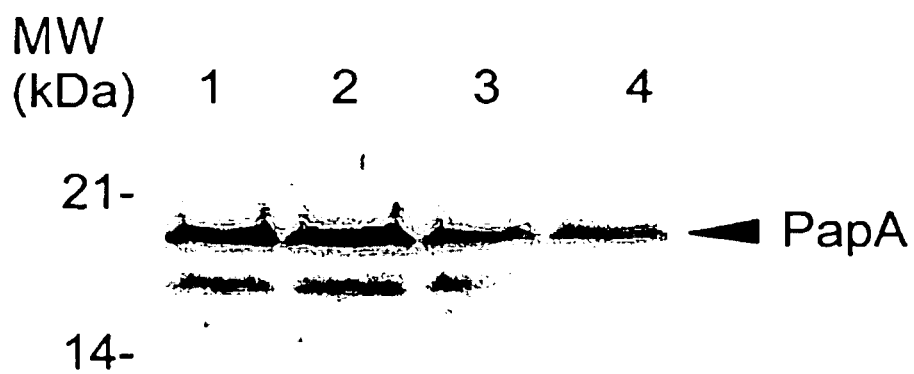
Figure 22B:
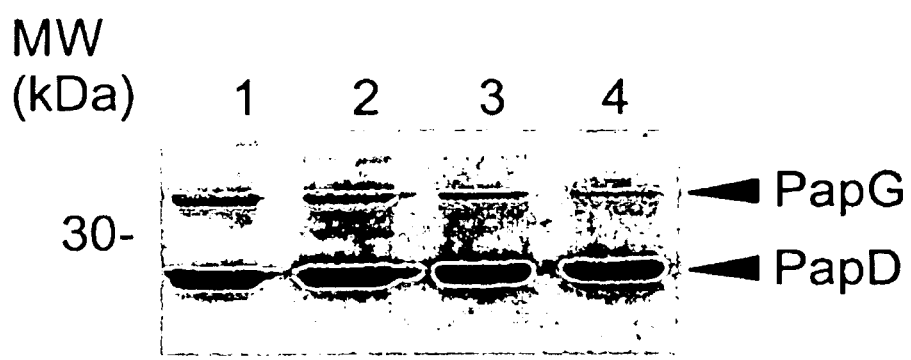
Figure 22C:
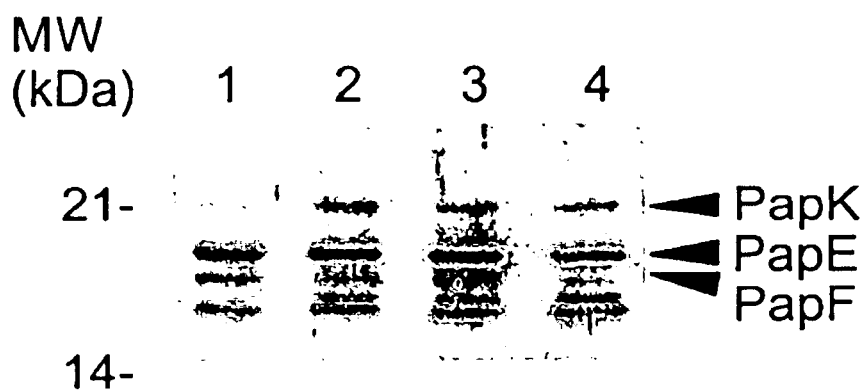

FIG. 22: Inhibition of chaperone function by expression of MBP/G fusions in vivo.

Strains carrying pFJ22 (papDJKEFGA) and plasmids encoding the MBP/G fusions were induced with 1 mM IPTG. Periplasmic extracts containing pilus subunits and MBP (lane 1), or MBP-G1'-19' (lane 2), or MBP-G1'-81' (lane 3), or MBP-G1'-140' (lane 4) were analyzed by western blotting using anti-PapA antiserum (A), or anti-PapD-PapG antiserum (B), or anti-tip fibrillum antiserum (C). In this assay the presence of the subunit indicates that chaperone-subunit interactions occurred since subunits are degraded in the absence of an interaction with the chaperone. Note that the presence of the PapA, PapG and PapF subunits decrease significantly when co-expressed with MPB-G11–140'.

FIG. 23: Binding of PapD to MBP/G fusion proteins in vitro.

(A) PapD was incubated with 1 μg of amylose affinity purified MBP (lane), MBP-G1'-19' (lane 2), MBP-G1'-81' (lane 3), or MBP-G1'-140' (lane 4) and complex formation was evaluated on the silver stained IEF gel. Positions of MBP/G fusions, PapD and the PapD-MBP-G1'-140' complex are indicated.

(B) Amylose affinity purified MBP/G fusion proteins were coated to wells of microtiter plates. The concentration of the MBP/G proteins in the wells is indicated. Binding of 50 pmol/50 ml of PapD to the immobilized proteins was determined by ELISA using anti-PapD antiserum.

Figure 24:
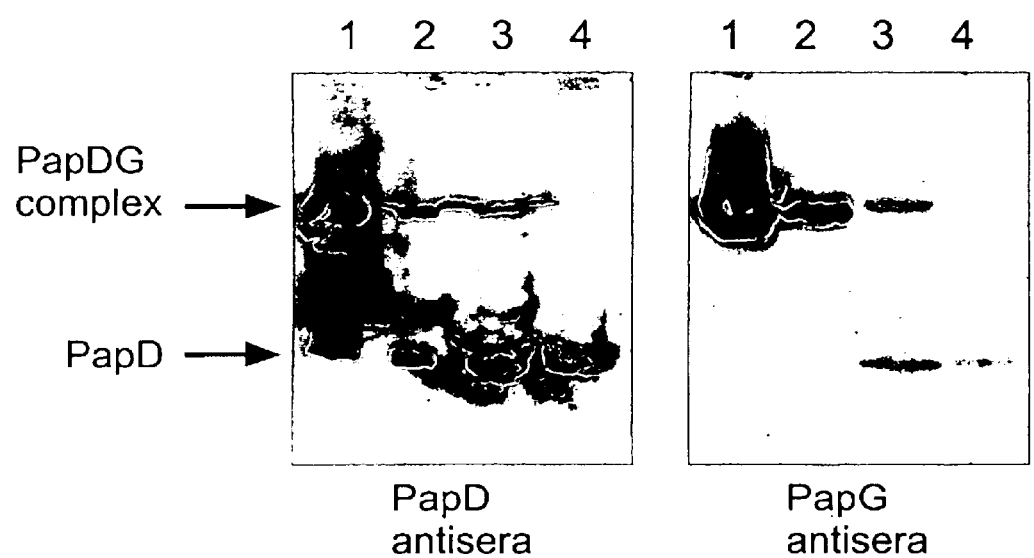

FIG. 24: Identification of PapD-PapG2 truncate complex by acidic native gel electrophoresis.

Periplasm containing PapD and PapG, PapG2 or PapG3 (lane 2, 3 and 4 respectively) were subjected to Gal α(1–4) Gal chromatography and eth eluates were analyzed on acidic native gel electrophoresis following western blotting using anti-PapD (A) and anti-PapG (B) antisera. Purified PapD-PapG complex was loaded in lane 1.

Figure 25:
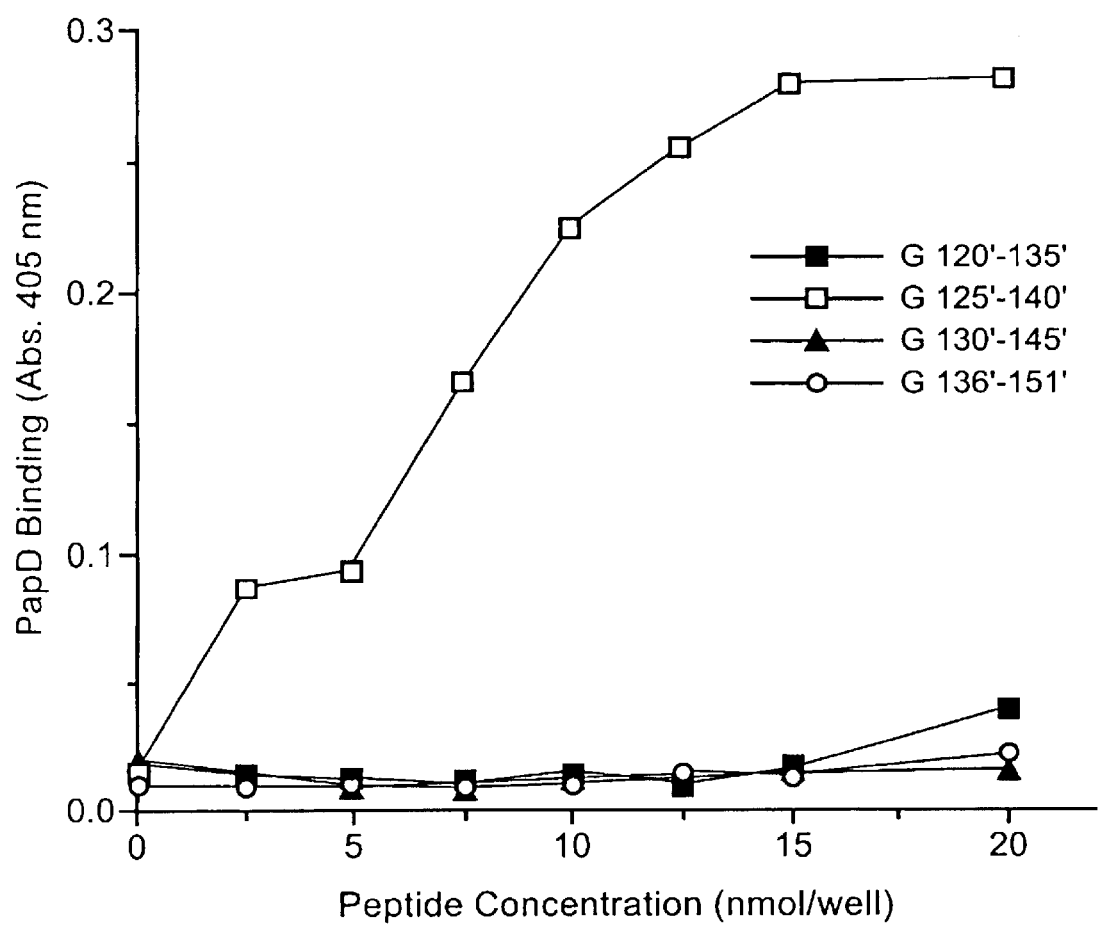

FIG. 25: Characterization of a second site on PapG recognized by PapD.

Four synthetic peptides overlapping the PapG region from residue 156' to 120' (indicated in FIG. 20) were coated to wells of microtiter plates. The concentration of each peptide in the wells is indicated. Binding of 200 pmol/50 ml of PapD to the immobilized peptide was determined by ELISA using anti-PapD antiserum.

EXAMPLES

Example 1

Identification of the Motif of Binding Between PapD and G1'-19'WT

Materials and Methods

PapD was prepared as described by A. Holmgren et al. in *J. Mol. Biol.* 203, 279 (1988) and obtained from the Department of Molecular Microbiology, Washington University School of Medicine, St. Louis, USA.

The peptide G1'-19'WT was prepared using Fmoc solid phase synthesis followed by purification by reversed phase HPLC. The peptide was obtained form Department of Chemistry, University of Lund, Lund, Sweden. Table 1 indicates the peptides used in binding assays in this application.

In the present application, amino acid residues or peptide fragments originating from other peptides than PapD (e.g. from PapG or from PapK) will be indicated with ', e.g. "G1'-19'WT" or "Pro-1'", in order to distinguish such residues from amino acid residues of PapD. Further, the numbering is from the C-terminal end of the non-PapD peptide, i.e. G1'-19' denotes the 19 C-terminal amino acid residues of PapG.

Crystallisation of PapD-peptide Complex

Crystals of the PapD-peptide complex were obtained by vapour diffusion against 20% PEG8000, 0.1 M cacodylate buffer at pH 5.0, and 0.2 M calcium acetate. The crystallisation drop contained equal volumes of reservoir and protein solutions. The protein solution (17 mg/ml) contained a 1:1 molar ratio of PapD and peptide in 20 mM MES (2-[N-Morpholino]ethane sulphonic acid) at pH 6.5 with 1.0% β-octyl glucoside.

X-ray Crystallography

The obtained crystals of the complex between PapD and the protein were mounted inside sealed quartz-glass capillary tubes and initially characterised by examining them on a X-ray precession camera thereby obtaining pictures of the X-ray diffraction pattern on photographic film representing spatially non-distorted images of the reciprocal lattice of the crystals. Using standard analysis of the images, it was determined that the crystals have a monoclinic space group, C2, with cell dimensions: a=130.7 Å, b=83.5 Å, c=59.2 Å, and β=117.2°, two molecules in the asymmetric unit and diffract to 2.9 Å resolution on a lab X-ray source with a rotating anode and Cu $K_\alpha$ target.

Collection and Processing of Experimental Data

In order to solve the atomic structure of molecules by X-ray crystallography, the positions and intensities of the diffraction maxima have to be measured. Intensity data for the PapD-peptide crystals were collected on a Huong-Hamlin multiwire area-detector system (Xuong et al., 1985). All data were obtained from a single crystal and initially processing was carried out using the MADNES software package (Messerschmit and Pflugrath, 1987). Merging and scaling of the data was carried.out using ROTAVATA and AGROVATA from the CCP4 package (see CCP4, The SERC (UK) Collaborative Project No. 4, A Suite of Programs for Protein Crystallography, Darebury Laboratory, UK). The final data set contained 9592 independent reflections with an Rsym of 6.8% for data between 20.0 and 3.0 Å resolution $$(Rsym = \sum \sum \frac{\langle |I_{hi}| - |I_h| \rangle}{\sum_{hi} I_{hi}},$$

where $I_{hi}$ and $I_h$ are the intensities of the individual and mean structure factors, respectively).

Solution of Three-dimensional Structure

The structure of the PapD-peptide complex was solved using the program XPLOR performing the standard method of molecular replacement. The search model used was the refined 2.0 Å resolution structure of PapD. Using 8.0 Å to 4.0 Å resolution data, the self-rotation function gave a clear non-crystallographic two-fold axis, and the top two peaks of the cross-rotation gave the correct solution which was improved using Patterson correlation (PC) refinement. The correct solution was also obtained from the top peaks in the translation functions, the R-factor being 39.0% for 8.0 to 4.0 Å resolution data (the R-factor defined as $$R - factor = \frac{\sum |Fo| - |Fc|}{\sum Fo}).$$

Refinement was obtained with subsequent rigid body refinement in which all four domains of the 2 PapD molecules in the asymmetric unit were allowed to refine independently resulting in a R-factor of 36.4% for the same data.

Examination of an |Fo|–|Fc| electron density map at this stage using the graphics program O showed clear density corresponding to the peptide in the PapD cleft and running along the surface of the protein. The orientatiQn of the peptide was easily determined from the electron density, but initially only the final 10 C-terminal amino-acids of the peptide could be modeled into density.

Refinement and Analysis of Structure.

Simulated annealing refinement with XPLOR was initiated at this stage. Several additional cycles of model building and refinement were carried out with a further 4 peptide amino-acids being added to yield an R-factor for the current model of 18.2% for 8.0 to 3.0 Å resolution data. The model at the present stage of refinement (which contains no water molecules and does not include the first 5 N-terminal amino-acids of the peptide) has root-mean square (rms) deviations from ideal geometry of 0.020 for bonds lengths and 4.2° for bond angles.

The peptide is seen to bind in an extended conformation with the C-terminal pro-1' anchored within the inter-domain cleft and proposed (6) subunit binding site. Hydrogen bonds are formed between the peptide carboxy terminus and two invariant positively charged residues of PapD, Arg-8 and Lys-112. Site-directed mutagenesis has now confirmed that Arg-8 and Lys-112 are essential for the binding of pilin subunits both in vitro and in vivo (cf. example 2)). The Pro-I' side chain makes van der Waals contacts in the cleft with residues form both domains of PapD: Thr-7, Thr-152, Ile-154, Thr-170 and Ile-194. The neighbouring peptide residue, Phe-2', lies in a shallow pocket formed between the two β-sheets of the N-terminal domain and makes hydrophobic interactions with Leu-4, Thr-7, Thr-109 and Ile-111. The peptide then runs along the surface of the N-terminal domain, forming a parallel β-strand interaction with strand Gi. In this way 7 main chain hydrogen bonds are formed between Met-8' to Phe-2' of the peptide and Gln-104 to Lys-110 of PapD, thus extending the β-sheet of PapD out into the peptide.

Apart form the C-terminal residues Phe-2' and Pro-1' there are relatively few contacts between the side chains of the peptide and PapD. The major interactions are provided by the main chain hydrogen bonds to strand Gi. There are, however, a number of hydrophobic interactions within the β-sheet, in particular between the peptide's Met-8' and Met-6' with Leu-103, Ile-105 and Leu-107 of strand G1.

Calculations revealed that the four hydrophobic peptide side chains of residues 2', 4', 6', and 8' contribute 20% of the total buried surface area (582 Å$^2$) between the peptide and the protein. Therefore, even though the major stabilization of the complex is provided via hydrogen bonding, hydrophobic interactions are not insignificant, and it is believed that they provide part of the explanation for the specificity of PapD for pilus related peptides and subunits. Experimental support of this theory is provided by the reduced binding of PapD to the peptide G2'-21'amide as compared to the G1'-19'WT peptide (FIG. 1B and table C). Hydrogen bonding of the COOH-terminus of the G2'-21'amide (which lacks Pro-1') to Arg-8 and Lys-112 of PapD allows main chain hydrogen bonding, but dislocates the four hydrophobic side chains in the peptide from their subsites in PapD, resulting in a reduction in binding strength.

Within the crystal the PapD-peptide β sheet was extended even further as a result of non-crystallographic twofold symmetry which placed a second PapD-peptide complex adjacent to the first so that the two bound peptide chains interacted as antiparallel β strands. In the present model, eight main chain hydrogen bonds are formed between the two peptides; see the following table:

TABLE B

| PapD$_1$ | Peptide$_1$ | Peptide$_2$ | PapD$_2$ |
|---|---|---|---|
| | | Pro-1'-COOH | Arg-8-NH$_2$ |
| | | Pro-1'-COOH | Lys-112-NZ |
| | | Phe-2'-NH | Lys-110-C=O |
| | Glu-13'-NH | Ser-3'-C=O | |
| | Glu-13'-C=O | Ser-3'-NH | |
| | | Leu-4'-C=O | Lys-110-NH |
| | | Leu-4'-NH | Gln-108-C=O |
| | Ser-11'-NH | Val-5'-C=O | |
| | Ser-11'-C=O | Val-5'-NH | |
| | | Met-6'-C=O | Gln-108-NH |
| | | Met-6'-NH | Ala-106-C=O |
| | Ser-9'-NH | ? Thr-7'-C=O | |
| | Ser-9'-C=O | ? Thr-7'-NH | |
| Gln-104-C=O | Met-8'-NH | Met-8'-C=O | Ala-106-NH |
| Ala-106-NH | Met-8'-C=O | Met-8'-NH | Gln-104-C=O |
| | Thr-7'-NH | ? Ser-9'-C=O | |
| | Thr-7'-C=O | ? Ser-9'-NH | |
| Ala-106-C=O | Met-6'-NH | | |
| Gln-108-NH | Met-6'-C=O | | |
| | Val-5'-NH | Ser-11'-C=O | |
| | Val-5'-C=O | Ser-11'-NH | |
| Gln-108-C=O | Leu-4'-NH | | |
| Lys-110-NH | Leu-4'-C=O | | |
| | Ser-3'-NH | Glu-13'-C=O | |
| | Ser-3'-C=O | Glu-13'-NH | |
| Lys-110-C=O | Phe-2'-NH | | |
| Lys-112-NZ | Pro-1'-COOH | | |
| Arg-8-NH$_2$ | Pro-1'-COOH | | |

A mixed β sheet is thus created between the two complexes and extends over ten β strands (FIG. 5). No contacts are observed between the two non-crystallographically related PapD molecules themselves, both of which were positioned in similar environments within the crystal and possessed a similar number of intermolecular contacts. The calculated buried surface area between the two non-crystallographically related peptides was 520 Å$^2$, a value similar to the surface area buried between the protein and peptide. This "dimerization" appears to be a consequence of crystal packing, because all evidence shows that PapD forms monomeric complexes with peptides or with intact PapG in solution.

The hydrogen bonding pattern between PapD and the peptide breaks at Ser-9', but the peptide remains in van der Waals contact with PapD until Ser-11' where the peptide runs beyond the F1-G1 loop, but remains hydrogen bonded to the non-crystallographically related peptide as far as Glu-13' (table B). The last resolved amino acid of the peptide is Gly-14' which is positioned close to the binding cleft of the non-crystallographically related PapD. the first five amino terminal amino acids, including three positively charged residues, had no density and therefore must have been disordered in the crystal structure. In agreement with this, the peptide's amino terminus is not important for binding to PapD in solution, since the G1'-7'WT peptide lacking the amino terminal 12 amino acids is found to be an effective inhibitor of PapD binding to the immobilized G1'-19'WT peptide (table C and example 2).

The structures of the individual PapD domains in the peptide complex are essentially the same as those of native PapD (Holmgren and Branden, 1989). However, there is a significant movement of the domains with respect to each other with a 13° jaw-closing or hinge bending motion making the angle of the PapD boomerang more acute (FIG. 6). Whether or not this conformational change is the result of binding of peptide or different crystal packing between the two crystal structures is unclear.

In the native PapD structure the electron density obtained for the long F1-G1 loop is poor between residues 96 and 102, suggesting that it is rather flexible and disordered in the crystal. In the peptide complex, however, this loop is better resolved, indication that binding of the peptide makes this loop more rigid. Superimposing the NH$_2$-terminal domains of native PapD and the peptide complex shows that there is also a significant difference in the F1-G1 loop position between the two structures (rms for the 110 NH$_2$-terminal Cα atoms is 1.84 Å, with a maximum main chain movement of about 9 Å for Leu-103). In the peptide complex the loop is seen to twist at one end away form the β barrel of the NH$_2$-terminal domain thus facilitating a more extensive contact between strand G1 and the peptide. As with the hinge-bending of the two domains, it is not yet possible to say with certainty whether this loop shift is a consequence of peptide binding or of crystal packing; the rather open conformation. of the F1-G1 loop suggests that it may be largely the latter. Nevertheless, evidence that similar interaction between PapD and peptides or pilus subunits occur in solution is provided by protease protection experiments after the F1-G1 loop of PapD is protected from tryptic cleavage by the binding of both native PapG and the G1'-19'WT peptide (example 2 and FIG. 2A).

Example 2

Binding Between PapD and the Carboxyl Terminus of Other Pap Peptides

G1'-19'WT, E1'-19'WT, F1'-19'WT, K1'-19'WT and H1'-19'WT peptides (see table 1) were synthesized corresponding to the 19 carboxyl terminal residues of P pilus subunit proteins PapG, PapE, PapF, PapK and PapH, respectively (see: Grant et al., 1992, and references cited therein).

TABLE 1

| Name | SEQ ID NO: | Peptide sequence |
|---|---|---|
| G1'-19'WT | 6 | NH$_2$-GKRKPGELSGSMTMVLSFP-COOH |
| G1'-16'WT | 7 | NH$_2$-KFGELSGSMTMVLSFP-COOH |
| G1'-11'WT* | 8 | NH$_2$-SGSMTMVLSFP-COOH |
| G1'-7'WT | 9 | NH$_2$-TMVLSFP-COOH |
| G1'-19'SV | 10 | NH$_2$-GKRKPV̲ELSGSMTMVLSS̲P-COOH |
| G1'-19'amide | 11 | NH$_2$-GKRKPGELSGSMTMVLSFP-CONH̲$_2$ |
| G2'-21'amide | 12 | NH$_2$-E̲E̲GKRKPGELSGSMTMVLSF-CONH̲$_2$ |
| E1'-19'WT* | 13 | NH$_2$-QNLIAGPFSATATLVASYS-COOH |
| H1'-19'WT | 14 | NH$_2$-KKLEAGNYFAVLGFRVDYE-COOH |
| K1'-19'WT | 15 | NH$_2$-KSVVPGDYEATATFELTYR COOH |
| F1'-19'WT | 16 | NH$_2$-GILNGGDFQTTASMAMIYN-COOH |
| MS | 17 | NH$_2$-YALAPNAVIPTSLALL-COOH |

* Water insoluble peptides

The residues in the peptides were numbered starting with the carboxyl terminal residue as 1, and ending with the amino terminal residue. Peptides were also synthesized which deviated in length (G1'-16'WT, G1'-11'WT, G1'-7'WT) or sequence (G2'-21'amide, G1'-19'SV, G1'-19'NH$_2$) from the wild type PapG carboxyl terminal sequence. Using an enzyme-linked immunosorbent assay (ELISA), we tested the ability of PapD to bind to each peptide coated on wells of microtiter plates:

5 mg/ml stock solutions of peptides in water or 50% acetic acid were diluted to a concentration of 2.5 pmol/50 μl in PBS. 50 μl of the peptide solution was coated overnight onto microtiter wells (Nunc-Immuno Plate Maxisorp) at 4° C. The solutions in the plates were discarded, and the wells were blocked with 200 μl 3% bovine serum albumin (BSA, Sigma) in PBS (120 mM NaCl/2.7 mM KCl/10 mM phosphate buffer salts, pH 7.4) for 2 hours at 25° C. The plates were washed vigorously 3 times with PBS and incubated with 50 μl of the indicated amount of purified PapD (Lindberg et al, 1989). After 3 washes with PBS, the wells were incubated with a 1:500 dilution of anti-PapD rabbit antiserum (Lindberg et al, 1989) in 3% BSA/PBS for 45 min. at 25° C. After 3 washes with PBS, the wells were incubated with a 1:1000 dilution of goat anti-rabbit IgG coupled to alkaline phosphatase (Sigma) in 3% BSA/PBS for 45 min. at 25° C. Following 3 washes with PBS and 3 washes with developing buffer (10 mM diethanolamine pH 9.5, 0,5 mM $MgCl_2$), 50 μl filtered p-nitrophenyl phosphate substrate (Sigma) in developing buffer (10 mg/ml) was added. The absorbance at 405 nm was. read after 60 min of incubation in the dark at 25° C.

In addition, the ability of water-soluble peptides to inhibit PapD binding to G1'-19'WT-coated wells in a soluble inhibition ELISA were tested, since peptide conformations may have been affected by binding to the plastic microtiter plates:

Microtiter wells were coated overnight at 4° C. with 50 μl of 2.5 pmol/50 μl of the G1'-19'WT peptide. The wells were washed with PBS and blocked with 3% bovine serum albumin (BSA). A 25-fold molar excess of each test peptide was preincubated with 100 pmoles PapD for 30 min. and the PapD-peptide solution was then added to the coated wells and incubated at 25° C. for 45 min in the presence of 3% BSA/PBS. The subsequent primary antibody, secondary antibody and developing steps are described above. The ability of the peptides to inhibit binding of PapD to the G1'-19'WT peptide was calculated by dividing the amount of PapD binding in the presence of peptide with the amount of PapD binding in the presence of water. 0 inhibition includes values where binding was greater than that of PapD pre-incubated with $H_2O$.

Figure 1B:
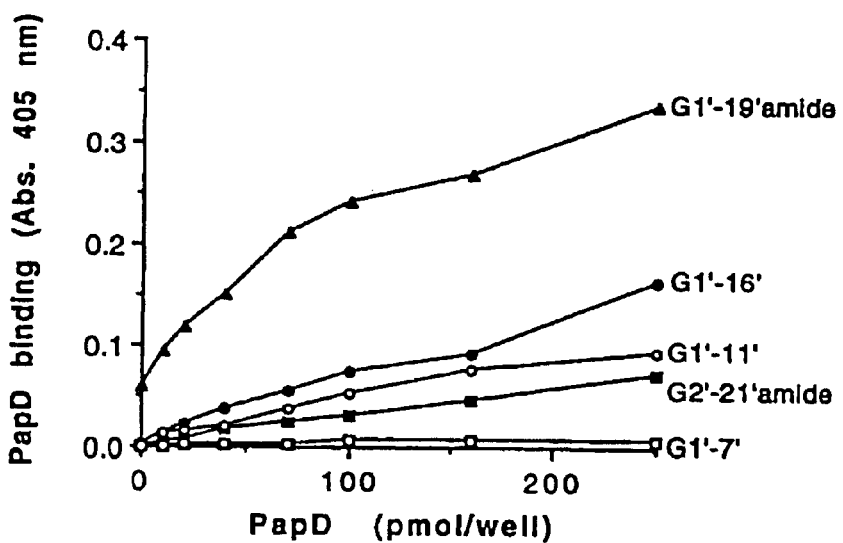

The results of PapD binding to wild type, variant and different length peptides are shown in FIGS. 1A, B and C.

As can be seen the peptides bound well to the PapG peptide, moderately to PapE, PapF and PapK, whereas there was no binding to PapH and the random hydrophobic peptide, MS. (FIG. 1A). These results suggest that the chaperone recognizes PapG, PapE, PapF and PapK in part by binding to the carboxyl terminus of these subunits. The inability of PapD to interact with the PapH peptide indicates that PapD binds differently to PapH, possibly due to PapH's function as a polymerization terminator (Baga et al., 1987). The ability of a peptide to inhibit PapD binding to immobilized G1'-19'WT generally corresponded to the affinity that PapD had for the respective immobilized peptide (FIG. 1, % inhibition), arguing that the interaction of PapD with soluble and immobilized peptides is similar.

As can be seen from example 1, the molecular basis of the PapD-peptide interactions have been studied by co-crystallization of PapD with the G1'-19'WT peptide. In summary, the 19 amino acid peptide is anchored in the chaperone cleft by hydrogen bonds between the peptide's carboxy terminus and Arg-8 and Lys-112 which are invariant in all periplasmic chaperones (Holmgren et al., 1992). The peptide bound to the G1 strand of PapD as a parallel β-strand, forming at least 10 backbone hydrogen bonds, and resulted in an ordering of the F1 to G1 loop.

Replacement of the carboxyl terminal proline on the PapG peptide with an amide (G2'-21'amide) abolished binding to PapD. in solution and reduced binding of PapD to the immobilized peptide by approximately 75% (FIG. 1B). In contrast, substituting only the carboxylate group with an amide to create the G1'-19'$NH_2$ peptide did not affect binding to PapD in either the immobilized or soluble inhibition ELISA assays (FIG. 1B). These results indicate that the terminal proline probably is required to position the carboxylate group so that it can form hydrogen bonds with the invariant Arg-8 and Lys-112 cleft residues.

PapD also binds to the immobilized shorter peptides G1'-16'WT and G1-11'WT and the G1'-16'WT and G1'-7'WT peptides inhibited binding of PapD to the immobilized G1'-19'WT peptide in solution. Table C shows the ability of a 25-fold molar excess of the water soluble peptides to inhibit binding of 100 pmol/well of PapD to G1'-19'WT-coated wells. The % inhibition represents the percentage of PapD binding in the presence of the peptide compared to in the presence of water and are the average of two experiments performed in duplicate:

TABLE C

| Peptide | % Inhibition |
|---|---|
| G1'-19' | 63 |
| G1'-7' | 49 |
| G1'-4' | 0 |
| MS | 1 |
| G2'-21' amide | 0 |
| G1'-19' amide | 56 |

PapD does not bind to immobilized G1'-7'WT peptide, probably because this peptide is to short to bind to the microtiter well as well as PapD. It, thus seems that as few as 7 carboxyl terminal residues are necessary for PapD binding of a peptide. Together these results support a model where, in addition to the anchoring interaction of the carboxylate group in the PapD cleft, seven carboxyl terminal residues are required for "zippering" the peptide along the G1 strand of PapD during PapD-peptide complex formation.

Conserved residues phenylalanine and glycine residues at positions 2 and 14 from the carboxyl terminus were substituted by serine and valine, respectively, to create the peptide G1'-19'SV and decreased binding to PapD by 36%. This could result form less efficient coating or presentation in the microtiter plate since G1'-19'SV was as efficient a soluble PapD inhibitor as the peptide G1'-19'WT (FIG. 1B). Since these residues are critical for incorporation of PapG into the pilus, it is believed that they be more important for inter-subunit polymerization interactions and pilus assembly than in PapD subunit interactions in vivo.

Partial digestion with trypsin cleave PapD in the F1-G1 loop at residues Leu-103 and Lys-99, respectively:

400 μg of PapD was partially digested by incubation with either 4.5 μg trypsin or 0.45 μg chymotrypsin on PBS for 20 min. at 37° C. The PapD digests were applied to a C-18 HPLC column (Beckman) and 2 major fragments were eluted with a 0–100% acetonitrile gradient in 0.01% trifluoroacetic acid. The PapD fragments were identified by their molecular weight on SDS-PAGE and amino-terminal sequencing. The N-terminal amino acid sequences of the approximately 14 kDa tryptic and chymotryptic fragments were identified as residues 100–108 and 104–109 of PapD, respectively, corresponding to cleavage after Lys-99 (for trypsin) and Leu-103 (for chymotrypsin). The N-terminal sequences of the 11 and 12 kDa bands in the digests were identical to the N-terminal sequence of PapD.

Figure 2A:
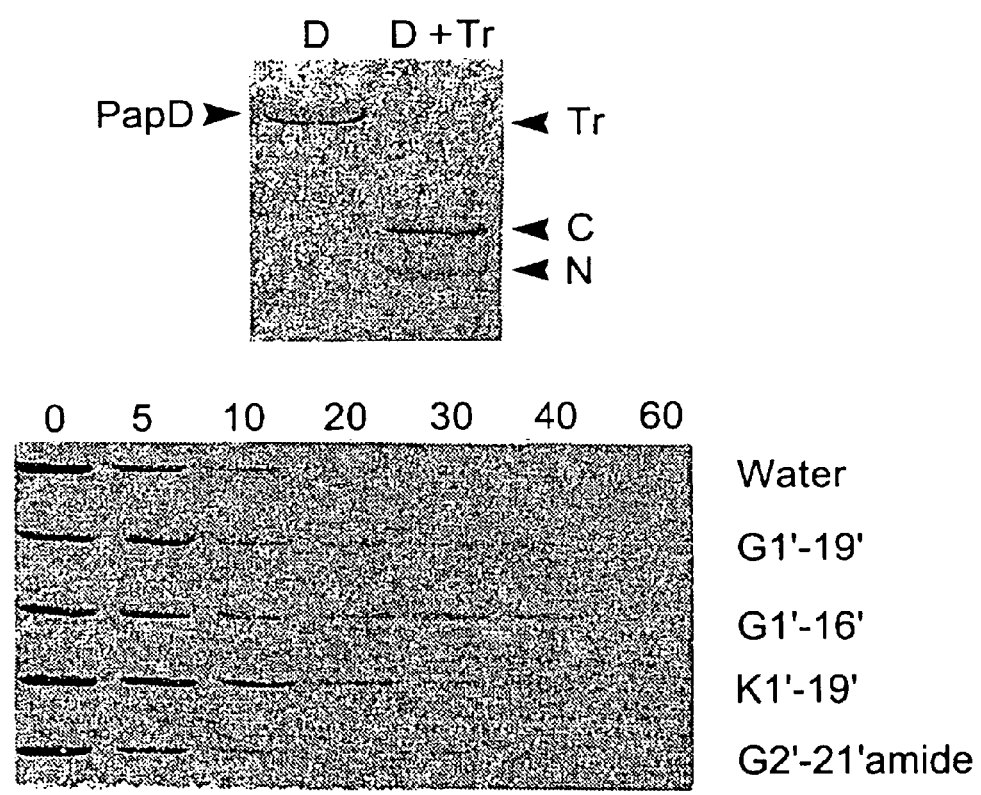

The G1'-19'WT, G1'-16'WT and K1'-19'WT peptides, but not the G2'-21'amide peptide, reduced the rate of tryptic cleavage of PapD over time (FIG. 2A). These data argue that binding of PapD to the peptide altered contacting the loop and thereby protectin to form cleavage. This effect may be related to the ordering of the F1-G1 loop of PapD observed in the PapD-peptide crystal structure, and suggests that, in solution, both peptides extends along the G1 β-strand and interact with the F1-G1 loop of PapD.

Figure 2B:
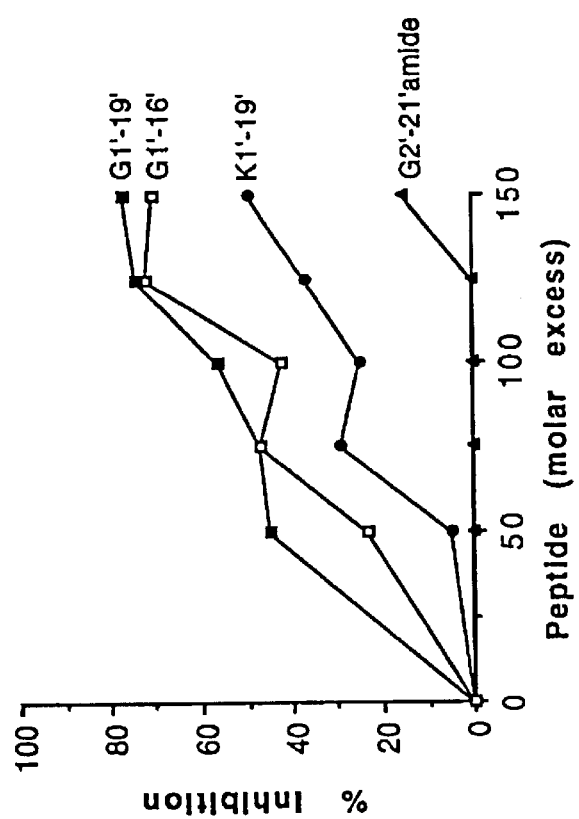

As described in Kuehn et al., Proc. Natl. Acad. Sci. USA 88, 10586 (1991), native PapD is able to bind to reduced, denatured PapG and restore the PapD-PapG complex in vitro. This reconstitution assay was used to determine the ability of the peptides to inhibit PapD activity in vitro. The limited solubility of the G1'-7'WT peptide unfortunately has prevented the testing of this peptide in the assay. Increasing amounts of the G1'-19'WT, G1'-16'WT and K1'-19'WT peptides inhibit restoration of the PapD-PapG complex by PapD, while the G2'-21'amide peptide has no effect (FIG. 2B). The ability of the G1'-19'WT, G1'-16'WT and K1'-19'WT peptides to prevent PapD form binding to PapG indicated that these peptides bound in the subunit binding site of PapD.

The ability of peptides to inhibit restoration of the PapD-PapG complex by PapD was tested as follows.: 0.3 μg of PapD-PapG complex was reduced and denatured by incubation at 25° C. for 20 min with 4 M urea/10 mM dithiothreitol (DTT), 1.2 μg (50 pmol) of PapD was incubated at 25° C. for 10 min with 5–14.5 μg (2.5–7.25 nmol) of peptide. The PapD-peptide solution was then added to the reduced, denatured PapD-PapG, incubated at 25° C. for 10 min, and applied to an IEF 3–9 gel (Pharmacia). The amount of PapD-PapG restored in each sample was quantitated by densitometry of the silver stained IEF band corresponding to the pI of the DG complex.

Site directed mutations in strictly conserved cleft residues of PapD predicted to be critical in the PapD-peptide interaction were constructed to test whether the PapD-peptide crystal structure is a reflection of part of the PapD-pilus subunit interaction interface (the positions of the mutations are indicated in FIG. 3). Highly conserved Thr-7 was changed to a valine (Thr-7-Val) in order to test whether its hydroxyl group formed hydrogen bonds critical for PapD binding to subunits.

This mutation removed the hydroxyl group while maintaining the steric volume of the side chain. Mutations in Lys-112 and Arg-8 were designed to test whether hydrogen bonding to the terminal carboxylate group of pilus subunits is a critical feature of the chaperone recognition process. The invariant Lys-112 residue was changed to an alanine (Lys-112-Ala) to remove the charged side chain and to a methionine (Lys-112-Met) to replace the charged group with a hydrophillic group while maintaining the side chain packing. The invariant Arg-8 has been shown previously to be required tor the ability of PapD to bind subunits and mediate pilus assembly in vivo (Slonim et al, 1992). Glu-167/E167, a variable residue in domain 2 of PapD (FIG. 3), does not appear to be involved in the interaction between PapD and the peptide in the crystal structure and mutations in this residue have been shown to have little or no effect on PapD function in vivo (Slonim et al, 1992). E167 was changed to histidine (E167H) to test whether this negatively charged residue at the lip of domain 2 has any role in the PapD-peptide interaction. All of the mutants were secreted into the periplasmic space as stable proteins similar to wild type PapD. In addition, the elution profile form a cation-exchange FPLC column and the electrophoretic properties of the purified mutant PapDs were similar to the wild type protein, supporting the prediction that these mutations would not affect the overall structure of PapD (data not shown).

The ability of the mutant chaperones to bind pilus subunits and modulate pilus assembly in vivo was correlated to their ability to bind to the G1'-19'WT peptide and to PapG in vitro. Wild type PapD bound the G1'-19'WT peptide to cause a mobility shift towards the negative electrode in a native polyacrylamide gel assay (Lam and Calderwood, 1992), probably due to a net positive charge increase in the PapD-peptide complex. In contrast, when Arg-8-Gly, Arg-8-Ala and Lys-112-Ala PapD mutants were incubated with the G1'-19'WT peptide they did not cause a mobility shift in the native-PAGE assay, indicating that these mutations in PapD abolished peptide binding. Similarly, mutations in Arg-8 and Lys-112 abolished the ability of PapD to bind to PapG and reconstitute the PapD-PapG complex in vitro (FIG. 7) and to bind to pilus subunits and mediate pilus assembly in vivo (cf. table 2).

TABLE 2

| Residue class | Mutation | HA titer* | Pilus assembly+ | Subunit stabilization# | | | | |
|---|---|---|---|---|---|---|---|---|
| | | | | PapA | PapE | PapG | PapF | PapK |
| Invariant | Arg-8-Gly | None | – | – | – | – | – | – |
| | Arg-8-Ala | None | – | – | + | – | + | – | + |
| | Arg-8-Met | None | – | – | ++ | – | ++ | – | ++ |
| | Lys-112-Ala | None | – | – | + | – | + | – | + |
| | Lys-112-Met | None | – | – | ++ | – | – | – | – |
| Conserved | Thr-7-Val | 64 | +++ | ++++ | ++++ | ++++ | ++++ | ++++ |
| Variable | Glu-167-X§ | 128 | ++++ | ++++ | ND | ND | ++++ | ++++ |

*The hemagglutination (HA) titer was quantitated after induction with 0.01 mM IPTG. The HA titer represents the greatest bacterial dilution which still agglutinates erythrocytes. HB101/pPAP37 expressing wild type PapD has an HA titer of 128.
+The amount of pili assembled were released from the cells and quantitated after induction with 0.01 mM IPTG. "–" indicates no pili were detected; the degree of piliation of HB101/pPAP37 expressing wild type PapD corresponds to "++++".
Chaperone-assisted periplasmic stabilization of pilus subunits PapA, PapE, PapF, PapK and PapG was determined as described previously (Slonim el at., 1992); "–" indicates no stabilization of the subunit; the number of +'s indicate the degree of subunit stabilization as compared to wild type PapD. ND indicates not determined.
§X indicates mutations to His, Asp, Thr, or Gly.

The remarkable consistency of the in vitro and in vivo results and the crystal structure argue that anchoring of pilus.subunits by conserved residues Arg-8 and Lys-112 is a critical part of the interaction between PapD-like chaperones and pilus biogenesis.

Site-directed mutagenesis was performed using the Bio-Rad in vitro mutagenesis kit following the manufacturers instructions. The following primers (non-coding strand) were used to introduce mutations in the papD gene (SEQ ID NO: 1):

```
Thr-7-Val   5'-GTCAAACACCGCCGGAACTCGTCCAGGCGA-3' SEQ ID NO: 3

Lys-112-Ala 5'-CGGGCGATAAAAAAGAGCTATTTTGGTCTG-3' SEQ ID NO: 4

Lys-112-Met 5'-GCGATAAAAAAGCATTATTTTCCTCTG-3'    SEQ ID NO: 5
```

Mutations in papD were confirmed by sequencing and the altered papD genes were cloned into vector pMME91 under the inducible Ptac promotor as previously described for other papD mutations (Slonim et al, 1992). The plasmids were named pThr-7-Val, pLys-112-Ala and pLys-112-Met according to the residue number and mutated amino acid. Plasmid pLS101 is an isogenic construct containing the wild type papD gene; plasmid pE167H, pR8G and pR8A contain genes encoding PapD with point mutations changing Glu-167 to His and Arg-8 to Gly and Ala, respectively.

The data presented in this example and example 1 demonstrate that the PapD-peptide interactions found in the crystal structure reflects the PapD-pilus subunit interaction interface in vivo. These interactions define for the first time a mechanism whereby chaperones utilize their immunoglobulin-like domains in a novel recognition paradigm to bind to a diverse group of proteins. PapD residues Arg-8 and Lys-112, located in β-strands in the cleft between the two domains, play crucial roles in chaperone recognition by servings as molecular anchors for the carboxyl terminus of pilus proteins. The fact that Arg-8 and Lys-112 are highly conserved amongst periplasmic chagerones indicates that they probably have a universal role in forming the "active site" that binds to the terminal carboxylate group of other protein subunits. Backbone hydrogen bonds along the β-strand of PapD subsequently provide strong, sequence-independent interactions along the length of the carboxyl terminus of the subunit. The "zippering" interaction of the conserved alternating hydrophobic residues of the carboxyl terminus of the pilus subunit with the conserved alternating hydrophobic residues in the G1 β-strand of the chaperone adds strength and specificity to the binding. Therefore, unlike other immunoglobulin-like proteins (Amit et al, 1988 and de Vos et al, 1992), PapD utilizes the β-strand and interdomain cleft features of its immunoglobulin-like structure to provide a recognition mechanism for binding to several different proteins. Variable residues in loop regions of antibodies provide the exquisite specificity necessary from an extensive antibody binding repertoire. Similarly, residues in the F1-G1 loop of PapD may provide specificity to chaperone binding since these have been found to vary in length and composition amongst members of the periplasmic chaperone family (Holmgren et al, 1992).

Example 3

Designing of Compounds Capable of Binding to the Binding Site of PapD

Having determined the location of a promising binding site for inhibitory ligands as described in Examples 1 and 2, the computer programs 'PLIM' and 'PLIM_DBS' (developed by Symbicom AB) were used to find templates for families of compounds capable of binding to the binding site (see the general description above).

PLIM was run on a 20 Å box around the Arg-8 region of the high-resolution structure of PapD, searching for low-energy binding positions for NH, $NH_2$, O, OH and C probes. The PLIM runs resulted in a number of suggested positions and orientations of favourable chemical groups (site points) in the region near Arg-8 and Lys-112.

Approximately 50 sites were identified, and then triplets and quartets of these site points were selected for their mutual compatibility, that is to say they must have appropriate geometric relationships—distances and orientations that could be found in a real molecule.

A search for potential ligands was then made by searching a database for known molecular structures that match the positions of these groups of site points, using PLIM_DBS.

The best of these database hits were examined visually using a computer-graphic modelling system, and the most promising of these were selected according to a wealth of physico-chemical reasoning.

Modifications were made as described above to improve binding and simplify synthesis. For example, phenyl rings were added to give better complementarity to the hydrophobic surface of the binding site, charged groups were added to bind to charged groups on the protein that had been outside the scope of Plim, frequently toxic sub-structures were removed, and groups were replaced with functionally similar ones for synthetic reasons. Many such judgements were made, resulting in two families of compounds (hdo and bpy) with differing combinations of characteristics.

The efficacy of these modifications was finally assessed using molecular-dynamics free energy calculations as described herein to study the stability of the protein-ligand complex (Åqvist et al., 1994).

Two structures from one family and one from the second family were then deemed worthy of synthesis and testing.

The development of a number of the member of these families of compounds will now be described in detail.

The first family (herein referred to as hdo) was derived from database entry for 6-hydroxydopamine, denoted hdo__0 (FIG. 8). The molecule binds to the PapD side chains of Arg-8 and Lys-112, and to the backbone of Lys-110 through hydrogen-bond donation from the hydroxyl groups. The primary-amino group hydrogen-bonds to the side chain of Thr-170.

Derivative hdo__1 (FIG. 8) was created from this base structure by replacing an hydroxyl group with a carboxylic acid that can have a charge interaction with Arg-8 and Lys-112, and replacing the hydroxyl para to this position with a new phenyl ring, in order to fill out the hydrophobic cleft in the protein formed by the residues Ile-111, Leu-4 and part of Thr-7. hdo__4 (FIG. 8) was created from hdo__1 by replacing the original aromatic ring with a sugar, attaching the hydroxyl, primary amine and carboxylic acid substituents in such a way as to maintain similar relative geometries, and then adding hydroxyl groups to one side of the new benzene ring so as to present a hydrophillic face to the solvent in this region.

At this point the structure looked convincing enough to invest time in a molecular-dynamics simulation, the results of which suggested that the amino group would not in fact bind. to the gamma-carbon of Thr-7 of PapD, but would preferentially point into solution, satisfying its hydrogen-bonding requirements with water molecules rather than with the protein side-chain. Thus, the amine group was replaced by the singly donating hydroxyl group, a step that also simplified synthesis, the result being structure hdo_6 (FIG. 8).

Due to the perceived probability of toxicity due to the hydroxyl substitution pattern on the benzene ring, the para-hydroxyl group was removed to give structure hdo$_{13}$ 7 (FIG. 8), and the remaining hydroxyl group on this ring was replaced by a nitro group for further ease of synthesis (hdo_8, FIG. 8).

A final compound with the previous nitro group left off was also considered a possibility, and was known as hdo_9 (FIG. 8).

Another molecular-dynamics simulation was run, on hdo_9, the results of which suggested that now the predicted interactions would indeed be made and maintained in solution. A statistical analysis of the trajectories with the program "Miss_Fit" showed that the conformation of the ligand did not change substantially during the run, and changes that did occur were compensated for by complementary shifts in the protein structure that maintained all significant interactions.

Dynamics simulation of hdo_8 was complicated by the lack of availability of suitable molecular-mechanics parameters for the meta-nitro substituted ring, which made assessment through molecular-dynamics simulations harder to rely upon, and this influenced the decision to pursue hdo_9.

The range of possibilities that were considered during the design phase of the hdo family are summarised in FIG. 9.

The second family, known as bpy, was derived from a database entry for (methyl-O,N,N-azoxy)-methyl-β-D-glucopyranoside cycasin (Kawaminami et al, 1981) denoted as bpy_0 herein:

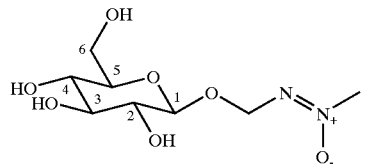

bpy_0

The conformation stored in the database was non-optimal for binding to the PapD site, though it was close enough to be picked out by the Plim_DBS search. Small adjustments made to the internal torsion angles improved the binding pattern somewhat.

It is interesting to note that there are precedents for the approach of using a central carbohydrate as a scaffold to which functionalities are attached as to mimic a peptide (Hirschmann et al, 1992).

Derivative bpy_1 was then created by adding a phenyl ring to the 6-position, in order to fill out the hydrophobic cleft in the protein. The 4-OH group should form a favourable dipole interaction with the electron-rich centre of the 6-phenyl group, and together with the 6-OH.O5 intramolecular hydrogen bond should stabilize the desired C5–C6 rotamer.

It was decided that the Lys-112 and Arg-8 side chains that should interact with the hydroxyl group at the 2-position in the ligand do so even more with a charged group, and therefore bpy_2 was created by replacing this hydroxyl with a sulphate, bpy_3 by replacing it with a cyclic phosphate, and bpy_5 by replacing it with a non-cyclic phosphate.

bpy_4 was created by removing the 3-hydroxyl group from BPY_2 so that the sulphate group had a better chance of interacting with the Arg-8 side chain, and bpy_6 was analogously created by removing the 3-hydroxyl group from bpy_5. The following formula shows bpy_1-bpy_6:

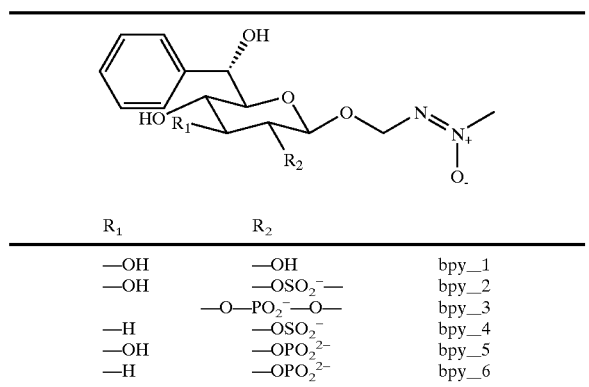

| R$_1$ | R$_2$ | |
|---|---|---|
| —OH | —OH | bpy_1 |
| —OH | —OSO$_2^-$— | bpy_2 |
|  | —O—PO$_2$—O— | bpy_3 |
| —H | —OSO$_2^-$ | bpy_4 |
| —OH | —OPO$_2^{2-}$ | bpy_5 |
| —H | —OPO$_2^{2-}$ | bpy_6 |

Consideration was then given to a small hydrophobic pocket and patches or hydrophobic residues exposed to the solvent near position 1 on the ligand. An aglycon that could make contact with these parts of the protein and preferably also interact with solvent was sought. These considerations led to the replacement of the azoxy group at position 1 with a 2-hydroxy-4-methylcyclopentyl group, resulting in bpy_7:

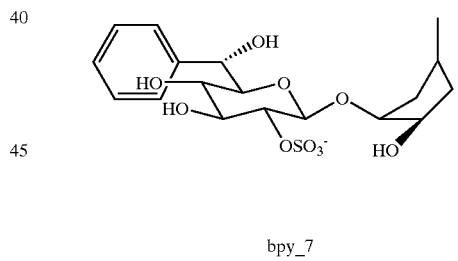

bpy_7

At this point, a molecular dynamics run was made, the results of which suggested that the structure bound well, but that the expected hydrophobic contacts between the cyclopentane and the protein were not maintained.

Thus, bpy_9 was created from bpy_7 with the cyclopentane group removed, replaced by an α-methyl group for internal stability. Instead, further hydrophobic contact was attempted by the addition of an ethoxy group axial on position 2. The charge was moved from equatorial 2 to axial 3, a move stabilised by the inclusion of a NH-link that can donate a hydrogen bond to the oxygen at axial 1. The stereo-chemical arrangement of functionalities on positions 1–3 now confers conformational rigidity to the structure, as well as a simplification of synthesis.

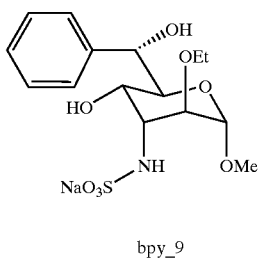

bpy_9

More dynamics were run, this time suggesting that bpy_9 would form a stable complex with the protein, similar to the way that was envisaged during the design.

Further Developments

By using reasoning in line with the above-described, more compounds have been designed (both from the hdo_family and from the bpy_family). The compounds of interest are those described by the general formulas I and II herein. The most promising compounds resulting from the analyses have been synthesized, cf. example 4.

In the further development of designed compounds using the above-described methods it has interestingly been found that the stability of the binding between the designed compounds and PapD seems to be only limitedly dependent on the interaction between the compound and the Arg-8 residue, even though Arg-8 is essential for the in vivo function of PapD. On the other hand, the stability of the interaction between the designed compounds and PapD is still very much dependent on the interaction with Lys-112 as well as with the β-strand. These observations confirm the surprising observation that the stable binding between PapD and pilus subunits is very much dependent on the interaction between the β-sheets of the two molecules.

Example 4

Synthesis of Compounds of the hdo Family Capable of Binding to the Binding Site of PapD General Methods $^1$H- and $^{13}$C-NMR spectra were recorded in CDCl$_3$ at 300 and 75 MHz respectively on a Varian Gemini 300 spectrometer unless otherwise stated. Signals from undeuterated solvent at 7.25 and 77.0 ppm respectively were used as internal reference signals. Optical rotations were measured using a Perkin Elmer 241 polarimeter.

Thin layer chromatography was performed on Merck DC-Fertig-platten (Kiselgel 60 F$_{254}$ 0.25 mm) and spots visualized by spraying with 10% sulphuric acid followed by charring at elevated temperature and/or spraying with molybdatophosphoric acid hydrate/Ce(SO$_4$)$_2$/dil. H$_2$SO$_4$ followed by heating (molybdatophosphoric acid hydrate=H$_3$[P(Mo$_3$O$_{10}$)$_4$]×H$_2$O, E.Merck, Darmstadt, Germany).

Ethyl 2,3-O-dibenzoyl-4-O-benzyl-1-thio-μ-D-glucohexopyranoside

Ethyl 2,3-O-dibenzoyl-4,6-O-benzylidene-1-thio-β-D-glucohexo-pyranoside (150 mg, 0.29 mmol) was dissolved together with borane-dimethylamine complex (68 mg, 1.16 mmol) in dry toluene (20 Å). Powdered 4 Å molecular sieves (180 mg) was added and the mixture was stirred at room temperature for 20 minutes. Aluminum trichloride (154 mg, 1.16 mmol) was added and after disappearance of the starting material (approx. 10 min., silica tlc toluene/acetonitrile 4:1) the mixture was filtered, treated with Dowex(H$^+$) ion-exchange resin until the solution was clear, and filtered again. The filtrate was concentrated and co-evaporated twice with methanol to yield 200 mg residue which upon chromatography on silica (toluene-acetonitrile 8:1) gave 60 mg, 40% of ethyl 2,3-O-dibenzoyl-4-O-benzyl-1-thio-β-D-glucohexopyranoside.

$^1$H-NMR (CDCl$_3$,δ): 8.0–7.2 (mm, 15H), 5.75 (t, 9.4 Hz, 1H, H3), 5.37 (t, 9.8 Hz, 1H, H2), 4.74 (d, 9.8 Hz, 1H, H1), 4.61 (s, 2H), 4.02–3.95 and 3.85–3.76 (2 bm, 2H, 2H6) 3.94 (t, 9.5 Hz, 1H, H4), 3.63 (ddd, 9.7 Hz, 3.9 Hz, 2.6 Hz, 1H, H5), 2.74 (2q, 7.5 Hz, 2H), 1.25 (t; 7.5 Hz, 3H).

Ethyl 6-O-acetyl-2,3-O-dibenzoyl-4-O-benzyl-1-thio-β-D-gluco-hexopyranoside

Ethyl 2,3-O-dibenzoyl-4-O-benzyl-1-thio-β-D-glucohexopyranoside (200 mg, 0.38 mmol) was dissolved in an ice-cooled mixture of pyridine and acetic anhydride (1:1, 6 Å). The mixture was stirred and attained at room temperature overnight. The mixture was diluted with dichloromethane, washed with satd. aq. sodium hydrogen carbonate and water and dried over sodium sulphate. The solvents were removed under reduced pressure and the residue was subjected to flash chromatography on silica gel (toluene-acetonitrile 6:1) to yield 204 mg, 93% of ethyl 6-O-acetyl-2,3-O-dibenzoyl-4-O-benzyl-1-thio-β-D-glucohexopyranoside.

$^1$H-NMR (CDCl$_3$, δ): 8.0–7.2 (mm, 15H), 5.75 (t, 9.2 Hz, 1H, H3), 5.40 (t, 9.8 Hz, 1H, H2), 4.71 (d, 10.0 Hz, 1H, H1) 4.59 and 4.55 (2d, 10.8 Hz, 2H, bzl-CH$_2$), 4.44 (dd, 12.0 Hz, 1.9 Hz, 1H, H6), 4.27 (dd, 12.2 Hz, 4.6 Hz, 1H, H6') 3.87 (t, 9.5 Hz, 1H, H4), 3.77 (ddd, 9.7 Hz, 4.6 Hz, 1.9 Hz, 1H, H5), 2.73 (m, 2H), 2.09 (s. 3H), 1.26 (t, 3H).

Methylglycolyl 6-O-acetyl-2,3-O-dibenzoyl-4-O-benzyl-β-D-glucohexopyranoside

6-O-Acetyl-2,3-O-dibenzoyl-4-O-benzyl-1-thio-β-D-glucohexopyranoside (600 mg, 1.04 mmol) and N-iodosuccinimide (468 mg, 2.08 mmol, dried 3 h, <0.1 mbar) were dissolved in dry acetonitrile (7 Å, passed through alumina) at room temperature. Methyl glycolate (161 μl, 2.08 mmol) was added and the mixture was stirred for 25 min at room temperature and then cooled on an ice-bath. Trifluoromethylsulphonic acid (18 μl, 0.21 mmol) was carefully added. Complete conversion of starting material had occurred after 10 minutes (tlc: silica toluene-acetonitrile 4:1). The reaction was quenched by addition of triethylamine, the mixture was diluted with dichloromethane, washed with water, sodium hydrogen carbonate and dried over sodium sulphate. The solvents were removed under reduced pressure and the residue subjected to chromatography on silica (toluene-acetonitrile 11:1) to yield 560 mg, 86% of ethyl 6-O-acetyl-2,3-O-dibenzoyl-4-O-benzyl-1-thio-β-D-glucohexopyranoside.

Ethyl 2,3-O-Dibenzoyl-4-O-benzyl-1-thio-β-D-glucohexopyranoside (hdo_9:1)

Ethyl 2,3-O-dibenzoyl-4,6-O-benzylidene-1-thio-βD-gluco-hexopyranoside (Chemical Abstracts, RN 149563-08-6 or Hällgren and Widmalm, 1993) was dissolved together with borane-dimethylamine complex (68 mg, 1.16 mmol) in dry toluene (20 ml) (reaction "a" in FIG. 6). Powdered 4 Å molecular sieves (180 mg) were added and the mixture was stirred at room temperature for 20 minutes. Aluminium trichloride (154 mg, 1.16 mmol) was added and after disappearance of the starting material (approx. 10 min., silica tlc toluene/acetonitrile 4:1) the mixture was filtered, treated with Dowex (H$^+$) ion-exchange resin until the solution was clear, and filtered again. The filtrate was concentrated and co-evaporated twice with methanol to yield 200 mg residue which upon chromatography on silica (toluene-acetonitrile 8:1) gave 60 mg, 40% of hdo_9:1.

$^1$H-NMR (CDCl$_3$,δ): 8.0–7.2 (mm, 15H), 5.75 (t, 9.4 Hz, 1H, H3), 5.37 (t, 9.8 Hz, 1H, H2), 4.74 (d, 9.8 Hz, 1H, H1), 4.61 (s, 2H), 4.02–3.95 and 3.85–3.76 (2 bm, 2H, 2H6) 3.94 (t, 9.5 Hz, 1H, H4), 3.63 (ddd, 9.7 Hz, 3.9 Hz, 2.6 Hz, 1H, H5), 2.74 (2q, 7.5 Hz, 2H), 1.25 (t; 7.5 Hz, 3H).

Ethyl 6-O-acetyl-2,3-O-dibenzoyl-4-O-benzyl-1-thio-β-D-gluco-hexopyranoside (hdo_9:2)

Ethyl 2,3-O-dibenzoyl-4-O-benzyl-1-thio-β-D-glucohexopyranoside (hdo_9:1) (200 mg, 0.38 mmol) was dissolved in an ice-cooled mixture of pyridine and acetic anhydride (1:1, 6 ml). The mixture was stirred and attained room temperature overnight. The mixture was diluted with dichloromethane and washed with saturated aqueous sodium hydrogen carbonate and water, dried over sodium sulphate. the solvents were removed under reduced pressure and the residue was subjected to flash chromatography on silica gel (toluene-acetonitrile 6:1) to yield 204 mg, 93% of hdo_9:2.

$^1$H-NMR (CDCl$_3$, δ): 8.0–7.2 (mm, 15H), 5.75 (t, 9.2 Hz, 1H, H3), 5.40 (t, 9.8 Hz, 1H, H2), 4.71 (d, 10. OHz, 1H, H1) 4.59 and 4.55 (2d, 10.8 Hz, 2H, bzl-CH2), 4.44 (dd, 12.0 Hz, 1.9 Hz, 1H, H6), 4.27 (dd, 12.2 Hz, 4.6 Hz, 1H, H6') 3.87 (t, 9.5 Hz, 1H, H4), 3.77 (ddd, 9.7 Hz, 4.6 Hz, 1.9 Hz, 1H, H5), 2.73 (m, 2H), 2.09 (s. 3H), 1.26 (t, 3H).

Methylglycolyl 6-O-acetyl-2,3-O-dibenzoyl-4-O-benzyl-βD-glu-cohexopyranoside (hdo_9:3)

6-O-acetyl-2,3-O-dibenzoyl-4-O-benzyl-1-thio-β-D-glucohexopyranoside (hdo_9:2) (600 mg, 1.04 mmol) and N-iodosuccinimide (468 mg, 2.08 mmol, dried 3h, <0.1 mbar) were dissolved in dry acetonitrile (7 ml, passed through alumina) at room temperature. Methyl glycolate (161 μl, 2.08 mmol) was added and the mixture was stirred for 25 min at room temperature and then cooled on an ice-bath. Trifluoromethylsulphonic acid (18 μl, 0.21 mmol) was carefully added. Complete conversion of starting material had occurred after 10 minutes (tlc: silica toluene-acetonitrile 4:1). The reaction was quenched by addition of triethylamine and the mixture was diluted with dichloromethane, washed with water, sodium hydrogen carbonate and dried over sodium sulphate. The solvents were removed under reduced pressure and the residue subjected to chromatography on silica (toluene-acetonitrile 11:1) to yield 560 mg, 86% of (hdo_9:3).

Sodium Glycolyl 4-O-benzyl-β-D-glucohexopyranoside (hdo_9)

Methylglycolyl 6-O-acetyl-2,3-O-dibenzoyl-4-O-benzyl-β-D-glucohexopyranoside (hdo_9:3) (350 mg, 0.59 mmol) was dissolved in 7 Å 25 mM sodium methoxide (methanol) and stirred at room temperature for 20 h or until only a very slow-moving spot could be detected on tlc by sulphuric acid charring (silica, toluene-acetonitrile 4:1). A small sample of this solution (=i) was retained as tlc reference before the methyl glycolate hydrolysis. Sodium hydroxide (15 mg) and water (200 μl) was added and stirring was continued for 8 h or until all "i" was consumed (tic silica, ethyl acetate-ethanol-acetic acid 8:3:1). The reaction was quenched by bringing the pH to 4.2 with acetic acid. The solvents were removed under reduced pressure and the residue (650 mg) was subjected to flash chromatography on silica (ethyl acetate-ethanol-acetic acid 8:3:1). The material in the R$_f$-range 0.15–0.25 was collected and concentrated to yield 178 mg, 92% of amorphous white solid.

$^1$HNMR (CD$_3$OD, δ relative to methanol at 3.31 ppm): 7.45 (m, 5H), 4.65 (d, 11.0 Hz, 1H), 4.36 (d, 16.0 Hz, 1H), 4.32 (d, 7.9 Hz, 1H, H1), 4.11 (d, 15.8 Hz, 1H), 3.82 (dd, 2.0 Hz, 12.1 Hz, 1H, H6), 3.65 (dd, 4.8 Hz, 12.1 Hz, 1H, H6), 3.59 (t, 9.0 Hz, 1H, H3 or H4), 3.40 (t, 9.1 Hz, 1H, H3 or H4)

This material still contained much acetic acid, so 50 mg was redissolved in water and freeze-dried to give 30 mg of substance free acetic acid but with a water content ($^1$H-NMR) of 24.5 mol. eq.

This material was again redissolved in water and 1 equivalent of sodium hydroxide was added, the solution was freeze-dried to give 22 mg of the title compound.

$^1$H-NMR (CD$_3$OD, δ relative to methanol at 3.31 ppm): 7.40–7.22 (m, 5H), 4.95 (d, 10.8 Hz, overlap by residual HDO at 4.93), 4.65 (d, 11.0 Hz, 1H), 4.34 (d, 16.0 Hz, 1H), 4.32 (d, 7.5 Hz, 1H, H1), 4.10 (d, 15.8 Hz), 3.82 (dd, 1.8 Hz, 11.9 Hz, 1H, H6), 3.66 (dd, 4.8 Hz, 12.1 Hz, 1H, H6), 3.59 (t, 8.8 Hz, 1H, H3), 3.41 (t, 9.7 Hz, 1H, H4), 3.15–3.06 (m, 2H, H5, H2).

$^{13}$C-NMR (CD$_3$OD, δ relative to methanol at 49.0 ppm): 176.1, 140.0, 129.3, 129.1, 128.6, 104.3, 79.1, 78.1, 77.2, 75.7, 75.2, 68.4, 62.3.

2-(Hydroxy)ethyl 4-O-benzyl-β-D-glucopyranoside (hdo_23)

A mixture of N-Iodosuccinimide (0.109 g, 0.484 mmol) and triflic acid (6.6 μl, 0.0744 mmol) in dichloroethane-diethyl ether (2 ml, 1:1) was added to a stirred mixture of the thioglycoside ethyl 6-O-acetyl-2,3-O-benzoyl-4-O-benzyl-1-thio-β-D-glucopyranoside (hdo_9:2) (0.210 g, 0.372 mmol), ethylen glycol (0.125 ml, 2.232 mmol), and molecular sieves (0.3 g, 4 Å) in dichloromethane-diethyl ether (3 ml, 1:2) at room temperature during 5 min. After 25 min TLC showed approx. 20% conversion of the thioglycoside, thus more N-Iodosuccinimide (0.109 g, 0.484 mmol) and triflic acid (6.6 μl, 0.0744 mmol) in dichloroethane-diethyl ether (2 ml, 1:1) was added during 5 min. After additional 30 min. the reaction mixture was filtered through a layer of Celite into an aqueous solution of sodium hydrogen carbonate and sodium bisulphite. The organic layer was separated, washed with water, dried (Na$_2$SO$_4$) and concentrated. The residue was coevaporeted twice with toluene, dissolved in methanol containing sodium methoxide (10 ml, 0.2 M), kept 1 h at 50° C., and evaporated. Column chromatography (SiO$_2$, chloroform-methanol-water, 100:15:1) of the residue gave hdo_23 (33 mg, 30%).

$[α]_D^{22}$+0.9° (c 1.4, methanol)

TLC: Rf 0.29 (chloroform-methanol-water, 100:15:1).

$^{13}$C-NMR (CD$_3$OD, δ: relative to methanol at 49.0 ppm) δ: 139.9, 129.2, 129.0, 128.6, 104,4 (C-1), 79.2, 78.2, 77.0, 75.7, 75.4, 72.3, 62.3, 62.3 ppm.

$^1$H-NMR (CD$_3$OD, δ: relative to methanol at 3.31 ppm)) δ: 7.45–7.25 (m, 5H), 4.95 (d, 11.0 Hz, 1H, benzylic),4.65 (d, 11.0 Hz, 1H, benzylic), 4.29 (d, 7.7, Hz, 1H, H-1) ppm.

Example 5

Synthesis of Compounds of the bpy Family Capable of Binding to the Binding Site of PapD Methyl 4'-methoxyphenylmethylene-α-D-mannohexopyranosides, Mixture of 4,6-, 2,3-endo and 2,3-exo Monoacetals (See: Patroni et al, 1988).

Methyl α-D-mannohexopyranoside (38.8 g, 200 mmol) and p-toluenesulphonic acid (200 mg) were dissolved in dimethylformamide (300 ml) and stirred at 100° C. under a nitrogen stream. 4-methoxy-benzaldehyde dimethyl acetal (37.7 g, 240 mmol) in dimethylformamide (300 ml) was added dropwise under 3h. Since starting material still remained (tlc, silica, ethyl acetate), stirring and heating was continued for 2 h. The composition of the reaction mixture did not show any visible change at that time (tic, silica, ethyl acetate) and the reaction was quenched with potassium carbonate (2.15 g). The solvent was removed under reduced pressure and the residue was filtered through silica (ethyl acetate) to remove salts and starting material. The concentrated eluents deposited monoacetals ($^1$H-NMR) on trituration with methyl t-butyl ether (11 g, 18%), which was collected by filtration. The filtrates were subjected to flash chromatography to yield additional 20 g of the monoacetal mixture (yield 51%) and 17 g of the 2,3;4,6-di acetals (endo/exo≈1:1).

Methyl 2-O-ethyl-4,6-O-(4'-methoxy)phenylmethylene-α-D-manno-hexopyranoside (bpy__9:1)

Methyl 4'-methoxyphenylmethylene-α-D-mannohexopyranosides, mixture of 4,6-, 2,3-endo and 2,3-exo monophenylmethylene acetals (11.3 g, 36.2 mmol), ethyl iodide (4.35 ml, 54.3 mmol) and tetrabutylammonium hydrogen sulphate (2.48 g, 7.24 mmol) were dissolved in methylene chloride (500 ml). To this was added a solution of sodium hydroxide (2.5 g, 140 mmol) in water (50 ml) and the mixture was heated at reflux for four days, with daily additions of ethyl iodide (2.4 ml) and 20% sodium hydroxide (1 ml). After this time, no visible change in the composition of the reaction mixture could be detected by tic (toluene-ethyl acetate 2:1). The mixture was allowed to cool, the phases separated and the organic phase washed with water (3x) and dried over sodium sulphate. The solvent was removed under reduced pressure and the residue was subjected to flash chromatography on silica gel (toluene-ethyl acetate 6:1). The fractions containing the component with $R_f$=0.40 on tlc (toluene-ethyl acetate 2:1) were pooled and recromatographed as above to yield 3.15 g, 26% of the title compound. Fractions containing components with $R_f$=0.32 on tlc were found to consist of a mixture of monoethylated monophenylmethylene acetal regio-isomers ($^1$H-NMR).

$[\alpha]_D^{20}$=+11.2° (c1.02, CHCl$_3$)

$^1$H-NMR (CDCl$_3$, δ): 7.42 (symm.m, 2H), 6.88 (symm.m, 2H), 5.53 (s, 1H), 4.77 (d, 1.3 Hz, 1H, H1), 4.24 (dd, 4.2 Hz, 9.7 Hz, 1H, H6), 4.02 (dt, 4.0 Hz, 8.8 Hz, 1H, H5), 3.83 (dd, 1.8 Hz, 9.7 Hz, 1H, H6), 3.80–3.69 (s and overl.m, 6H, 1-OMe, H3, H4, 2-O—C$\underline{H}$HCH$_3$), 3.66 (dd, 1.3 Hz, 3.7 Hz, 1H, H2), 3.64–3.55 (m, 1H, 2-O—CH$\underline{H}$CH$_3$), 3.69 (s, 3H, Ar-OMe), 2.48 (d, 1H, OH), 1.26 (t, 7.0 Hz, 3H, 2-O—CH$_2$C$\underline{H}_3$).

$^1$H-NMR (CDCl$_3$, with added Cl$_3$CCONC, δ): 8.54 (s, 1H, acylcarbamate NH), 7.38 (symm.m, 2H), 6.88 (symm.m, 2H), 5.52 (s, 1H), 5.27 (dd, 3.5 Hz, 10.3 Hz, 1H, H3), 4.76 (d, 1.6 Hz, 1H, H1), 4.32–4.20 (m, 1H), 4.13 (symm.m, 1H, H5), 3.97 (dd, 1.8 Hz, 3.5 Hz, 1H, H2), 3.91–3.80 (m, 1H), 3.79 (s, 3H, 1-OMe), 3.77–3.54 (m, 3H), 3.41 (s, 3H, Ar-OMe), 1.23 (t, 7.0 Hz, 3H).

$^{13}$C-NMR (CDCl$_3$, δ): 160.1, 129.9, 127.6, 113.6, 102.0, 99.3, 79.4, 78.8, 68.7, 68.3, 67.2, 63.2, 55.2, 54.9, 15.4.
Calc. for C$_{17}$H$_{25}$O$_7$: C: 59.8H: 7.38, Methyl 2-O-ethyl-3-O-dimethyl-t-butylsilyl-4,6-O-(4'-methoxy)phenylmethylene-α-D-mannohexopyranoside (bpy__9:2)

Methyl 2-O-ethyl-4,6-O-(4'-methoxy)phenylmethylene-α-D-mannohexopyranoside (bpy__9:1) (0.98 g, 2.88 mmol) was dissolved in dry methylene chloride (18 ml) together with triethyl amine (600 μl, 4.32 mmol) and the mixture was ice-cooled. t-Butyl-dimethylsilyl trifluromethyl sulphonate (795 μl, 3.45 mmol) in methylene chloride (2 ml) was added dropwise and the reaction mixture with the cooling bath was left at ambient temperature overnight (tlc silica toluene-methyl t-butyl ether 4:1). The excess silylating reagent was destroyed by addition of methanol (3 ml), the mixture was concentrated under reduced pressure and the residue was subjected to flash chromatography on silica (toluene-methyl t-butyl ether 40:1) to yield 1.40 g, 100% of (bpy__9:2).

$^1$H-NMR (CDCl3, δ): 7.40 (symm.m, 2H), 6.87 (symm.m, 2H), 5.53 (s. 1H), 4.70 (d, 1.3 Hz, 1H, H1), 4.21 (dd, 4.6 Hz, 9.9 Hz, 1H, H6), 4.10 (dd, 3.3 Hz, 9.7 Hz, 1H, H3), 3.91 (t, 9.5 Hz, 1H, H4), 3.90–3.79 (s overl. m, 5H, H6,2-OC$\underline{H}$HCH$_3$;1-OMe), 3.76–3.63 (m, 2H, H5, 2-OCH$\underline{H}$CH3), 3.55 (dd, 1.5 Hz, 3.3 Hz, 1H, H2), 3.67 (s, 3H, Ar-OMe), 1.24 (t, 7.0 Hz, 3H), 0.88 (s, 9H), 0.08 (s, 3H), 0.03 (s, 3H).

$^{13}$C-NMR (CDCl$_3$, δ): 159.9, 130.3, 127.5, 113.4, 101.8, 101.2, 79.9, 79.1, 70.3, 68.8, 68.2, 64,1, 55.2, 54.8, 25.8, 18.3, 15.6,–4.4,–4.9.

Methyl 2-O-ethyl-3-O-dimethyl-t-butylsilyl-4,-O-(4'-methoxy)-benzyl-α-D-mannohexopyranoside (bpy__9:3) and methyl 2-O-ethyl-3-O-dimethyl-t-butylsilyl-6-O-(4'-methoxy)-benzyl-α-D-mannohexopyranoside (bpy__9:8)

Methyl 2-O-ethyl-3-O-dimethyl-t-butylsilyl-4,6-O-(4'-methoxy)phenylmethylene-α-D-mannohexopyranoside (bpy__9:2) (3.61 g, 7.95 nmol) was dissolved in acetonitrile (150 ml, dried over 4 Å molecular sieves), powdered 3 Å molecular sieves (6 g) was added and the mixture cooled to −30° C. under a nitrogen atmosphere and stirred for 15 min. Sodium cyanoborohydride (3.04 g, 47.7 mmol) was added and a solution of chlorotrime-thylsilane (7.95 ml, 47.7 mmol) in dry acetonitrile (50 ml, dried over 4 Å molecular sieves) was added dropwise in 1 h. Stirring was continued for 2 h at −30° C., whereafter the temperature was allowed to rise to 0° C. After 1 h tic (toluene-ethyl acetate 4:1) showed complete conversion of starting material. The mixture was filtered through a Celite® pad, the Celite® washed thoroughly with ethyl acetate. The combined filtrates were washed with aq. satd. sodium hydrogen carbonate, aq. satd. sodium chloride, concentrated under reduced pressure, redissolved in toluene and concentrated under reduced pressure. The residue was subjected to flash chromatography on silica (toluene-ethyl acetate 4:1, then 1:1) to obtain bpy__9:8 (=bpy__21:1) 578 mg, 16% and (bpy__9:3) 2.34 g, 65%.

bpy__9:3 (some assignments from COSY, HETCOR):

$^1$H-NMR (CDCl$_3$, δ): 7.25 (symm.m 2H), 6.87 (symm.m, 2H), 4.81 (d, 11.0 Hz, 1H), 4.66 (d, 1.8 Hz, 1H, H1), 4.51 (d, 10.8 Hz, 1H), 4.02 (dd, 3.1 Hz, 5.9 Hz, 1H, H3), 3.80 (s, 3H, 1-OMe), 3.79–3.60 (m, 5H, H4, 2H6, 2-OCH$_2$CH$_3$), 3.54 (ddd, 2.9 Hz, 4.8 Hz, 9.7 Hz, 1H, H5), 3.46 (dd, 2.0 Hz, 3.3 Hz, 1H, H2), 3.33 (s, 3H, Ar-OMe), 2.10 and 1.86 (2 v.br.s, ≈1H, 6-OH), 1.23 (t, 6.8 Hz, 3H), 0.95 (s, 9H), 0.12 (s 6H).

$^1$H-NMR (CDCl$_3$, with added Cl$_3$CCONC, δ): 8.40 (s, 1H, acylcarbamate NH), 7.24 (symm.m, 2H, Ar H3',5'), 6.86 (symm.m, 2H, Ar H2', H6'), 4.82 (d, 11.2 Hz, 1H), 4.67 (d, 2.0 Hz, 1H, H1), 4.43–4.32 (m, 2H, 2H6), 4.08–3.98 (m, 1H, H3), 3.78 (s, 3H, 1-OMe), 3.77–3.61 (m, 4H, H5, 2-OC$\underline{H}_2$CH$_3$, H4), 3.46 (dd, 1.8 Hz, 3.1 Hz, 1H, H2), 3.34 (s, 3H, Ar-OMe), 1.22 (t, 7.0 Hz, 3H), 0.96 (s, 9H), 0.14 (s, 3H), 0.13 (s, 3H).

$^{13}$C-NMR (CDCl$_3$, δ): 159.1, 130.7, 129.3, 113.8, 99.8, 79.5, 75.7, 74.7, 73.0, 72.2, 67.4, 62.5, 55.2, 54.7, 18.0, 15.7, 4.3, −4.6.

$^{13}$C-NMR (CDCl$_3$, with added Cl$_3$CCONC, δ): 159.3 (Ar C4'), 157.4, 149.3, 130.2 (Ar C2'), 129.6 (Ar C3',C5'), 113.8 (Ar C2',C6'), 99.6 (Cl), 79.2 (C2), 74.56* (4-OCH$_2$Ar or 2—C$\underline{H}_2$CH$_3$), 74.54* (4-OCH$_2$Ar or 2—C$\underline{H}_2$CH$_3$), 73.2 (C3), 69.7 (C5), 67.2 (C4), 66.3 (C6), 55.2 (1-OMe), 54.9 (Ar-OMe), 25.9 (CMe$_3$), 18.0 (C$\underline{M}$e$_3$), 15.6, −4.3, −4.7.

bpy__9:8:

$^1$H-NMR (CDCl$_3$, δ): 7.28 (symm.m, 2H), 6.86 (symm.m, 2H), 4.70 (d, 1.8 Hz, IH, HI), 4.55 (d, 11.7 Hz, 1H, H6), 4.51 (d, 11.6 Hz, 1H, H6), 3.89–3.55 and 3.79 (m and s, 7H, H3, H4, H5, 2-OC$\underline{H}_2$CH$_3$, 1-OMe), 3.44 (dd, 1.8 Hz, 2.9 Hz, 1H, H2), 3.56 (s, 3H, Ar-OMe), 2.29 (d, 2.0 Hz, 1H, 4-OH), 1.20 (t, 7.0 Hz, 3H), 0.92 (s, 9H), 0.13 (s, 3H), 0.12 (s, 3H).

$^{13}$C-NMR (CDCl$_3$, δ): 159.1, 130.3, 129.3, 113.7, 99.7, 78.9, 73.19*, 73.16*, 71.3, 70.3, 69.1, 67.2, 55.2, 54.8, 25.8, 18.2, 15.6, −4.5, −4.6.
*resolved by multiplying the FID with a gaussian weigth-function.

Methyl 2-O-ethyl-3-O-dimethyl-t-butylsilyl-4,-O-(4'-methoxy)-benzyl-6(S)-phenyl-α-D-mannohexopyranoside (bpy_9:4)

(Oxidation ref. D. F. Taber et al, J. Org. Chem. 52, 5621–2, 1987) Methyl 2-O-ethyl-3-O-dimethyl-t-butylsilyl-4, —O-(4'-methoxy)benzyl-α-D-mannohexopyranoside (bpy_9:3) (200 mg, 0.438 mmol) and dimethylsulphoxide (64.0 μl, 0.876 mmol) were dissolved in dichloromethane (2.5 ml, dried over 4 Å molecular sieves) and the solution was cooled on an ice-bath. Phosphorpentoxide (124 mg, 0.876 mmol) was added quickly and the resulting stirred suspension was allowed to attain RT (1 h). The mixture was again ice-cooled and triethyl amine (215 μl, 1.53 mmol) was added causing an immediate dissolution of the gel-like suspension. The ice-bath was removed and the mixture was stirred at RT for 1 h, the diluted with ethyl acetate, washed with aq. 0.2 M sodium dihydrogen phosphate, dried over sodium sulphate and concentrated under reduced pressure (<0.02 mbar). The residue was dissolved tetrahydrofurane (2 ml, dried over 4 Å molecular sieves), stirred and cooled to −20° C. Phenylmagnesium chloride in tetrahydrofurane (345 μl of a 25 w % solution, 0.657 mmol, Janssen, Belgium) was added dropwise (3 min). The reaction was monitored with tlc (toluene-ethyl acetate 4:1) and quenched with aq. 10% ammonium sulphate (3 ml). The mixture diluted with ethyl acetate and washed twice with water, dried over sodium sulphate and concentrated under reduced pressure. The residue was subjected to flash chromatography on silica (toluene-methyl t-butyl ether 20:1). The fractions containing the component with a $R_f$=0.44 on tlc (toluene-ethyl acetate 4:1) were pooled and concentrated under reduced pressure to yield 65 mg, 30% of the title compound.

Molecular mechanics calculations with MM2(91) (Burkert and Allinger, 1982) of the R and S diastereomers and subsequent calculations with Karplus equation (Bothner-By, 1965) predicted that the $^1$H-NMR $J_{5-6}$ would be 4.8 and 6.2 respectively. This difference is too small to be but an indication of the stereochemistry. Furthermore, the H6 signal is poorly resolved and the H5 signal is severely overlapped by other resonances. The $^1$H-COSY H4–H5 crosspeak, however, contains the sum $J_{4-5}+J_{5-6}$ and since the $J_{4-5}$ is observable in the H4-resonance, the $J_{5-6}$ can be assigned the value 6.8 Hz. This indicates that the isolated product has the 6-(S) stereochemistry.

After the removal of the 4-methoxybenzyl group the calculated coupling constants become 5.5 Hz and 12.9 Hz, respectively.

$^1$H-NMR (CDCl$_3$, δ): 7.44–7.19 (m, 7H), 6.89 (symm.m, 2H), 5.00 (br.m, 1H, H6), 4.90 (d, 10.8 Hz, 1H), 4.66 (d, 10.8 Hz, 1H), 4.58 (d, 1.8 Hz, 1H, H1), 4.04 (dd, 3.1 Hz, 9.0 Hz), 3.99 (t, 9.2 Hz, 1H, H4), 3.81 and 3.82–3.56 (s and m, 6H, 1-OMe, 2-CH$_2$CH$_3$), H5), 3.44 (dd, 2.0 Hz, 2.9 Hz, 1H, H2), 2.84 (s, 3H, Ar-OMe), 1.24 (t, 3H), 1.97 (s, 9H), 0.15 (s, 3H), 0.13 (s, 3H).

$^{13}$C-NMR (CDCl$_3$, δ): 159.0, 142.5, 130.8, 129.2, 127.7, 126.7, 126.6, 125.7, 113.7, 99.5, 79.8, 76.1, 74.5, 73.0, 70.9, 67.9, 55.1, 54.1, 25.8, 17.9, 15.4, −4.5, −4.8.

Methyl 2,3-anhydro-4,6-O-p-methoxybenzylidene-α-D-mannopyranoside (bpy_9:9)

To a stirred suspension of sodium hydride (2.6 g, 65 mmol, 65% dispersion in mineral oil) in N,N-dimethylformamide (150 ml) was added with stirring a solution of methyl 4,6-O-p-methoxybenzylidene-α-D-glucopyranoside (9.36 g, 30 mmol) in N.N-dimethylformamide (65 ml). The mixture was stirred to 45 minutes and p-toluenesulfonylimidazol (7.24 g, 33 mmol was added. Stirring was continued for 2 hours and the mixture was the poured into ice-water. The precipitate was filtered of, dried in vacuo to give crude bpy_9:) (7.7 g). Recrystallization twice form methanol (250 ml gave bpy_9:9 (3.58 g). Chromatography (SiO$_2$, ethyl acetate-heptane, 2:3) of the mother liquor followed by crystallization form methanol (150 ml) gave additional bpy_9:9 (1.87 g). The total yield of bpy_9:9 was 5.45 g (61%).

m.p. 152–153.5° C. (methanol)
$[α]_D^{22}$: 96.40 (c 1.8, chloroform)
$^1$H NMR (CDCl$_3$) δ: 7.43 and 6.91 (AB pattern, further coupled, 2H, $J_{AB}$=8.7 Hz), 5.53 (s, 1H, ArCH), 4.90 (s, 1H, H-1), 4.30–4.19 (sym.m, 1H) 3.82 (s, 3H, CH$_3$OAr), 3.78–3.64 (3H), 3.49–3.46 (4H), 3.48 (s, 3H, CH$_3$0), 3.18 (d, 1H, J 3.7=Hz, H-2/H-3) ppm.
$^{13}$C NMR (CDCl$_3$) δ: 160.3, 129.6, 127.5, 113.7, 102.4, 96.9, 74.8, 69.4, 61.7, 55.7, 55.3, 53.8 and 50.5 ppm.

Methyl 3-azido-4,6-O-p-methoxybenzylidene-α-D-altropyranoside (bpy_9:10)

Methyl 2,3-anhydro-4,6-O-p-methoxybenzylidene-α-D-mannopyranoside (bpy_9:9, 2.35 g, 8 mmol), sodium azide (2.08 g, 32 mmol) and ammonium chloride (0.86 g, 16 mmol) was stirred for 5 hours at 110° C. in a mixture of 2-methoxyethanol (25 ml) and water (5 ml). The suspension gradually dissolved to give a turbid solution. The mixture was then partitioned between ethyl acetate and aqueous NaOH (0.25 M, 100 ml). The aqueous phase was extracted twice with ethyl acetate and the combined organic phases was washed twice with water and than with saturated aqueous NaCl, dried (Na$_2$SO$_4$), filtered and concentrated. Chromatography. (SiO$_2$) ethyl acetate-heptane, 2:3–2:1) gave bpy_9:10 (1.97 g, 73%). An analytical sample was crystallized from ethyl acetate-heptane.

m.p. 91–93° C. (EtOAc/Heptane)
$[α]_D^{22}$: +26.10 (c 1.1, chloroform)
$^1$H NMR (CDCl$_3$) δ: 7.44 and 6.91 (AB pattern further coupled, 2H, $J_{AB}$=8.6 Hz), 5.57 (s, 1H, ArCH), 4.56 (s, 1H, H-1), 4.43–4.21 (2H), 4.16–4.08 (1H), 4.03 (unresolved dd, 1H, $J_1=J_2$=3 Hz), 3.91 (bs, 1H, H-2), 3.83–3.74 (4H), 3.80 (s, 3H, CH$_3$O), 3.43 (s, 3H, CH$_3$0), 2.36 (bs, 1H, OH) ppm.
$^{13}$C NMR (CDCl$_3$) δ: 160.3, 129.5, 127.5, 113.7, 102.3, 101.4, 75.8, 69.8, 69.0, 60.1, 59.0,55.7 and 55.3 ppm.

Acetylation (acetic anhydride-pyridine, 3:5) of a sample of bpy_9:10 gave an acetate which had the following $^1$H NMR spectrum (assignments were confirmed by the corresponding homonuclear COSY spectrum):

$^1$H NMR (CDCl$_3$) δ: 7.43 and 6.91 (AB pattern further coupled, 2H, $J_{AB}$=8.8 Hz), 5.59 (s, 1H, ArCH), 4.97 (dd, 1H, J=2.2 and 0.9 Hz, H-2), 4.57 (s, 1H, H-1), 4.36 (2H, H-6 and H-4), 4.09–4.01 (2H, H-6, and H-3), 3.84–3.74 (2H, CH$_3$O and H-5), 3.81 (s, 3H, CH$_3$O), 3.44 (s, 3H, CH$_3$O), 2.15 (s, 3H, CH$_3$CO)

Methyl 3-azido-2-O-ethyl-4,6-O-p-methoxybenzylidene-α-D-altropyranoside (bpy_9:11)

Methyl 3-azido-4,6-O-p-methoxybenzylidene-α-D-altropyranoside (bpy_9:10, 1.7 g, 5 mmol), barium oxide (3.0 g, 19.6 mmol) and ethyl iodide (5 ml, 62 mmol) was stirred in dimethyl sulphoxide (5 ml). Water (10 μl) was added and the stirring was continued for 16 hours. The mixture was then partitioned between ethyl acetate and water. The aqueous phase was extracted twice with ethyl acetate and the combined organic phases was washed twice with water and then with saturated aqueous NaCl, dried (Na$_2$SO$_4$), filtered and concentrated. Chromatography (SiO$_2$, ethyl acetate-heptane, 1:3) gave bpy__9:11 as an oil (1.7 g, 92%).

[α]$_D^{22}$: 19.1° (c 1.6, chloroform).

$^1$H NMR (CDCl$_3$) δ: 7.44 and 6.91 (AB pattern, further coupled, 2H, J$_{AB}$=8.6 Hz), 55.57 (s, 2H, ArC$\underline{H}$), 4.63 (bs, 1H, H-1), 4.14–4.06 (2H), 3.85–3.75 (4H), 3.81 (s, 3H, CH$_3$O), 3.73–3.56 (sym.m.2H), 3.52 (dd, 1H, J=2.4 and 0.9 Hz, H-3), 3.34 (s, 3H, CH$_3$O), 1.25 (t, 3H, J=6.9 Hz, CH$_3$CH$_2$) ppm.

$^{13}$C NMR (CDCl$_3$) δ: 160.1, 129.6, 127.4, 113.6, 102.1, 99.6, 77.0, 76.1, 69.0, 66.5, 58.7, 58.1, 55.5, 55.2 and 15.3 ppm.

Methyl 3-azido-3-deoxy-2-O-ethyl-4-O-p-methoxybenzyl-α-D-altro-pyranoside (Cf. R. Johansson and B. Samuelsson; *J. Chem. Soc. Commun.* 1984, 201–202).

Methyl 3-azido-3-deoxy-2-O-ethyl-4,6-O-p-methoxybenzylidene-α-D-altropyranoside (bpy__9:11) (2.41 g, 6.6 mmol), sodium cyanoborohydride (2.5 g, 39.6 mmol) and ground molecular sieves (5 g) was stirred in acetonitrile (130 ml) at 0° C. A solution of trimethylsilyl chloride (5.0 ml, 40 mmol) in acetonitrile (45 ml) was added during 55 min. After additional 1.5 h of stirring, the cooling bath was removed and the stirring was continued for 21 h. The mixture was filtered through celite and the filtrate was partitioned between ethyl acetate and saturated aqueous NaHCO$_3$. The organic phase was washed twice with saturated aqueous NaHCO3 and then with saturated aqueous NaCl, dried (Na$_2$SO$_4$+NaHCO$_3$), filtered and evaporated. Chromatography twice (SiO$_2$, ethyl acetate-heptane 2:7→2:1 and ethyl acetate-toluene 1:2→2:1) gave the title compound (2.23 g, 92%) as an oil.

[α]$_D^{22}$: +113.60 (c 1.4, chloroform)

$^1$H NMR data (CDCl$_3$) δ: 7.30 and 6.89 (AB pattern, further coupled, 4H, J=8.8 Hz), 4.62 and 4.56 (AB pattern, 2H, J=11.3 Hz, benzylic H), 4.58 (unresolved d, virtually coupled, 1H, J<2 Hz, H-1), 4.00–3.84 (3H, H-3, H-4 and H-5), 3.81 (s, 3H, CH$_3$OAr), 3.84–3.7 (2H, H-6), 3.62–3.43 (3 H, C$\underline{H}_2$CH$_3$ and H-2), 3.38 (s, 3H, CH$_3$0), 1.99 (bs, 1H, OH) and 1.19 (t, 3H, J=7.0 Hz, CH$_2$C$\underline{H}_3$) ppm.

$^{13}$C NMR data (CDCl$_3$) δ: 159.6, 129.9, 129.6, 113.9, 99.9, 76.9, 72.2, 71.9, 67.7, 66.3, 62.4, 58.6, 55.4, 55.3 and 15.4 ppm.

Methyl 3-azido-6-O-benzoyl-3-deoxy-2-O-ethyl-4-O-p-methoxy-benzyl-α-D-altropyranoside A solution of methyl 3-azido-3-deoxy-2-O-ethyl-4-O-p-methoxy-benzyl-α-D-altro-pyranoside (1.47 g, 4 mmol) in pyridine (35 ml) was stirred at 0° C. Benzoyl chloride (1.2 ml, 10.3 mmol) was added and the temperature was raised to room temperature. The stirring was continued for 1.5 h and the mixture was then cooled to 0° C. Methanol (10 ml) was added and the mixture was stirred for additional 20 min. at room temperature, evaporated and partitioned between ethyl acetate and water. The organic phase was washed subsequently with water, saturated aqueous NaHCO$_3$, water, saturated aqueous NaCl, dried (Na$_2$SO$_4$), filtered and evaporated. Chromatography (SiO$_2$, ethyl acetate-heptane 1:4) gave the benzoate (1.64 g, 87%).

[α]$_D^{22}$: +0.95° (c 1.0, chloroform)

$^1$H NMR data (CDCl$_3$) δ: 8.04–7.98 (m, 2H), 7.56 (tt, 1H, J=7.5 and 1.3 Hz), 7.43 (t, further coupled, 2H, J=7.5 Hz), 7.26 and 6.83 (AB pattern, further coupled, 4H, J=8.6 Hz), 4.62 and 4.50 (AB pattern, 2H, J=11.3 Hz, ArC$\underline{H}_2$), 4.63 (d, further coupled, J=1.3 Hz, H-1), 4.54 (A part of an ABX system, 1H, J=11.8 and 2.7 Hz, H-6$_a$), 4.47 (B part of an ABX system, 1H, J=11.8 and 5.5 Hz, H-6$_b$), 4.27 (ddd, 1H, J=8.4, 5.5 and 2.7 Hz, H-5), 3.99–3.92 (2H, H-3 and H-4), 3.74 (s, 3H, CH$_3$OAr), 3.67–3.48 (3H, C$\underline{H}_2$CH$_3$ and H-2) and 1.22 (t, 3H, J=7.0 Hz, CH$_2$C$\underline{H}_3$) ppm.

$^{13}$C NMR data (CDCl$_3$) δ: 166.2, 159.5, 132.9, 130.1, 129.9, 129.6, 129.2, 128.3, 113.9, 99.6, 76.72, 72.0, 71.7, 62.3, 62.2, 64.1, 58.5, 55.4, 55.2 and 15.4 ppm.

Methyl 6-O-benzoyl-3-deoxy-2-O-ethyl-4-O-p-methoxybenzyl-3-sulfamino-α-D-altropyranoside sodium salt (Cf. H. P. Wessel; *J. Carbohydr. Chem.* 11 (8), (1992), 1039–1052).

To a stirred solution of methyl 3-azido-6-O-benzoyl-3-deoxy-2-O-ethyl-4-O-p-methoxybenzyl-α-D-altropyranoside (620 mg, 1.31 mmol) in tetrahydrofuran (40 ml) was added water (265 ml) and triphenylphosphine (1.7 g, 6.5 mmol). The solution was stirred for 24 h and was then concentrated to 12 ml. The residue was diluted with methanol (10 ml) and water (3 ml). To the stirred solution was then added trimethylamine sulfurtrioxide complex (370 mg, 2.7 mmol). The pH was adjusted to 8.5 by 1 M aqueous NaOH. After a few minutes a precipitate was formed, which was dissolved by adding tetrahydrofuran (3 ml) and methanol (4 ml). The reaction mixture was stirred for 0.5 h, after which time additional trimethylamine sulfurtrioxide complex (86 mg) was added. The stirring was continued for 15 min. During the course of the reaction pH was kept at 8–9 by adding 1 M aqueous NaOH. The mixture was then diluted with water (7 ml) and the organic solvents were evaporated under reduced pressure. Additional water (5 ml) was added and the suspension was lyophilised and chromatographed (SiO$_2$, chloroform-methanol-water 100:15:1→70:30:5) to give the sulfamino compound, presumably in the sodium salt form, (668 mg, 92%) after lyophilisation from water. A sample was crystallized from aqueous acetone.

m.p. 112–115° C. (aqueous acetone).

[α]$_D^{22}$: +156.4° (c 0.5, water)

$^1$H NMR data (CD$_3$OD) δ: 7.94–7.89 (m, 2H), 2H, 7.64–7.56 (m. 1H), 7.44 (m, 2H), 7.28 and 6.73 (AB pattern, further coupled, 4H, J=8.6 Hz), 4.71 and 4.49 (AB pattern, 2H, J=11.4 Hz, ArC$\underline{H}_2$), 4.68 (bs, 1H, H-1), 4.51 (dd, 1H, J=11.6 and 2.4 Hz, H-6$_a$), 4.44 (dd, 1H, J=11.6 and 4.4 Hz, H-6$_b$), 4.09 (unresolved ddd, 1H, J≈4, 3 and 1 Hz, H-3), 4.00–3.92 (2H, H-5 and H-2), 3.86 (dd, 1H, J=9.9 and 4.2 Hz, H-4), 3.71–3.54 (5H, C$\underline{H}_2$CH$_3$ and CH$_3$OAr), 3.65 (s, CH$_3$OAr), 3.40 (s, 3H, CH$_3$O) and 1.17 (t, 3H, J=7.0 Hz, CH$_2$C$\underline{H}_3$) ppm.

$^{13}$C NMR data (CD$_3$OD) δ: 167.8, 160.8, 134.2, 131.4, 130.9, 130.6, 129.5, 114.7, 101.6, 77.03, 70.02, 69.2, 67.0, 66.4, 65.2, 5S.6, 55.5, 50.6 and 15.8 ppm.

Methyl 6-O-benzoyl-3-deoxy-2-O-ethyl-3-sulfamino-α-D-altropyranoside ammoniumn salt (bpy__30)

Methyl 6-O-benzoyl-3-deoxy-2-O-ethyl-4-O-p-methoxybenzyl-3-sulfamino-α-D-altro-pyranoside sodium salt (334 mg, 2.0 mmol) was hydrogenolysed for 6 h in glacial acetic acid (55 ml) at 0.23 MPa and room temperature, using 5% palladium on charcoal as a catalyst. Filtering and lyophilisation gave a residue which was chromatographed (SiO$_2$, chloroform-methanol-water 100:15:1→70:30:5). The product was dissolved in water and passed through a cation exchange resin (BIO-REX® 70, 200–400 mesh, ammonium form) and lyophilised to give the title compound (222 mg, 86%).

[α]$_D^{22}$: +55.7° (c 1.3, water)

$^1$H NMR data (pyridine-d$_5$) δ: 8.23–8.17 (2H), 7.52–7.45 (1 H), 7.42–7.35 (2H), 5.09 (dd, 1H, J=11.65 and 1.54 Hz, H-6$_a$), 4.82 (dd, 1H, J=11.43 and 6.81 Hz, H-6$_b$), 4.82 (s, 1 H, H-1), 4.66 (unresolved dd, 1H, J≈3.5 and 3.5 Hz, H-3), 4.36 (dd, 1H, J=10.11 and 3.96 Hz, H-4), 4.32–4–23 (1H, H-5), 4.18 (d, 1H, J=3.08 Hz, H-2), 3.60–3.44 (2H, C$\underline{H}_2$CH$_3$), 3.16 (s, 3H, CH$_3$O) and 1.00 (t, 3H, J=7.0 Hz, CH$_2$CH$_3$) ppm.

$^1$H NMR data (D$_2$O, ref. acetone at 2.35 ppm) δ: 8.22–8.17 (2 H), 7.83 (tt, 1H, J=7.5 and <2 Hz), 7.72–7.65 (2H), 4.97 (HDO), 4.93 (s, 1H, H-1), 4.81 (dd, virtually coupled, 1H, J=12 and 1.7 Hz, H-6$_a$), 4.65 (dd, virtually coupled, 1H, J=12 and 5.5 Hz, H-6$_b$), 4.18–4–15 (2H, h-4 and H-5), 4.05 (dd, 1H, J=3.3 and 1.4 Hz, H-2), 3.95–3.75 (sym. m. 2H, C$\underline{H}_2$CH$_3$), 3.94–3.91 (m, 1H, H-3), 3.54 (s, 3H, CH$_3$O) and 1.35 (t, 3H, J=7 Hz, CH$_2$C$\underline{H}_3$) ppm (the assignments of the $^1$H NMR spectrum signals were made on the basis of a COSY experiment).

$^{13}$C NMR data (D$_2$O, ref.: acetone at 33.19 ppm) δ171.4, 136.9, 132.5, 132.1, 131.7, 102.5, 78.4, 69.9, 69.1, 67.4, 65.7, 58.1, 56.0 and 17.5 ppm.

Methyl 3-azido-6-O-pivaloyl-3-deoxy-2-O-ethyl-4-O-p-methoxy-benzyl-α-D-altropyranoside A solution of methyl 3-azido-3-deoxy-2-O-ethyl-4-O-p-methoxy-benzyl-α-D-altro-pyranoside (476 mg, 1.3 mmol) in pyridine (8 ml) was stirred at 0° C. Pivaloyl chloride (390 μl, 3.25 mmol) was added and the temperature was raised to room temperature. The stirring was continued for 1.5 h and the mixture was then cooled to 0° C. Methanol (10 ml) was added and the mixture was stirred for additional 20 min. at room temperature, evaporated and partitioned between ethyl acetate and water. The organic phase was washed subsequently with water, saturated aqueous NaHCO$_3$, water, saturated aqueous NaCl, dried (Na$_2$SO$_4$), filtered and evaporated. Chromatography (SiO$_2$, methyl tert-butyl ether-heptane 1:4) and (C-18 Lobar, Merck, acetonitrile-water 4:1) gave the pivaloate (431 mg, 75%).

$^1$H NMR data (CDCl$_3$) δ: 7.28 and 6.89 (AB pattern, further coupled, 4H, J=8.6 Hz), 4.60 and 4.49 (AB pattern, 2H, J=11.0 Hz, ArC$\underline{H}_2$), 4.57 (s, 1H, H-1), 4.39 (dd, 1H, J=14.5 and 5.3 Hz, H-6$_a$), 4.13 (2H, H-6$_b$ and H-4), 3.93 (m, 1H, H-3), 3.84–3.78 (4H, H-S and MeOAr), 3.64–3.45 (3H, C$\underline{H}_2$CH$_3$ and H-2), 3.39 (s, 3H, 1-OMe) and 1.22–1.15 (s and t, 12H, J=7.0 Hz, C(CH$_3$)$_3$ and CH$_2$C$\underline{H}_3$) ppm.

$^{13}$C NMR data (CDCl$_3$) δ: 178.1, 159.6, 129.9, 129.3, 113.9, 99.5 (C-1), 76.7 (C-2), 72.5 (C-5), 71.9 (ArC$\underline{H}_2$), 66.4 (C-4), 66.2 (C$\underline{H}_2$CH$_3$), 63.6 (C-6), 58.5, 55.3, 55.2, 38.8, 27.2 and 15.4 ppm.

Methyl 6-O-pivaloyl-3-deoxy-2-O-ethyl-4-O-p-methoxybenzyl-3-sulfamino-α-D-altropyranoside sodium salt (Cf. H. P. Wessel; *J. Carbohydr. Chem.* 11 (8), (1992), 1039–1052.]

To a stirred solution of methyl 3-azido-6-O-pivaloyl-3-deoxy-2-O-ethyl-4-O-p-methoxybenzyl-α-D-altropyranoside (300 mg, 0.683 mmol) in tetrahydrofuran (20 ml) was added water (150 ml) and triphenylphosphine (0.90 g, 3.3 mmol). The solution was stirred for 24 h and was then concentrated to 5 ml. The residue was diluted with methanol (5 ml) and water (1 ml). One half of this solution was used to prepare the corresponding oxamate (see 48.182). To the remaining half of the stirred solution (0.342 mmol) was then added trimethylamine sulfurtrioxide complex (99 mg, 0.719 mmol). The pH was adjusted to 8.5 by 1M aqueous NaOH. After a few minutes a precipitate was formed, which was dissolved by adding tetrahydrofuran (0.7 ml) and methanol (1 ml). The reaction mixture was stirred for 0.5 h, after which time additional trimethylamine sulfurtrioxide complex (45 mg) was added The stirring was continued for 15 min. During the course of the reaction pH was kept at 8–9 by adding 1M aqueous NaOH. The mixture was then diluted with water (2 ml) and the organic solvents were evaporated under reduced pressure. Additional water (5 ml) was added and the suspension was lyophilised and chromatographed (SiO$_2$, chloroform-methanol-water 100:15:1→80:20:1) to give the sulfamino compound, presumably in the sodium salt form, (161 mg, 80%) after lyophilisation from water.

$^1$H NMR data (dmso-D$_6$) δ: 7.24 and 6.87 (AB pattern, further coupled, 4H, J=8.8 Hz), 4.69 and 4.24 (AB pattern, 2H, J=10.8 Hz, ArCH$_2$), 4.58 (s, 1H, H-1), 4.29 (dd, 1H, J=11.4 and 1.7 Hz, H-6$_a$), 4.05–3.96 (2H, H-6$_b$ and NH), 3.83–3.76 (m, 2H, H-2 and H-3), 3.76–3.73 (4H, s and m, H-5 and MeOAr), 3.54–3.40 (3H, C$\underline{H}_2$CH$_3$ and H-4), 3.27 (s, 3H, 1-OMe) and 1.12–1.02 (s and t, 12H, J=7.0 Hz, C(CH$_3$)$_3$ and CH$_2$C$\underline{H}_3$) ppm.

Methyl 6-O-pivaloyl-3-deoxy-2-O-ethyl-3-sulfamino-α-D-altro-pyranoside ammonium salt (bpy__37)

Methyl 6-O-pivaloyl-3-deoxy-2-O-ethyl-4-O-p-methoxybenzyl-3-sulfamino-α-D-altro-pyranoside sodium salt (153 mg, 0.259 mmol) was hydrogenolysed for 6 h in glacial acetic acid (8 ml) at 0.23 MPa and room temperature, using 5% palladium on charcoal as a catalyst. Filtering and lyophilisation gave a residue which was chromatographed (SiO$_2$, chloroform-methanol-water 80:20:1 with 0.1% NH$_3$) to give the title compound (77.2 mg, 74%).

$^1$H NMR data (D$_2$O, ref. acetone at 2.35 ppm) δ:4.83 (HDO), 4.78 (s 1H, H-1), 4.43 (dd, virtually coupled, 1H, J=11.5 and 1.1 Hz, H-6$_a$), 4.30 (dd, virtually coupled, 1H, J=11.5 and 5.1 Hz, H-6$_b$), 3.95–3.91 (2H, H-4 and H-5), 3.89 (dd, 1H, J=3.3 and 1.3 Hz, H-2), 3.80–3.62 (m. 3H, H-3 and C$\underline{H}_2$CH$_3$), 3.42 (s, 3H, CH$_3$O) and 1.24–1.21 (s znd t, 12H, J=7 Hz, $^t$Bu and CH$_2$C$\underline{H}_3$) ppm (the assignments of the $^1$H NMR spectrum signals were made on the basis of a COSY experiment).

$^{13}$C NMR data (D$_2$O, ref.: acetone at 33.19 ppm) δ188.3, 106.2, 82.2, 73.8, 72.8, 70.6, 69.3, 61.9, 59.8,45.6, 37.1 and 21.3 ppm.

Methyl 6-O-pivaloyl-3-deoxy-2-O-ethyl-4-O-p-methoxybenzyl-3-$^t$butyloxamido-α-D-altropyranoside Oxalyl chloride (120 μl, 1.37 mmol) dissolved in tetrahydrofurane (1 ml) was cooled to −26° C. A solution of t-butanol (131 mg, 1.77 mmol) and pyridine (154 μl, 1.91 mmcl) in tetrahydrofurane (2 ml) was added dropwise and the mixture was stirred at −26° C. for 15 min, while the initially formed yellowish precipitate turned white.

The solvents were removed under reduced pressure from the tetrahydrofurane solution from the reduction of 3-azido-6-O-pivaloyl-3-deoxy-2-O-ethyl-4-O-p-methoxybenzyl-α-D-altropyranoside (150 mg, 0.342 mmol). The residue was redissolved in tetrahydrofurane (2.5 ml) and pyridine (154 μl) and added dropwise to the cooled solution above and stirred at −26° C. for 1h. Water (2 ml) was added and the mixture diluted with t-butyl methyl ether (15 ml) and washed with water, saturated sodium hydrogen carbonate and brine. The organic solution was dried over sodium sulfate and the solvents were removed under reduced pressure. The residue was chromatographed (SiO$_2$, t-butyl methyl ether—toluene 1:8) to yield 187 mg, 100% of the title compound.

$^1$H NMR data (CDCl$_3$) δ: 8.25 (d, 1H, 10.1 Hz, 3-NH), 7.26 and 6.85 (AB pattern, further coupled, 4H, J=8.6 Hz), 4.82–4.71 (m and d, 2H, 10.5 Hz, H-3 and ArC$\underline{H}_2$), 4.69 (s, 1H, H-1), 4.42 (dd, 1H, 1.7 and 11.7 Hz, H-6$_a$) 4.31 (d, 1H, 10.5 Hz, ArC$\underline{H}_2$), 4.16 (dd, 1H, 6.2 and 11.7 Hz, H-6$_b$), 3.88 (ddd, 1H, 1.8, 5.9 and 10.3 Hz, H-5), 3.81–3.75 (dd and s, 4H, H-4 and ArOMe), 3.64–3.49 (m, 2H, C$\underline{H}_2$CH$_3$), 3.47–3.43 (dd and s, 4H, 1.3 and 3.1 Hz, H-2 and 1-OMe), 1.55 (s, 9H, oxamate C(CH$_3$)$_3$), 1.19 and 1.18 (s and t, 12H, 7 Hz, 6-O pivaloate $^t$Bu and CH$_2$CH$_3$) ppm.

$^{13}$C NMR data (CDCl$_3$) δ: 178.1, 159.4, 159.1, 157.4, 130.3, 129.4, 113.8, 98.9, 84.2, 77.2, 75.9, 70.8, 69.5, 65.8, 65.7, 63.4, 55.2, 55.1, 45.7, 38.8, 27.7, 27.1, 15.3 ppm.

Methyl 6-O-pivaloyl-3-deoxy-2-O-ethyl-3-oxamiido-α-D-altropyranoside ammonium salt (bpy_54)

Methyl 6-O-pivaloyl-3-deoxy-2-O-ethyl-4-O-p-methoxybenzyl-3-$^t$butyloxamido-α-D-altropyranoside (180 mg, 332 µmol) was dissolved in acetic acid-ethanol mixture (1:1, 6 ml), palladium on carbon (5%, 250 mg) was added and subjected for hydrogenolysis at 39 psi overnight. The catalyst was filtered of on a celite pad, washed with ethanol. The filtrate was concentrated under reduced pressure, redissolved in dichloromethane (2.4 ml). Trifruoroacetic acid (960 µl) was added and the mixture stirred for 4.5 h at room temperature. Water (3 ml) and ammonia (3M, 300 µl) was added and reaction mixture was concentrated under reduced pressure and lyophilized. The residue was chromatographed (SiO$_2$, chloroform-methanol-water 80:20:1 with 0.1w NH$_3$) to give the title compound, 117.1 mg, 89%.

$^1$H NMR data (D$_2$O, ref. acetone at 2.35 ppm) δ: 4.80 (HDO), 4.78 (s 1H, H-1), 4.45–4.35 (m, 2H, H-3 and H-6$_a$), 4.26 (dd, 1H, 4.4 and 12.1 Hz, H-6$_b$), 4.07–3.96 (m, 2H, H-4 and H-5), 3.77–3.58 (m, 3H, CH$_2$CH$_3$ and H-2), 3.45 (s, 3H, 1-OMe), 1.20–1.13 (s and t, 12H, 6-O-pivaloate $^t$Bu and CH$_2$CH$_3$) ppm.

$^{13}$C NMR data (D$_2$O, ref.: acetone at 33.19 ppm) δ: 188.1, 171.9, 171.4, 105.7, 82.4, 73.7, 72.9, 70.3, 69.7, 62.0, 56.1, 45.9, 37.0, 21.2 ppm.

Methyl 3-azido-6-O-pyrrol-3'-ylcarboxyl-3-deoxy-2-O-ethyl-4-O-p-methoxybenzyl-α-D-altropyranoside A solution of methyl 3-azido-3-deoxy-2-O-ethyl-4-O-p-methoxy-benzyl-α-D-altro-pyranoside (476 mg, 1.3 mmol) in pyridine (496 µl) and dichloromethane (2 ml) was stirred at 0° C. Methanesulfonyl chloride (380 µl, 4.90 mmol) was added and the temperature was raised to room temperature. The stirring was continued for 5 h and the mixture was then cooled to 0° C. Water (1 ml) was added and the mixture was stirred for additional 20 min. at room temperature, evaporated and partitioned between ethyl acetate and water. The organic phase was washed subsequently with water, saturated aqueous NaHCO$_3$, water, saturated aqueous NaCl, dried (Na$_2$SO$_4$), filtered and evaporated. Chromatography (SiO$_2$, methyl tert-butyl ethertoluene 1:9) yielded 216 mg (79%) of the mesylate as a yellowish oil.

N-Triisopropylsilyl pyrrole-3-carboxylic acid (484 mg, 1.81 mmol) and 1,8-diazacicyclo[5.4.0]undec-7-ene (255 µl) were dissolved in dimethylformamide (1 ml) and added to a solution of the mesylate above in dimethylformamide (1 ml). The mixture was heated at 90° C. overnight and the subjected to chromatography (210 g C-8 Lobar, Merck, acetonitrile-water 3:2) to yield 30 mg, 16% of the pyrroloyl ester.

$^1$H NMR data (CDCl$_3$) δ: 8.73 (br.s., 1H, pyrrole NH), 7.39 (symm. m., 1H, pyrrole H-4), 7.27 and 6.85 (AB pattern, further coupled, 4H, J=8.8 Hz), 3.74 (symm. m, 1H, pyrrole H-2), 3.64 (symm. m, 1H, pyrrole H-5), 4.63–4.49 (s and 2 d, 3H, H-1 and ArCH$_2$), 4.48–4.36 (m, 2H, 2H-6), 4.22 (symm. m, 1H, H-5), 3.94–3.84 (m, 2H, H-3 and H-4), 3.78 (s, 3H, ArOMe), 3.68–3.55 (m, 3H,CH$_2$CH$_3$ and H-2), 3.40 (s, 3H, 1-OMe), 1.20 (t, 3H, 6.8 Hz, CH$_2$CH$_3$) ppm.

$^{13}$C NMR data (CDCl$_3$) δ: 164.6, 159.5, 129.9, 129.4, 123.6, 11.7, 116.1, 113.9, 109.9, 99.9, 76.9, 72.5, 72.0, 66.8, 66.3, 63.0, 58.9, 55.3, 55.2, 15.4 ppm.

Methyl 6-O-pyrrol-3'-ylcarboxyl-3-deoxy-2-O-ethyl-3-sulfamino-α-D-altropyranoside ammonium salt (bpy_40)

To a stirred solution of methyl 3-azido-6-O-pivaloyl-3-deoxy-2-O-ethyl-4-O-p-methoxybenzyl-α-D-altropyranoside (30 mg, 61 µmol) in tetrahydrofuran (1 ml) was added water (11 µl) and triphenylphosphine (83 mg, 305 µmol). The solution was stirred for 24 h, diluted with and water (1 ml). Trimethylamine sulfurtrioxide complex (9 mg, 0.72 µmol) was then added. The pH was adjusted to 8.5 by 1 M aqueous NaOH. After a few minutes a precipitate was formed, which was dissolved by adding tetrahydrofuran (0.7 ml) and methanol (1 ml). The reaction mixture was stirred for 0.5 h, after which time additional trimethylamine sulfurtrioxide complex (9 mg) was added. The stirring was continued for 15 min. During the course of the reaction pH was kept at 8–9 by adding 1M aqueous NaOH. The mixture was then diluted with water (2 ml), washed with t-butyl methyl ether, lyophilised and chromatographed (SiO$_2$, chloroform-methanol-water 80:20:1) to give the sulfamino compound, presumably in the sodium salt form, (30.6 mg, 93%) after lyophilisation from water.

$^1$H NMR data (CD$_3$OD) δ: 7.35 (unresol. dd, x part of a ABX-pattern, 1H, J$_{AX}$+J$_{BX}$=3.5 Hz, pyrrole H-2), 7.29 and 6.79 (AB pattern, further coupled, 4H, J=8.6 Hz), 6.75 (dd, 1H, 2.0 and 2.9 Hz, pyrrole H-4), 6.51 (dd, 1H, 1.3 and 2.9 Hz, pyrrole H-5), 4.71 and 4.46 (AB pattern, 2H, J=11.4 Hz, ArCH$_2$), 4.66 (bs, 1H, H-1), 4.39 and 4.33 (2 dd, 2H, 2.6, 5.1 and 11.7 Hz, 2H-6), 4.04 (m, 1H, H-3), 3.97–3.87 (m and dd, 2H, 1.1 and 3.1 Hz, H-5 and H-2), 3.80 (dd, 1H, 4.4 and 10.1 Hz, H-4) 3.73 (S, 3H, ArOMe), 3.68–3.52 (m, 2H, CH$_2$CH$_3$), 3.39 (S, 3H, 1-OMe), 1.15 (t, 3H, 7.0 Hz, CH$_2$CH$_3$) ppm.

$^{13}$C NMR data (CD$_3$OD) δ: 167.32, 160.9, 131.3, 131.0 125.3, 120.1, 116.3, 114.7, 110.2, 101.7, 77.2, 10.4, 69.9, 67.2, 66.4, 55.6, 55.5, 50.9 and 15.8 ppm.

The residue was dissolved in methanol (15 ml), palladium on carbon (5%, 50 mg) was added and the mixture hydrogenolyzed at 30 psi for 3 h. The catalyst was filtered off, the filtrate concentrated under reduced pressure, redissolved in ammonia (2%) in methanol-water (1:1, 0.6 ml) and chromatographed (3 ml C-18 Supelco, methanol-water 2:3). Methanol was removed under reduced pressure from the pooled product-containing fractions and the residue lyophilized to give 6.2 mg of the title compound as the ammonium salt.

$^1$H NMR data (CD$_3$OD) δ: 7.35 (m, 1H, pyrrole H-2), 6.75 (dd, 1H, 2.0 and 2.9 Hz, pyrrole H-4), 6.55 (dd, 1H, 1.3 and 2.9 Hz, pyrrole H-5), 4.67 (br.s, 1H, H1), 4.55 (dd, 1H, 1.3 and 11.4 Hz, H-6$_a$), 4.31 (dd, 1H, 5.9 and 11.6 Hz, H-6$_b$), 3.86–3.76 (m, 4H, H-2, H-3, H-4, H-5), 3.75–3.56 (m, 2H, CH$_2$CH$_3$), 3.40 (s, 3H, 1-OMe), 1.21 (t, 3H, Hz, CH$_2$CH$_3$) ppm.

Example 6

Chaperone Assays and the Use Thereof in Testing Compounds for Inhibition of Chaperone Binding In order to conclusively identify peptides or peptide mimetics that bind strongly to PapD, a good assay is required. The maltose binding protein (MBP) has been engineered by the inventors so that it is recognized by PapD. The commercially available plasmid pMAL-P2 encoding MBP with a linker arm encoding sequence fused to the 3' end of the gene was used. MBP is secreted into the periplasmic space and is easily purified by affinity chromatography using amylose resin. MBP is eluted from the column with 20 mM maltose. PapD is not co-eluted with MBP when co-expressed with MBP whereas fusing the PapG COOH-terminus to MBP results in PapD binding to MBP to form a complex that is co-eluted from the affinity column. Using this strategy, it has been found that fusing the carboxy terminal 140 (MBP-G1'-140') and 134 (MBP-G134') amino acids of PapG to MBP results in the formation of a strong PapD-MBP complex which is purified by maltose affinity chromatography. The complex between the MBP fusion and PapD has been shown to be stable in up to 3 M urea similar to the stability of a PapD-PapG complex arguing that the COOH-terminal 134 amino acids of PapG probably contains most of the chaperone recognition motif. In addition, binding to the MBP fusion protein has proven dependent on the universal chaperone anchoring residues, Arg-8 and Lys-112, as described herein since mutations in these two residues abolished PapD binding to the MBP fusion protein.

It is also interesting to test the ability of MBP-G fusions to inhibit pilus assembly and thus bacterial attachment by co-expressing the fusion proteins in cells producing P pili. If PapD binds to the MBP-G fusion, it will be titrated away from pilus subunits and thus decrease or abolish pilus formation. This technique will be one mechanism to validate the concept that chaperone binding peptides can abolish the virulence of a pathogen by preventing the assembly of surface-localized adhesins. Using this analysis it has been found that in strains producing P pili, co-expression of the MBP-G1'-140' and MBP-G134' fusion completely abolishes the ability of the bacteria to bind red blood cells and cause hemagglutionation. Further, it has recently been shown by the inventors that after coexpression of the MBP-G1'-140' fusion in HB101/pPAP5-bacteria, it was not possible to detect any visual signs of pili on the surface of the bacteria by electron microscopy. This is evidence for the theory expressed in this invention, that the prevention/inhibition of binding between pilus subunits and molecular chaperones also prevents the assembly of intact pili.

These results support the biological relevance of the crystal structure described in FIG. 3, showing that other proteins can be engineered to be recognized by PapD by fusing the carboxy terminal recognition site onto that protein. The MBP-G134' and MBP-G1'-140[1] fusions have been purified to establish in vitro assays to measure interactions with PapD. The purified fusion proteins are coated on wells of microtiter plates and the ability of PapD to bind to the fusion proteins is tested in an ELISA procedure. This assay is critical since it allows testing the ability of compounds to inhibit binding of PapD to the domain on PapG recognized by the chaperone. Furthermore, the purified fusion proteins can be used in the Pharmacia BiaCore® assay to quantitate binding to PapD and establish inhibition assays for compounds of the invention. Carboxyl-terminal peptides have already been suggested to correspond to part of the chaperone recognition motif. One can thus investigate whether the carboxyl terminal peptides are able to inhibit binding of PapD to the MBP-G1'-140' fusion in the ELISA assay. The development of this high through-put assay makes it possible to screen peptide libraries, chemical libraries, natural compounds, and peptide mimetics for their ability to inhibit chaperone binding. In addition, this assay can be used to test whether the known periplasmic chaperones utilize common recognition paradigms.

In addition to testing compounds for their ability to inhibit binding to the MBP-G fusion, other assays have been established which measure PapD-peptide interactions. For example, an ELISA has been developed to measure the binding of PapD to peptides coated on wells of microtiter plates. In this assay the octameric peptide G1'-8'WT was an equally efficient inhibitor as the 19-mer G1'-19'WT, revealing the octamer to be the optimal starting point for designing of modified compounds with increased affinity for the binding site of PapD (cf. Example 7).

Also, as previously described, native PapD is able to bind to reduced, denatured PapG and restore the PapD-PapG complex in vitro in a reconstitution assay (Kuehn et al., 1991). This assay has been proposed to reflect the recognition function of PapD in vivo and will be used to determine the ability of the compounds to inhibit PapD binding to PapG in vitro. For example, the carboxyl terminal PapG peptide has been shown to inhibit the binding of PapD to PapG in this assay, establishing that it occupies the pilus subunit binding site of PapD. Another way to map PapD-peptide interactions is to test the ability of compounds to reduce the rate of well defined proteolytic cleavage events. For example, partial digestion with trypsin cleaves PapD in the P1-G1 loop at residue Lys-99 (See "T" site denoted in FIG. 3). The rate of tryptic cleavage of PapD was reduced by preincubation of PapD with PapG and PapK peptides (cf. Example 2). The observed protection of PapD by bound peptides may be due to a change of the local conformation of the F1-G1 loop, or due to physical contact of the loop by the peptide. These assays may thus be used as an initial screening for the ability of new compounds to bind to PapD and interfere with its recognition function. Strong binding compounds that inhibit PapD binding to the MBP-G1'-140' fusion will be co-crystallized with PapD to provide the structural basis of the recognition surface used by PapD. As new crystallographic data becomes available, the relevance of critical PapD-inhibitor or PapD-enhancer interactions will be tested by determining the effect of site-directed mutations on the ability of the chaperone to bind pilus subunits and mediate pilus assembly. This important information will lead to defining how chaperones recognize subunits and the function of chaperone-subunit interactions.

A quantitative chaperone binding assay has also been developed: A modified PapG peptide has been synthesized, wherein Ser-9' is substituted by a Cys. From the crystal structure of PapD bound to the peptide, the side chain of Ser-9' was not predicted to interact with PapD. Instead, this side chain was oriented towards the solvent, but Ser-9' was adjacent to the last amino acid of the interactive zipper between PapD and the peptide. The environmentally sensitive fluorescent probe 5-IAF (5-iodoacetamidfluorescein) was then covalently coupled to the peptide via the sulfhydryl group on the Cys residue and the labelled peptide was purified; of course any other suitable envirorenmentally sensitive fluorescent probe may be employed. It was found that the addition of PapD to the peptide causes a marked decrease in the fluorescent intensity and a shift in the emission maxima. This information was used to calculate a binding constant for the PapD-peptide interaction. The change in the fluorescence intensity at 514 nm after the addition of increasing concentrations of PapD was determined. By plotting the fluorescent intensities versus PapD concentrations, a binding constant of $2.5 \times 10^{-6}$ M was calculated (The calculations were performed on the commercially available computer program "Kaleidagraph").

It is thus possible to evaluate the binding constants of other substances binding to PapD in a quantitative manner, as the addition of a substance which binds competitively to PapD will result in an increased fluorescence compared to a situation where less or no competitive substance is present in the system.

A similar assay system will be developed using MBP-G1'-140' instead of the PapG peptide as described herein. As this fusion protein has been found to interact with two binding sites in PapD, it will be possible to 1) quantitate the binding affinity to the second binding site (on domain 2) and 2) screen for compounds which interact with either of the two binding sites and quantitate the interaction. Of course, labelling the site 2 peptide with a suitable environmentally sensitive probe should allow a determination of the binding constant using the same methodology as describe above.

The discovery that the DegP protease is greatly responsible for the degradation of pilin subunits in the absence of a chaperone renders the degP41 strain an interesting candidate for an in vivo test system of the effects exerted on PapD by compounds of the invention.

When administering a substance which prevents, inhibits or enhances the binding between the chaperone and the pilus subunits to a system containing the degP41 strain, the substance should, even in small amounts, be toxic to the bacteria, as the DegP⁻ bacteria will be incapable of degrading the accumulating pilus subunits. Note that a degP41 strain was used to identify a hitherto unknown binding site on domain 2 of PapD, cf. example 10.

However, such an assay requires that the tested substance is able to enter the periplasmic space before it can exert its effect; this fact renders this type of assay less suitable as a screening assay for lead compounds, as it will "ignore" substances which have the desired effects on chaperone-subunit interaction, but which are e.g. too hydrophillic to enter the periplasmic space. On the other hand, the system will be well-suited for assessing the clinical potential of substances which have already proven successful in the in vitro assays described herein.

Once the model PapD system is in place, the experiments described above can of course be expanded to include the other members of the PapD-like family of chaperones. In this way it will be possible to establish the general requirements for chaperone recognition and the molecular basis of the chaperone recognition paradigm in gram negative bacteria.

Some specific assays for determination of interactions with molecular chaperones are described in detail in Example 10.

Example 7

Design of Peptides and Peptide Mimetics Capable of Binding to the Binding Site of PapD and Other Pilus Assembling Chaperones To provide further information on chaperone-subunit interactions, it is contemplated to synthesize peptides overlapping the entire PapG protein and other pilus subunits. In addition, probing peptide binding to available chaperones using both a chemical peptide library and a phage display library should be performed. The two libraries are complementary since the peptides are presented in different environments which could importantly influence binding to the chaperones. In practice the chemical library is limited to all possible hexapeptides and to hepta- and octapeptides if some of the natural amino acids are excluded or if one or two residues are kept invariant. This library can be evaluated by direct binding of the chaperone to the resin beads and sequencing of interesting peptides. The phage display library contains approximately $10^{10}$ peptides in the PIII protein of the so-called "fusion phage" that retains phage function and displays the foreign peptides on the surface. The ability of peptide-containing phages to bind PapD coated in wells of microtiter plates can be detected in an ELISA using the techniques described in Example 6. Positive binding phages will be amplified, purified and retested for their ability to bind PapD. The sequence of the peptide insert of positively binding phages will be determined and the corresponding peptides will be synthesized and tested for their ability to inhibit biding of PapD to the MBP-G fusion as described in Example 6.

The results from the studies outlined above will be of the utmost importance for design and evaluation of ligands acting as "chaperone inhibitors". In spite of this, the crystal structure of the PapD-PapG 19-mer peptide complex provides sufficient insight into chaperone-ligand interactions to initiate systematic studies of small peptides and peptide mimetics as chaperone inhibitors already at the present stage. The high inhibitory power of the PapG 8-mer peptide to PapD (equal to the PapG 19-mer peptide, cf. Example 6) reveals the feasibility of such studies and the conserved features of the proposed binding site on the chaperones indicate that such inhibitors could well have broad specificity.

The specificity in recognition of the PapG 19-mer by PapD has been suggested to be provided by anchoring of the peptide's carboxyl terminus to the PapD cleft residues Arg-8 and Lys-112 and subsequent "zippering" interactions between alternating hydrophobic residues in the peptide and complementary hydrophobic residues in PapD. The following experiments support this hypothesis. Firstly, mutations in the anchor residues Arg-8 and Lys-112 have abolished subunit binding in vivo. Secondly, deletion of the C-terminal residue in the PapG 19-mer leads to a substantially decreased binding to PapD as the hydrophobic "zippering" interactions between peptide and PapD were then placed off register when the C-terminus of the deletion peptide was anchored to Arg-8 and Lys-112. The "zippering" hypothesis for specificity in binding between PapD and peptides (or pilus subunits) has been preliminary investigated by performing the following experiments:

A length series of peptides form the C-terminus of PapG consisting of G1'-5', G1'-6', G1'-7', G1'-8', G1'-11', G1'-16' and G1'-19' was prepared. A replacement series and a deletion series of G1'-8' was also synthesized. In the replacement series Pro-1', Phe-2', Leu-4', Val-5', Met-6' and Met-8' was replaced by Ser, whereas Ser-3' and Thr-7' was replaced by Ala (i.e. hydrophobic amino acids was replaced by the polar Ser and hydrophillic amino acids was replaced by Ala). In the deletion series one residue at a time in G1'-8' was deleted with simultaneous addition of a serine (which is found in position 9' in native PapG) to maintain the peptide length at 8 amino acids. The peptides were all synthesized by the Fmoc solid phase strategy and were purified by reversed phase HPLC.

The ability of the peptides to inhibit the binding of PapD to the MBP-G1'-140' fusion protein was then investigated using the following ELISA test:

Stock solutions of MBP-G1'-140' proteins in PBS were diluted to 0.1 $\mu$M with PBS. The wells of microtiter plates were coated with 50 $\mu$l of the protein solutions overnight at 4° C. The wells were washed with PBS, and blocked with 200 $\mu$l of 3% bovine serum albumin (BSA) in PBS for 2 hours at 25° C. The plates were washed vigorously three times with PBS and incubated with 50 $\mu$l of 1–5 pM PapD proteins in 3% BSA-PBS for 45 minutes at 25° C. The PapD was preincubated with each of the peptides at a 1:25 ratio for 30 min before being added to the wells. After three washings with PBS, the wells were incubated with a 1:500 dilution of rabbit anti-PapD antiserum in 3% BSA-PBS for 45 minutes at 25° C. After three washings with PBS, the wells were incubated with a 1:1000 dilution of goat antiserum to rabbit IgG coupled to alkaline phosphatase in 3% BSA-PBS for 45 minutes at 25° C. After three washings with PBS and three washings with developing buffer (10 mM diethanolamine, 0.5 MM $MgCl_2$), 50 µl filtered 1 mg/ml p-nitrophenyl phosphate in developing buffer was added, the reaction was incubated for 1 hour or longer if necessary in the dark at 25° C., and the absorbance at 405 nm was read.

The inhibitory powers of the peptides in the three series are presented in FIGS. 17–19 and the number of experiments performed with each series is given in the FIGS. Vertical lines for each peptide in the figures are 95% confidence intervals obtained after a statistical analysis of the experimental data. As revealed by the evaluation of the length series, the peptides G1'-8', G1'-11' and G1'-16' are significantly more potent than the shorter G1'-6' and G1'-7' (FIG. 17). This observation fits very well with the crystal structure of PapD complexed with G1'-19' which shows that the C-terminal 8 residues in G1'-19' are hydrogen bonded to PapD. The shorter peptides G1'-6' and G1'-7' are unable to fulfil this hydrogen bonding pattern and are therefore less active inhibitory peptides (FIG. 18). The replacement series reveals that residues 4', 5' and 6' in G1'-8' form important contacts with PapD; since their replacement results in less active inhibitory peptides (FIG. 18). The deletion series again indicated an important role for residues 4', 5' and 6' in G1'-8' for the complex formation with PapD (FIG. 19). However, the results obtained with the deletion series did not support the "zippering" hypothesis according to which the members of the deletion series would show an increasing inhibitory potency as the deletion is moved form the C-terminus towards the N-terminus of G1'-8'.

As appears from these preliminary results, the results obtained in the assay exhibit large deviations from the mean in each experiment. As discussed herein, one reason for this might be the slow kinetics of binding between PapD and correctly folded pilus subunit proteins and analogues of such correctly folded subunit proteins. It is therefore contemplated to modify the assay by introducing denaturing influences powerful enough to at least partially unfold the pilus subunit (analogues). It is expected that this will reduce the deviations in the assay results. Another reason for the large deviations might be binding of the peptides to BSA used in the ELISA. Therefore, the replacement of BSA with other macromolecules will be investigated.

In case the "zipper mechanism" for peptide binding to PapD can be confirmed, peptide chaperone binding can be optimized using a limited synthetic peptide library in which Pro-1', Phe-2', Leu-4', Met-6' and Met-8' of the Papg 8-mer are replaced by the hydrophobic amino acids Val, Leu, Ile, Met, Phe, Trp, Tyr and His. Non-natural amino acids such as D-amino acids and N-methylated amino acids, as well as amino acids containing aliphatic and various aromatic side chains, will also be incorporated in the chemical library. Optimal amino acid combinations for these five positions will be used in the synthesis of the chaperone inhibitors described below in this Example. If the "zipper mechanism" is not confirmed, the outlined approaches will be applied to residues shown to be important for binding to PapD.

Chaperone inhibitors that form covalent bonds to the chaperone after docking into its active site will be developed. The crystal structure of the PapD-peptide complex shows that the C-terminal carboxyl group of the peptide is hydrogen bonded to Lys-112 and Arg-8 in the chaperone and that the side chain of Val-5' in the peptide is close to the side chain amino group of another Lys in PapD. Introduction of reactive groups such as alkyl halides, aldehydes, acid halides and active esters in these positions of the optimized 8-mer peptide will lead to the formation of covalent bonds to the lysines in PapD, and the peptide derivatives thus constitute high affinity inhibitors. The inhibitors are based on nonamer or shorter peptides in which residue 5 (from the C-terminus) and/or the C-terminal carboxyl group have been modified as indicated:

Replacements for residue 5 from the C-terminus:

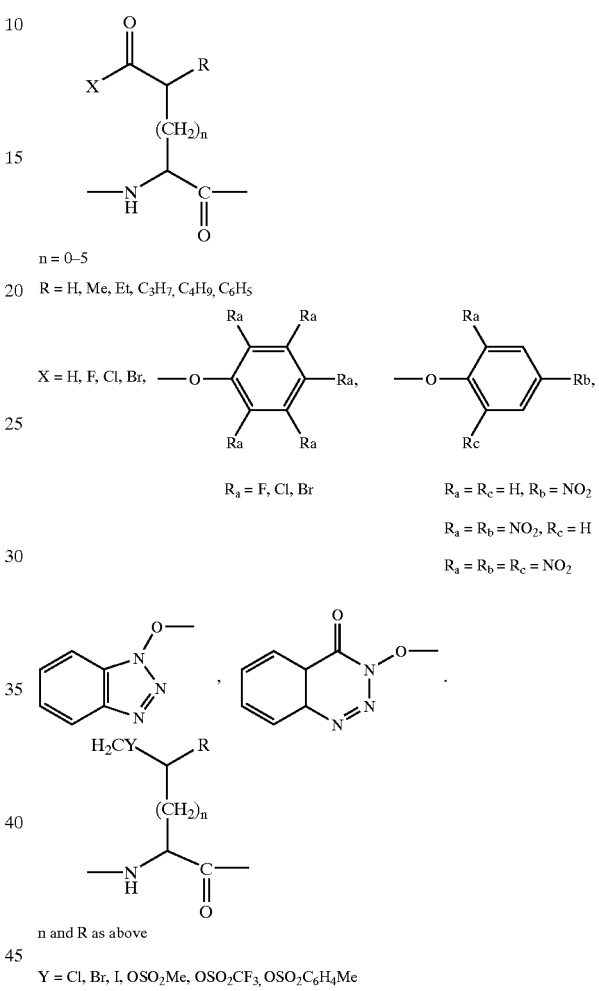

n = 0–5

R = H, Me, Et, $C_3H_7$, $C_4H_9$, $C_6H_5$

X = H, F, Cl, Br, $R_a$ = F, Cl, Br $R_a = R_c$ = H, $R_b$ = $NO_2$ $R_a = R_b$ = $NO_2$, $R_c$ = H $R_a = R_b = R_c$ = $NO_2$ n and R as above Y = Cl, Br, I, $OSO_2Me$, $OSO_2CF_3$, $OSO_2C_6H_4Me$ Replacement for the C-terminal COOH-group:

—COX, X as above

—$CH_2Y$, Y as above

Such interactions between aldehydes and lysine side chains have given potent drug candidates for sickle-cell anaemia.

In the PapD-peptide crystal, the peptide forms an extension of a β-sheet in the chaperone. Restrictions that give the peptide a β-sheet like conformation will therefore result in a favourable change in the entropy of binding. Conformationally restricted peptides constituting miniature cyclic β-sheets or peptides having the side chains of amino acids separated by one amino acid covalently linked to each other will be prepared based on the optimized 8-mer peptide. Peptides with covalently linked side chains will have the three consecutive amino acids replaced by the fragments shown below:

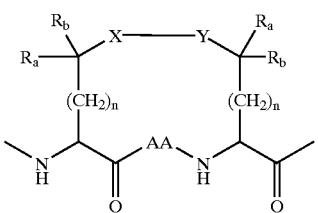

X,Y = S, S; S, CH₂; CH₂, S; O, CH₂;
CH₂, O; CH₂CH₂

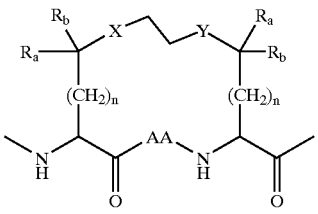

X,Y = S, S; S, CH₂; CH₂, S; O, O;
O, CH₂; CH₂, O; CH₂, CH₂

AA=any natural or nonnatural amino acid $R_a, R_b$=all possible combinations of H, Me, Et, $C_3H_7$, $C_4H_9$, $C_6H_5$

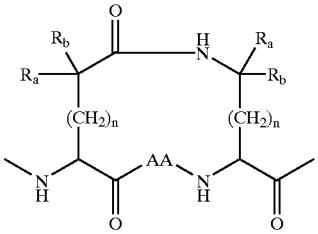

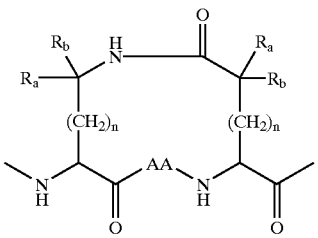

AA=any natural or nonnatural amino acid $R_a, R_b$=all possible combinations of H, Me, Et, $C_3H_7$, $C_4H_9$, $C_6H_5$ Interesting inhibitors will be co-crystallized with chaperones, and the complexes will also be investigated by NMR spectroscopy.

Peptides and peptide mimetics used as drugs can be rapidly metabolized by proteolytic enzymes that cleave the peptide bonds. Chymotrypsin selectively cleaves the peptide bond on the carboxyl side of amino acids with aromatic and large hydrophobic side chains. In the PapG 8-mer, the Met-8'-Thr-7', Met-6'-Val-5' and Phe-2'-Pro-1' amide bonds are therefore especially sensitive to proteolysis and should be replaced by metabolically stable peptide isosters. Examples of such peptide isosters are given below:

Replacement for the

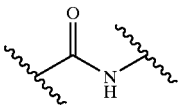

fragment:

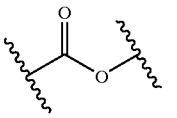

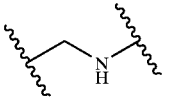

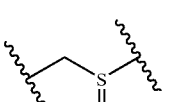

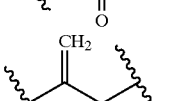

—CH₂CH₂—

Example 8

The Role of Periplasmic Chaperones in the Infectivity of Bacteria Which Adhere by the Means of Pili The specific role of chaperone assisted pilus assembly in virulence can be determined by comparing the adherence and pathogenicity of piliated wild type and isogenic mutants that are non-piliated due to site-directed mutations in the active site of the chaperone. Mutations in residues such as Arg-8 and Lys-112 that constitute the subunit binding site of PapD can be recombined into the bacterial chromosome of the clinical isolate strain DS17 using the same method that has been successful to introduce point mutations into the papG gene in the chromosome of the same strain. *E. coli* strain DS17 spread epidemically within a neonatal ward, causing several cases of pyelonephritis. In addition, the strain has been found to cause acute kidney infections in a cynomolgus monkey pyelonephritis model. DS17 contains one pap gene cluster with a papG gene expressing a typical papG adhesin. It also expresses typical type 1 pili containing the mannose-binding adhesin, FimH. Type 1 pili have been suggested to be important virulence determinants in cystitis. Therefore, site-directed mutants in the subunit binding site of the FimC chaperone should also be generated to test this concept.

It is contemplated that a compound that binds the chaperone active site would block pilus assembly and thus prevent attachment. If this concept is valid, then well-defined chaperone mutants such as in Arg-8 and Lys-112 should abolish receptor binding, too. The receptor binding activity of various chaperone mutants should be measured in the receptor binding ELISA assays described in examples 2 and 6. To measure type 1 pilus-mediated binding, mannose will be linked to the wells of the microtiter plates. Adherence of various FimC and PapD chaperone mutants to the immobilized receptors will be quantitated using antibodies to E. coli DS17 in an ELISA experiment. Furthermore, the ability of small PapD-binding peptides to block pilus assembly in DS17 and, thus, to abolish receptor binding will be tested. Strain DS17 will be grown in the presence of short PapD-binding or non-binding peptides and then tested for their ability to bind receptor in the ELISA experiment. These experiments will make important strides at validation the concept that anti-chaperone inhibitors would prevent bacterial attachment in vitro.

Then, the role of chaperone-assembled adhesins in causing diseases will be established. The causality between E. coli expressing P pili and pyelonephritis has until recently been based solely on epidemiological data. It has been shown that the P piliated strain DS17 causes pyelonephritis to occur in the normal urinary tract of cynomolgus monkeys. A mutation in the papG gene of strain DS17 was generated by allelic replacement to create the derivative strain DS17–8 to test the requirement of the PapG adhesin in causing the disease. DS17–8 contains one base pair deletion after codon 37 in papg resulting in the expression of P-pili lacking the PapG tip adhesin. This mutant was unable to bind the globoside receptor in vitro and was unable to bind to kidney tissue from humans or cynomolgus monkeys in our in situ attachment model. The virulence between DS17 and its papG mutant DS17–8 in the cynomolgus monkey was compared. To study the role of the PapG adhesin in pyelonephritis, five monkeys were infected with E. coli strain DS17 whereas six monkeys received mutant strain DS17–8 via a cytoscopically inserted ureteral catheter, and it was shown that there was a significant difference between the two groups. The monkeys receiving wild type strain DS17 has a mean bacteruria of 21 days compared to 6.8 days for those monkeys receiving the mutant strain DS17–8. Renal clearance was also significantly lower for the wild type strain and renal function was significantly reduced in the monkeys receiving the wild type strain but not in those monkeys receiving the isogenic papG mutant strain. Pathologic evaluation of the infected kidney confirmed the functional studies showing significantly less inflammation and pathologic changes in the mutant group as compared to those receiving the wild type.

Therefore, it is concluded that the Galα1–4Gal binding PapG adhesin at the tip of P pili is required for pyelonephritis to occur in the normal urinary tract of primates. Up to now, no such direct demonstration for the role of a pilus associated adhesin in a specific bacterial infection has been made.

Interestingly, in the experiments described above, no evidence was found that the PapG adhesin was required for colonization of the lower urinary tract or for the development of acute cystitis. Both strains colonized the vagina, persisted in the intestine and caused bladder infection. Thus, although PapG was a critical virulence determinant in causing pyelonephritis, it did not appear to be crucial in cystitis. However, this did not exclude the possibility that other components of the P pilus or that another type of pilus, such as type 1, was required for cystitis.

These hypotheses will be investigated by testing the virulence of isogenic DS17 mutant strains containing site directed mutations in Arg-8 of PapD or FimC. The mutants will presumably be defective in their ability to assemble P and type 1 pili. If the papD mutant is non-virulent in the monkey cystitis model, it may indicate that some component of the P-pilus other than PapG is essential for E. coli to generate bladder infection. For example, the major component of the tip fibrillum, PapE, has been shown to bind fibronectin and fibronectin could be an important factor in cystitis. Similarly, it the fimC mutant is non-virulent, it would confirm the role of the mannose-binding type 1 pili in causing cystitis. The ability of these point mutations to abolish the virulence of DS17 in causing either pyelonephritis or cystitis would validate the therapeutic potentials for a chaperone inhibitor.

Example 9

Identification of the Motif of Binding Between PapD and K1'-19'WT

In order to confirm the generality of the binding mode for C-terminal peptides of pilin subunits to PapD as observed in the PapD-G1'-19'WT crystal structure (see Example 1) a second PapD-peptide complex was investigated by X-ray crystallography. Since tight binding had been observed for the peptide derived from the wild-type C-terminal 19 amino-acids of PapK (K1'-19'WT, SEQ ID NO: 18, and numbered here from the C-terminal Arg-1' to the N-terminal Lys-19') it was decided to use this as the peptide for the second PapD complex.

Obtaining Material; Protein & Peptide.

PapD was prepared as previously described (Holmgren et al., 1988) and obtained from Dr. Scott Hultgren, Dept of Molecular Microbiology, Washington University School of Medicine, St. Louis USA. The peptide K1'-19'WT was prepared by Fmoc solid phase synthesis, purified by reversed phase HPLC and obtained from Dr. Jan Kihlberg, Dept. of Chemistry, University of Lund, Lund, Sweden.

Crystallisation of PapD-peptide Complex.

After a number of different experimental conditions had been explored around those previously used to obtain PapD-G1'-19'WT crystals the best crystals of the PapD-K1'-19'WT complex were grown by vapour diffusion against 20% PEG8000, 0.1 M MES pH 6.5. The crystallisation drop contained equal volumes of reservoir and protein solution. The protein solution (15 mg/ml) contained a 1:1 molar ratio of PapD to peptide in 20 mM MES pH 6.5 with 1.0% β-octyl glucoside (β-OG).

These crystals were mounted inside sealed quartz-glass capillary tubes and initially characterised by examining them on a X-ray precession camera. From standard analysis of such images it was determined that the above-mentioned crystals have a orthorhombic space group, C2221 (thus differing from the PapD-G1'-19'WT crystals which were C2), with cell dimensions a=57.1 Å, b=153.2 Å, c=135.4 Å and α=β=γ=90°, 2 molecules in the asymmetric unit and diffract to 2.7 Å resolution on a lab X-ray source with rotating anode and Cu $K_\alpha$ target.

Collection & Processing of Experimental Data.

The intensity data for the PapD-K-peptide crystals were collected on a R-AXIS II area-detector system (from R-AXIS) at Symbicom AB., Uppsala. All data were obtained from a single crystal and processed initially with the DENZO software package (Otwinsky, 1993). Merging and scaling of the data, however, was carried out using ROTAVATA and AGROVATA from the CCP4 package (CCP4, 1979). The final data set contained 15,989 independent reflections with an Rsym of 8.7% for data between 20.0 and 2.7 Å resolution.

Solution of Three Dimensional Structure.

The structure of the complex was solved by the standard method of molecular replacement using the program XPLOR (Brunger, 1992). The search model used was the refined 2.0 Å resolution structure of PapD (Holmgren and Branden, 1989. Using 8.0 to 4.0 Å resolution data the self-rotation function again gave a clear non-crystallographic two-fold axis. The top peaks in the translation functions also gave the correct solutions. After the translation functions the R-factor was 36.7% for 8.0 to 4.0 Å resolution data. Subsequent rigid body refinement in which all 4 domains of the 2 PapD molecules in the asymmetric unit were allowed to refine independently resulted in an R-factor of 33.6% for the same data.

Examination of an |FO|–|Fc| electron density map at this stage using the graphics program O (Jones and Kjeldgaard, 1994) showed clear density corresponding to the K-peptide in the PapD cleft and running along the surface of the protein in an analogous fashion to that found for the G-peptide. The orientation of the peptide was easily determined from the electron density, but initially only the final 12 C-terminal amino-acids of the peptide could be modelled into density. Refinement and Analysis of Structure.

Simulated annealing refinement with XPLOR (Brunger, 1992) was initiated at this stage. Several additional cycles of model building and refinement were carried out with a further 2 peptide amino-acids being added to the N terminal end of the peptide to yield an R-factor for the current model of 19.2% for 8.0 to 2.7 Å resolution data. The model at the present stage of refinement (which contains no water molecules and does not include the first 5 N-terminal amino-acids of the peptide) has root-mean square (rms) deviations from ideal geometry of 0.019 for bonds lengths and 3.80 ° for bond angles.

Despite the two PapD-peptide complexes being solved in different space groups, their overall structures are found to be highly similar with the peptide interacting with PapD in a manner essentially identical to that previously seen for the PapD-G1'-19'WT structure. Thus the K1'-19'WT peptide is again seen to bind in an extended conformation with the C-terminal Arg-1' anchored within the inter-domain cleft and subunit binding site. Hydrogen bonds are also formed between the peptide carboxy terminus and two invariant positively charged residues of PapD, Arg-8 and Lys-112. The K1'-19'WT peptide then run along the surface of the N-terminal domain, forming a parallel β-strand interaction with strand G1. In this way between 9 mainchain hydrogen bonds are formed between residues 10' to 2' of the peptide and Val-102 to Lys-110 of PapD and thus extending the β-sheet of PapD out into the peptide.

In addition, a dimer association is observed between the two PapD-peptide complexes within the unit cell similar to that seen in the PapD-G1'-19'WT crystal structure. Again the β-sheet is extended as a result of a non-crystallographic 2-fold symmetry which places a second PapD-peptide complex adjacent to the first such that the two bound peptide chains interact as anti-parallel β-strands with a mixed β-sheet again being created between the two complexes involving a total of 10 β-strands. The only major difference between the two PapD-peptide complexes is the fact that in the PapD-K1'-19'WT structure the peptides of the non-crystallographically related complexes are positioned two residues closer to the COOH-terminus of its partner. Thus while eight hydrogen bonds are formed between the peptides in the PapD-G1'-19'WT complex a total of 10 are observed in the PapD-K1'-19'WT.

Apart from the C-terminal residues Tyr-2' and Arg-1' there are again relatively few contacts between the sidechains of the peptide and PapD. The major interactions are provided by the mainchain hydrogen bonds to the Gi strand. There are, however, a number of hydrophobic interactions within the β-sheet, in particular between the peptide's Tyr-6' with Ile-105 and Leu-107 of strand G1.

Example 10

Identification of a Second Binding Site in PapD and Development of New Assays

Introduction

A chaperone binding assay was developed to delineate PapD-PapG interactions using MBP/G fusions, containing increasing lengths of the COOH-terminus of PapG. The ability of PapD to bind to PapG truncate proteins missing increasing lengths of the COOH terminus of PapG was also examined.

Experimental Procedures

Bacterial Strains

The *E. coli* strain HB101 (Maniatis et al., 1982) was used as a host strain in the studies involving the MBP/G fusion proteins. Strain DH5α was used as the host to construct MBP/G fusion proteins (Hanahan, 1983) and PapG truncates. KS474 (degP::kan) (Strauch et al., 1989) was kindly provided by J. Beckwith and used for expression of the PapG truncate proteins.

Plasmid Construction

The *E. coli* expression plasmid pMAL-p2 (new England Biolabs, Beverly, Mass., USA) was used for the construction of pMAL-p4, pMAL/G1'-19', pMAL/G1'-81' and pMAL/G1'-140' using procedures essentially from Maniatis (Maniatis et al. 1982). The malE gene encoded by pMAL-p2 has a lacZα sequence fused to the 3' end. Plasmid pMAL-p2 was digested with SalI and filled in with Klenow (Maniatis et al., 1982). The fragment was religated and the resulting plasmid called pMAL-p4 had a stop codon between the malE and lacZα sequences. Plasmid pMAL-p4 was digested with HindIII and filled in with Klenow and the resulting fragment was ligated with a ClaI linker, 5'CCATCGATGG3' (New England Biolabs, Beverly, Mass., USA) to produce plasmid pMAL-p5. Primer 23969
(5' CCCCCCTGCAGATCAGATTAAGCAGCTACCTGC3', SEQ ID NO: 23) and primer 23557 (5' CCCCTGCAGTAAAAATATCTCTGCTCAGAAATAC3', SEQ ID NO: 24) and primer 23559 (5' CCATCGATGAACAGCCAGTCAGATAATC3', SEQ ID NO: 25) were used for Polymerase Chain Reactions (PCR) utilizing pPAP5 (Hull et al., 1981; Lindberg et al., 1984) as the template. The DNA fragments encoding the region of amino acid residues 1'-81' and 1'-140' of the PapG were obtained from the PCR reactions using primers 23557 and 23559; and primers 23969 and 23559, respectively. The amplified DNA fragments were purified and restricted with PstI and ClaI and ligated into PstI and ClaI restricted pMAL-p5 fragment to construct pMAL/G1'-81' and pMAL/G1'-140', respectively. To create pMAL/G1'-19', two nucleotide oligomers (5'GGAAAGAGAAAACCCGGGGAGCTATCTGGTTC TATGACTATGGTTCTGAGTTTCCCCT GAT3', SEQ ID NO: 26 and 5' CGATCAGGGGAAACTCAGAACCAT-AGTCATAGAACCAGATAGCCCCGGGTTTTCTCTTT CCTGCA3', SEQ ID NO: 27) were chemically synthesized and annealed. The annealed DNA fragment containing the sequence of the carboxyl terminal 1'-19' amino acid residues of PapG was ligated to PstI-ClaI pMAL-p5 fragment to produce pMAL/G1'-19'. All the constructs used in this study were confirmed by DNA sequencing analysis using Sequenase Version 2.0 according to the manufacturer's directions (USB, Cleveland, Ohio, USA). pHJ14 (PapG3) was created by digestion of pHJ8 (wt PapG in $P_{tac}$ promoter plasmid, pMMB66) with BamHI and BglII, removing approximately 500 nucleotides, purification of the large fragment and religation. pHJ23 (PapG 2) was created by first cloning papG into pUC19 at EcoRI and BamHI, digesting with HincII to remove the last approximately 300 nucleotides and religating. The EcoRI-HincII fragment was then cloned into pMMB66 to create pHJ23.

Induction and Partial Purification of MBP/G Fusions

Strains carrying MBP or MBP/G fusion gene plasmids were induced in LB broth culture with 1 mM isopropylthiogalactoside (IPTG). Periplasmic extracts were prepared as described (Slonim et al., 1992). One tenth volume of 10× phosphate-buffered saline (PBS, 120 mM NaCl, 2.7 mM KCl, 10 mM $Na_2HPO_4$ and 2 mM $KH_2PO_4$, pH 7.4) was added to the periplasmic extract. Amylose resin was then added to the periplasmic extracts at a 1:5 ratio. The mixture was rocked at 4° C. overnight and the beads were subsequently washed 5 times with PBS. MBP or MBP/G fusion proteins were eluted with 20 mM maltose in PBS by rocking at 4° C. for an hour. Protein concentrations were determined using the Bio-Rad DC protein assay kit (Bio-Rad Laboratories, Hercules, Calif., USA). The full length fusion protein concentration was further quantitated by the Coomassie stained SDS-PAGE gel with known concentrations of bovine albumin (BSA) as the standards followed by densitometry scanning.

Characterization of Interactions Between PapD and MBP/G Fusion Proteins

The MBP or MBP/G fusion preparations from HB101/pLS101/pMAL-p4, HB101/pLS101/pMAL/G1'-19', HB101/pLS101/pMAL/G1'-81' and BH101/pLS101/pMAL/G1'-140' were applied to isoelectric focusing (IEF) pI 3–9 gels (Pharmacia Phast System, Pharmacia, Sweden) or 12.5% SDS-PAGE followed by silver staining, Coo-massie blue staining or immunoblotting with anti-PapD antiserum as described (Kuehn, et al., 1991).

The stability of the PapD-MBP/G1'-140' complex in urea was determined by incubating 1 µg partially purified MBP/G1'-140' preparation from HB100/pLS101/pMAL-G140 in 0–5 M urea for 5 minutes at 25° C. (Kuehn et al., 1991). The proteins were analyzed by IEF (pI 3–9) with silver staining. The PapD-MBP/G1'-140' complex on the IEF gel was quantified by densitometry (Digital Imaging System, Is-1000).

The interaction between PapD and MBP/G fusion in vitro was assayed by incubating purified PapD (1 µg) and amylose bead affinity purified MBP/G fusion protein (1 µg) in 4 µl PBS for 30 minutes and then applied to IEF (pI 3–9), followed by silver staining. Another in vitro assay that is more quantitative is the ELISA described below.

Characterization of the Interaction Between PapD and PapG Truncates

PapD and the PapG-truncates were co-expressed in KS474, the truncates were induced at $OD_{600}$ 0.6 with 0.5 mM IPTG and PapD under the control of the arabinose promoter was induced with 0.2% arabinose. After one hour induction, periplasmic extracts were prepared and rocked with Gal α(1–4) Gal beads overnight at 4° C. and eluted with 15 µg/ml Gal α(1–4) Gal-TMSET solution as described previously (Hultgren et al., 1989; Kuehn et al., 1991). The eluates were analyzed by acidic native gel eletrophoresis (Striker et al., 1994) followed by western blotting using anti-PapD and anti-PapG antiserum.

Hemagglutination Titers

HB101/pFJ3 harbouring various MBP/G fusion plasmids was passaged on Trypticase Soy Agar (TSA, Becton Dickinson, Cockeysville, Md., USA) three times to induce P-pili expression. At the last passage, the expression of MBP/G fusions was induced on TSA containing 100 µM IPTG. The cells from different strains were then collected and the HA titers were determined as described (Jacob-Dubuisson et al., 1993b).

Pil Preparation and Quantitation

The cells obtained from TSA plates were collected. Pili were prepared from the same amounts of cells using the procedure described previously (Jacob-Dubuisson, et al., 1993b). These pili preparations were boiled in Lammeli sample buffer with 4 M urea, then analyzed on Coomassie blue stained SDS polyacrylamide gels. The relative amount of piliation was quantified by densitometric scanning of the PapA bands.

ELISA assay

Stock solutions of MBP/G fusion proteins in PBS were diluted to 40 pmol/50 µl with PBS. The solutions of the 40 pmol/50 µl MBP/G fusion proteins were serially diluted in PBS and 50 µl of each solution were used to coat the wells of a 96-well Nunc Immunoplate (Inter Med, DK-4000 Roskilde, Denmark) overnight at 4° C. The wells were then washed with PBS and blocked with 200 µl of 3% BSA in PBS for 2 hours at 25° C. The plates were washed vigorously three times with PBS and incubated with 50 µl of PapD diluted at 50 pmol PapD in 50 µl 3% BSA-PBS for 45 minutes at 25° C. After three washings with PBS, the wells were incubated with a 1:500 dilution of rabbit anti-PapD antiserum in 3% BSA-PBS for 45 minutes at 25° C. After three washings with PBS, the wells were incubated with a 1:1000 dilution of goat antiserum to rabbit IgG coupled to alkaline phosphatase in 3% BSA-PBS for 45 minutes at 25° C. After three washings with PBS and three washings with developing buffer (10 mM diethanolamine, 0.5 MM $MgCl_2$), 50 µl of filtered 1 mg/ml p-nitrophenyl phosphate (Sigma, St. Louis, Mo., USA) in developing buffer was added. The reaction was incubated for 1 hour in the dark at 25° C. and the absorbance at 405 nm was read.

For assaying the second site peptides, all the peptides were dissolved in dimethyl sulfoxide (DMSO, Sigma, St. Louis, Mo., USA) to a final concentration 2 mM. The stock solutions were diluted to a proper concentration in PBS and coated overnight on microtiter wells at 4° C. All the peptide solutions were adjusted to the same DMSO concentration. The subsequent steps followed the procedure described above.

Results

MBP/G Fusions

To identify determinants on PapG essential for PapD interaction we constructed three in frame fusions between the MalE gene, encoding maltose binding protein, and sequences encoding the COOH-terminal residues 1'-19', 1'-81' and 1'-140' of PapG (FIG. 20). The resulting chimeric proteins were called MBP/G1'-19', MBP/G1'-81' and MBP/G1'-140', respectively, to indicate the regions of PapG present in the MBP/G fusions. MBP/G1'-19' was created since PapD was recently shown to bind a peptide consisting of the C-terminal 19 amino acids of PapD in vitro (Kuehn et al., 1993). MBP/G1'-81' and MBP/G1'-140' were created to test the requirement of the disulfide bridge (C196–C228 in PapG) for recognition by PapD. A similarly located disulfide bond is found in virtually all pilus subunits (Simons et al., 1990). MBP/G1'-81' lacks the two cysteine residues while MBP/G1'-140' contains the disulfide bond (FIG. 20).

PapD-MBP/G Interactions in vivo

The ability of PapD to bind to the MBP/G fusions was investigated using amylose affinity chromatography. (Kellermann and Ferenci, 1982). PapD was co-expressed from plasmid pLS101 (Slonim et al., 1992) with each of the MBP/G fusions. Periplasmic extracts from each strain containing the MBP/G proteins and PapD were subjected to amylose affinity chromatography and the eluates analyzed by SDS-PAGE (FIG. 21A) and by western blotting with anti-PapD antisera (FIG. 21B). In this assay, co-elution of PapD signified the ability of PapD to interact with the MBP/G protein. The western blot revealed that PapD co-eluted with all three fusion proteins (FIG. 21B, lane 2, 3 and 4) but not with the MBP control (FIGS. 21A and 21B, lane 1). However, PapD interacted much stronger with the MBP/G1'-140' fusion as can be seen in the western blot (FIG. 21B, lane 4) as well as in the coomassie blue stained gel of the eluates (FIG. 21A, lane 4). Thus, PapD interacted strongly with the MBP/G1'-140' protein and only weakly with the MBP/G1'-19' and MBP/G1'-81' proteins.

Analysis of the eluates on silver stained isoelectric focusing (IEF) gels revealed that the PapD-MBP/G1'-140' complex migrated at an isoelectric point (pI) of 5.2 (FIG. 21C, lane 4) which was intermediate between the pIs of MBP/G1'-140' (~4.4) and PapD (~9.1). This band was confirmed to contain both PapD and MBP/G1'-140' by excising the unstained band, applying the material to SDS-PAGE and analyzing it by western-blotting using anti-PapD and anti-MBP antisera (FIG. 21D). It was not possible to detect stable complexes in the eluates of MBP, MBP/G1'-19' or MBP/G1'-81' when co-expressed with PapD (FIG. 21C, lane 1, 2 and 3).

The stability of the PapD-MBP/G1'-140' complex was measured as a function of urea concentration in the presence of 15 mM DTT. Both the PapD-PapG and PapD-MBP/G1'-140' complexes behaved similarly under these conditions and were dissociated after incubation in 2M urea (data not shown). By these criteria, the PapD-MBP/G1'-140' complex was as stable as the PapD-PapG complex.

Expression of MBP/G Proteins Inhibit Pilus Formation

PapD is essential for P-pilus assembly (Hultgren et al., 1991). A decrease in the concentration of PapD in the periplasm has been shown to cause a concomitant decrease in piliation (Slonim et al., 1992). The ability of the MBP/G fusions to block pilus formation by inhibiting chaperone-subunit complex formation when co-expressed in trans with the pap operon was tested. Plasmids pMAL-p4, pMAL/G1'-19', pMAL/G1'-81' and pMAL/G1'-140' were transformed into the strain HB101/pFJ3 which contains the pap operon under the control of its own promoter in the vector pACYC184 (Jacob-Dubuisson et al. 1993b). Each MBP/G fusion protein was localized in the periplasm as determined by SDS-PAGE and western blotting with anti-MBP antisera (data not shown). Hemagglutination (HA) assays were performed on the cells co-expressing the pap operon with either MBP (pMAL-p4) or with each of the MBP/G fusions. Co-expression of the MBP/G1'-140' fusions with the pap operon decreased the HA titer 30 fold compared to the MBP control (see table 3).

TABLE 3

MBP/G fusions inhibit P pilus formation

| NBP/ proteins[a] | MBP | MBP/G1'-19' | MBP/G1'-81' | MBP/G1'-140' |
|---|---|---|---|---|
| HA titer[b] | 128 | 64 | 82 | 4 |
| Piliation percentage[c] | 100% | 50% | 40% | 10% |

[a]Plasmids pMAL-p4, pMAL/G1'-19', pMAL/G1'-81' and pMAL/G1'-140' encoding MBP, MBP-G1'-19', MBP-G1'-81' and MBP-G1'-140', respectively, were transformed into the strain HB1010/pFJ3 and the expression of pap operon and each of the MBP/G fusions was induced in each strain.
[b]Highest dilution of cell suspension yielding detectable HA
[c]The pili preparations were analyzed on Coomassie blue stained gels and the PapA bands were scanned by a densitometer. The relative piliation was determined by equating the densitometric value of PapA to 100% of the control. (HB101/pFJ3/pMAL-p4).

Co-expression of the MBP/G1'-81' and MBP/G1'-19' fusions with the pap operon had only weak effects on the HA titer (Table 3). Co-expression of MBP/G1'-140' with the pap operon reduced the amount of pili that could be purified from the cells by 90% whereas MBP/G1'-19' and MBP/G1'-81' reduced the amount of pili formed by about 50% compared to MBP alone (Table 3). Electron microscopy confirmed that cells expressing the MBP/G1'-140' fusion had little or no pili compared to the fully piliated cells co-expressing MBP (data not shown).

We hypothesized that the co-expression of the MBP/G1'-140' fusion with the pap operon inhibited pilus formation by titrating PapD away from the subunits thus driving subunits down dead end pathways of aggregation and proteolytic degradation (Hultgren et al., 1989; Holmgren et al., 1992). This hypothesis was tested as follows. pMAL-p4, pMAL/G1'-19', pMAL/G1'-81' or pMAL/G1-140' were transformed into BH101 carrying pFJ22 (Jacob-Dubuisson et al., 1994). Plasmid pFJ22 encodes papDJKEFGA under the control of the $P_{tac}$ promoter. In HB101/pFJ22, pilus subunits accumulate in the periplasmic space due to the absence of the usher, PapC. The effect of expressing each fusion on the fate of each pilus subunit type was determined by western blotting (FIG. 22). A significant decrease in the amount of PapG, PapA and PapF in cells co-expressing the MBP/G1'-140' fusion was detected arguing that the MBP/G1'-140' fusion blocked chaperone-subunit complex formation by interacting with PapD and trapping it away from pilus subunits. There was no effect on PapK and PapE stability for reasons that are not understood. Nevertheless, the fusion was capable of blocking pilus formation by interfering with the formation of critical chaperone-subunit complexes.

In vitro Chaperone Binding Assays

Figure 23A:
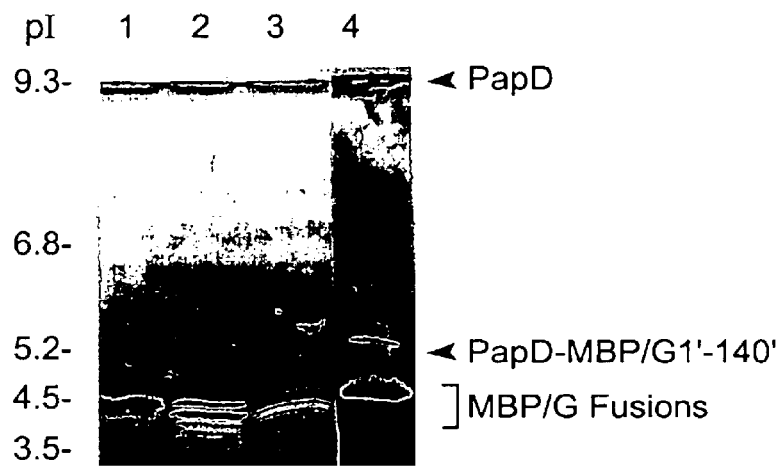
Figure 23B:
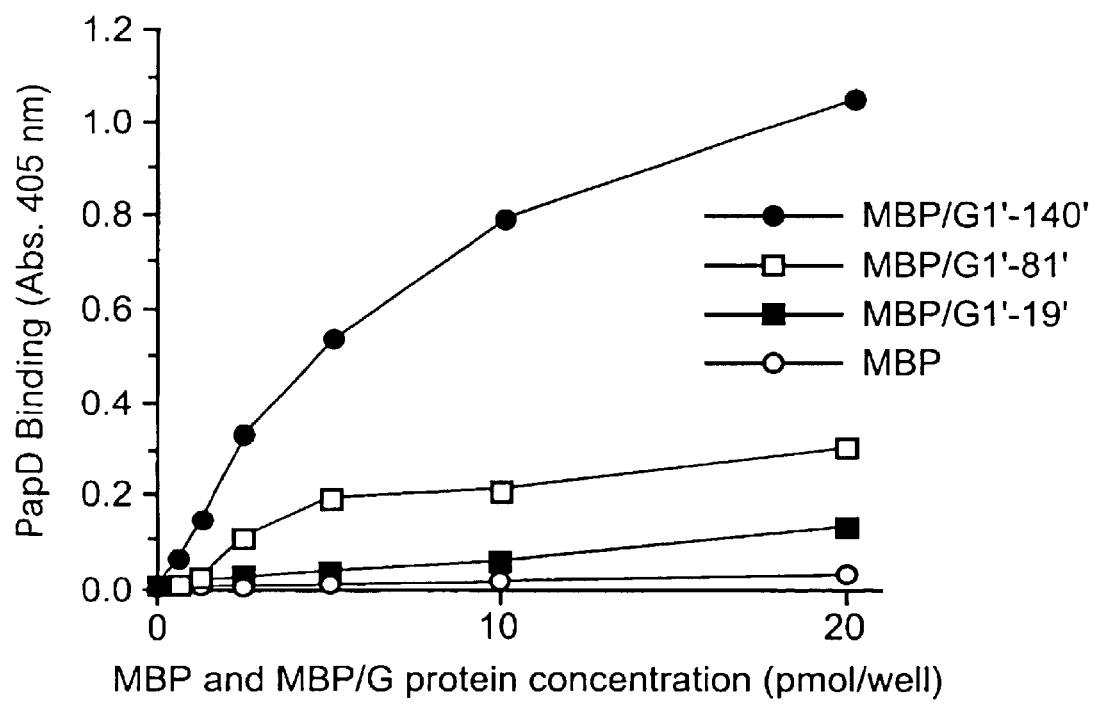

PapD binding to the MBP/G fusion proteins was further investigated using two different in vitro assays. In the first assay, purified MBP/G fusion proteins or MBP, were incubated with PapD and complex formation was analyzed on silver stained IEF gels. PapD bound to the MBP/G1'-140' fusion protein and formed a stable complex that migrated to an identical pI (5.2) as that seen for the complex formed in vivo (FIG. 23A, lane 4). In contrast, no complexes between PapD and MBP/G1'-81', MBP/G1'-19' or the MBP control were detected (FIG. 23A, lane 1, 2 and 3). In the second assay, we investigated the ability of PapD to bind to the three different MBP/G fusion proteins immobilized on microtiter wells and quantitated the interactions in an enzyme-linked immunosorbent assay (ELISA) using anti-PapD antiserum (FIG. 23B). PapD bound weakly to MBP/G1'-19', slightly better to MBP/G1'-81' but very strongly to the MBP/G1'-140'. PapD did not bind the MBP control. The dramatic increase in the affinity of PapD for the MBP/G1'-140' fusion as compared to the MBP/G1'-81' and MBP/G1'-19' fusions, suggested that residues 81' to 140' in PapG were critical for strong PapD binding.

The invariant cleft residues Arg-8 and Lys-112 in PapD have been shown to form a molecular anchor in the chaperone cleft necessary for binding pilus subunits (Slonim et al., 1992; Kuehn et al., 1993). Mutations in these residues abolished or greatly reduced the ability of PapD to bind subunits and mediate pilus assembly (Kuehn et al., 1993). Arg-8A and Lys-112A mutant PapD proteins demonstrated a greatly reduced ability to bind to the MBP/G1'-140' fusion protein both in vivo and in vitro (data not shown). These results argue that the interactions between PapD and the MBP/G1'-140' fusion are biologically relevant.

The Upstream Site is an Independent Binding Determinant

We tested the ability of PapD to bind three PapG COOH-terminal truncate proteins (shown in FIG. 20) in order to delineate the limits of the upstream PapD binding site and to test whether it was capable of functioning as an independent site. The truncate proteins were co-expressed with PapD in strain KS474 (Strauch et al., 1989) which carries a kanamycin cassette in the degP locus (degP41 mutant). Both the PapG2 and PapG3 truncates were expressed and stable in KS474, however the PapG1 truncate (removing the last 14 residues) underwent limited degradation (data not shown). Complex formation was assayed by analyzing periplasmic extracts on acid native polyacrylamide gels (Striker et al., 1994). Anti-PapD and anti-PapG antisera was used to detect the PapD-PapG complexes after western blotting (FIG. 24). PapD-PapG complexes are resolved from PapD alone on these gels due to their differences in size, shape and charge (Striker et al., 1994) PapD formed a complex with full-length PapG as well as with the PapG2 truncate (FIG. 24A, lanes 2 and 3). The complex band was also recognized by anti PapG antiserum (FIG. 24B, lanes 2 and 3). PapD did not form a complex with the PapG3 truncate (FIG. 24A & B, lane 4) which terminates at amino acid 145. This information delineates an endpoint for the second PapD binding site (as indicated in FIG. 20).

Combining the PapG truncate and the MBP/G fusion data (shown in FIG. 20) suggested that the second site on PapG recognized by PapD resided in a region between residues 117' to 141' of PapG. Four overlapping peptides were synthesized corresponding to the region between residues 120' to 156' and tested for their ability to bind PapD in an ELISA assay. Such a strategy proved successful in studying the COOH-terminal PapD binding site (Kuehn et al., 1993). The peptide corresponding to residues 125' to 140', but not the other three peptides, bound to PapD in the ELISA (FIG. 25). These data argue that PapD recognizes two surfaces on PapG. PapD forms a beta strand zippering interaction with the COOH-terminus but also recognizes a region containing residues 125'-140'.

Discussion and Conclusions

In conclusion, a chaperone binding assay was developed using fusions of the carboxyl terminus of PapG to Maltose Binding Protein (MBP/G fusions) to investigate whether chaperone-subunit complex formation requires additional interactions. PapD bound strongly to an MBP/G fusion containing the C-terminal 140 amino acids of PapG (MBP-G1'-140') but only weakly to the MBP-G1'-81', arguing that the region between the C-terminal residues 81' and 140' contains additional information that is required for strong PapD-PapG interactions. PapD was further shown to interact with a PapG C-terminal truncate containing residues 117'-314' (corresponding to a truncate consisting of the first 198 N-terminal amino acid residues of PapG), but not with a truncate containing residues 170'-314' (corresponding to a truncate consisting of the first 145 N-terminal amino acid residues of PapG).

These results together suggest that a second, independent PapD interactive site exists which does not interact with the C-terminus of the pilus subunit. This assumption is further confirmed by the fact that one of four peptides overlapping the second site region of PapG was recognized by PapD. The last result also rules out that the function of the upstream site was to exert secondary effects on the COOH terminal chaperone binding site since this region was independently capable of facilitating PapD binding.

Unlike what is true for the native subunits it was demonstrated that MBP-G1'-140' is capable of folding even in the absence of PapD and remain soluble in the periplasmic space; this folding involves the formation of an intramolecular disulphide bond. This is consistent with earlier data showing that the subunits themselves are highly folded when bound to PapD (Kuehn et al., 1991; Striker et al., 1994). However, it is not yet known whether PapD binds to subunits in vivo after they fold or whether folding occurs in the context of an interaction with PapD.

Finally, the expression of the MBP/G fusions in cells producing P pili inhibited pilus assembly to varying degrees by binding to PapD and preventing chaperone-subunit complex formation. The ability of the fusions to block pilus assembly increased as the length of the fusion protein increased. MBP-G1'-140' was a strong inhibitor of pilus assembly while MBP-G1'-81' and MBP-G1'-19' were weak inhibitors. This is consistent with the finding that residues 140'-81' contain a region necessary for strong interactions between PapD and PapG.

Recent research by the inventors has further revealed that the simultaneous expression in vivo of PapG and a modified PapD polypeptide free of domain 1 in a degP41 strain (KS474) expressing this truncated PapD results in 1) suppression of PapG toxicity in this cell line and 2) efficient partitioning into the periplasmic space of PapG. However, the pilus subunit is not correctly folded after release from PapD.

It is thus suggested by the inventors, that the binding between pilus subunits and PapD takes place by the pilus subunit binding to domain 1 and 2 of PapD. The binding between the subunit and domain 1 is important for the correct folding of the subunit, and the binding between the subunit and domain 2 is important for the transport of the subunit out into the periplasm. Whether domain 2 of PapD also participates in the folding of subunits is not known.

Since the above results are strong indicators of the existence of at least one binding site apart from the one involving Arg-8 and Lys-112 of PapD, and since it seems that this novel binding site is also very important in the net interaction between PapD and the pilus subunits, it is contemplated that also effecting this binding site will have the antibacterial effects described herein.

It is thus the plan to elucidate the motif of binding between this second binding site of PapD in manners similar to those described herein, and it is further the plan to design/identify compounds capable of interacting with this second binding site in order to ultimately synthesize compounds capable of interacting with this site in such a manner that assembly of intact pili is prevented, inhibited or enhanced.

REFERENCES

Allen B L et al., 1991, *J. Bacteriol.*, 173, 916–920.
Amit A G et al., 1988, *Science*, 230, 747–753.

Baga M et al, 1987, *Cell*, 49, 241.
Bakker et al., 1991., *Molec. Microbiol.*, 5, 875.
Ben-Naim and Marcus, 1984, *J. Chem. Phys.*, 81, 2016–2027.
Bertin Y et al., 1993, *FEMS Microbiol. Lett.*, 108, 59.
Blond-Elguindi S et al., 1993, *Cell*, 75, 717–728.
Bock K et al., 1985, *J. Biol. Chem.*, 260, 8545–8551.
Boobbyer, 1989, *J. Med. Chem.*, 32, 1083–1094.
Bothner-By A A, 1965, *Adv. Magn. Resonance*, 1, 195
Brint A T and Willet P, 1987, *J. Mol. Graphics*, 5, 49–56.
Brunger A T, 1992, X-PLOR Manual, Version 3.0, Yale Univ., New Haven.
Burkert U and Allinger N L, 1982, *Molecular Mechanics*, ACS Monographs, Washington D.C.
CCP4, The SERC, UK Collaborative Project No. 4, *A Suite of Programs for Protein Crystallography*, Darebury Laboratory, UK.
Chandler D et al., 1983, *Science*, 220, 787–794.
Clouthier S C et al., 1993, *J. Bacteriol.*, 175, 2523.
Dodson et al., 1993, *Proc. Natl. Acad. Sci.*, 90, 3670–3674.
Galyov E E et al., 1991, *FEBS Lett.*, 286, 79.
Gerlach G D, Clegg S. and Allen B L, 1989, *J. Bacteriol.*, 171, 1262–70.
Gething M-J and Sambrook J, 1992, *Nature*, 355, 33.
Goodford, 1985, *J. Med. Chem.*, 1985, 28, 849–857.
Grant G A et al., 1992, *Synthetic Peptides, A Users Guide*, W. A. Freeman and Company, New York.
Hanahan D, *J. Mol. Biol.*, 1983, 166, 557–580.
Hirschmann R et al, 1992, *J. Am. Chem. Soc.*, 114, 9217–9218.
Holmgren A et al., 1988, *J. Mol. Biol.* 203, 279.
Holmgren A and Bränden C I, 1989, *Nature*, 342, 248.
Holmgren A et al., 1992, *The EMBO Journal*, 11, 4, 1617–1622.
Hultgren S J et al., 1989, *Proc. Natl. Acad. Sci. USA*, 86, 4357.
Hull R A et al., 1981, *Infect. and Immun.*, 33, 933–938.
Hultgren S J et al., 1993, *Cell*, 73, 887–901.
Hultgren S J et al., 1989, *Proc. Natl. Acad. Sci. USA*, 86, 4357–61.
Hultgren S J et al., 1991, *Annu. Rev. Microbiol.*, 45, 383–415.
Hultgren S J et al., 1993, *Cell*, 73, 887–901.
Hällgren C and Widmalm G, 1993, *J. Carbohydr. Chem.*, 12(3), 309–333.
Iriarte et al., 1993, *Mol. Microbiol.*, 9, 507.
Jacob-Dubuisson F et al., 1993a, *Trends Microbiol.*, 1, 50–55.
Jacob-Dubuisson F et al., 1993b, *EMBO J.*, 21, 837–847.
Jacob-Dubuisson F et al., 1994, *J. Biol. Chem.*, 269, 12447–12455.
Jalajakumari M B et al., 1989, *Mol. Microbiol.*, 3, 1685.
Jones A T and Kjeldgaard M, 1994, *O Version 5.9*, Dept. Molec. Biol. Uppsala. Sweden.
Jorgensen W L, 1986, *J. Phys. Chem.*, 90, 1276–1284.
Kawaminami M et al, 1981, *Acta Crystallogr.* Section B 107(37), 2026.
Kellermann O K and Ferenci T, 1982, *Methods in Enzymology*, 90, 459–463.
Klann A G et al., 1994, *J. Bacteriol.*, 176, 2312–2317.
Klemm P et al., 1992, *Res. Microbiol.*, 143, 831.
Kuehn M. J., Normark S, and Hultgren S J., 1991. *Proc. Natl. Acad. Sci.* 88, 10586–10590.
Kuehn M. J. et al, 1993, *Science*, 262, 1234–1241.
Lam K T and Calderwood S K, 1992, *Biochem and Biophys., Res. Comm.* 184, 167.
Landry S J and Gierasch L M, 1991, *Biochemistry*, 30, 7359.
Landry S J et al., 1992, *Nature*, 355, 455.
Lee F S et al., 1992, *Prot. Eng.*, 5, 215–228.
Lindberg F et al., 1984, *EMBO J.*, 3, 1167–1173.
Lindberg F et al., 1987, *Nature*, 328, 84–87.
Lindberg F et al., 1989, *J. Bacteriol.* 171, 6052.
Lindler et al., 1993, Genbank, accession no: M86713.
Lintermans P, 1990, Thesis, Rijksuniversiteit Ghent, Belgium.
Locht C et al., 1992, *EMBO J.*, 11, 3175.
Lund B et al., 1987, *Proc. Nat. Acad. Sci. USA*, 84, 5898.
Marcus R A, 1964, *Ann. Rev. Phys. Chem.*, 15, 155–196.
Maniatis T et al., 1982, *Molecular cloning: A laboratory manual*. Cold Spring Harbor Laboratory Press, NY.
Messerschmit A and Pflugrath J W, 1987, *J. Appl. Crystallogr.*, 20, 306.
Normark S et al., Genetics and Biogenesis of *Escherichia coli* Adhesin. In *Microbial lectins and Agglutinins: Properties and Biological Activity*, D. Mirelmam (ed.), Wiley Interscience, New York, 113–143.
Otwinowski Z, 1993, *Proc. CCP4 Study Weekend 29–30, Jan* 1991. Data Collection and Processing. SERC Daresbury Lab.
Patroni J J et al, 1988, *Aust. J. Chem.*, 41, 91–102.
Pratt L R and Chandler D, 1977, *J. Chem. Phys*, 67, 3683–3704.
Åqvist J and Medina C, 1993, 206th *ACS National Meeting*, Phys: 124, *Catalogue of Abstracts*.
Åqvist J et al., 1994, *Protein Engineering*, 7(3), 385–391.

What is claimed is:

1. A novel pyranoside or a salt thereof, which is selected from the group consisting of Ethyl 2,3-O-Dibenzoyl-4-O-benzyl-1-thio-β-D-glucohexopyranoside;

Ethyl 6-O-acetyl-2,3-O-dibenzyol-4-O-benzyl-1-thio-β-D-glucohexopyranoside;

Methylglycolyl 6-O-acetyl-2,3-O-dibenzyol-4-O-benzyl-β-D-glucohexopyranoside;

2-(Hydroxy)ethyl 4-O-benzyl-β-D-glucopyranoside;

Sodium glycolyl 4-O-benzyl-β-D-glucohexopyranoside;

Methyl 2-O-ethyl-4,6-O-(4'-methoxy)phenylmethylene-α-D-mannohexopyranoside;

Methyl 2-O-ethyl-3-O-dimethyl-t-butylsilyl-4,6-O-(4'-methoxy)phenylmethylene-α-D-mannohexopyranoside;

Methyl 2-O-ethyl-3-O-dimethyl-t-butylsilyl-4-O-(4'-methoxy)benzyl-α-D-mannohexopyranoside;

Methyl 2-O-ethyl-3-O-dimethyl-t-butylsilyl-6-O-(4'-methoxy)benzyl-α-D-mannohexopyranoside;

Methyl 2-O-ethyl-3-O-dimethyl-t-butylsilyl-4-O-(4'-methoxy)benzyl-6(S)-phenyl-α-D-mannohexopyranoside;

Methyl 2,3-anhydro-4,6-O-p-methoxybenzylidene-α-D-mannohexopyranoside;

Methyl 3-azido-2-O-ethyl-4,6-O-p-methoxybenzylidene-α-D-altropyranoside;

Methyl 3-azido-3-deoxy-2-O-ethyl-4-O-p-methoxybenzyl-α-D-altro-pyranoside;

Methyl 3-azido-6-O-benzoyl-3-deoxy-2-O-ethyl-4-O-p-methoxybenzyl-α-D-altropyranoside;

Methyl 6-O-benzoyl-3-deoxy-2-O-ethyl-4-O-p-methoxybenzyl-3-sulfamino-α-D-altropyranoside sodium salt;

Methyl 6-O-benzoyl-3-deoxy-2-O-ethyl-3-sulfamino-α-D-altropyranoside ammonium salt;

Methyl 3-azido-6-O-pivaloyl-3-deoxy-2-O-ethyl-4-O-p-methoxybenzyl-α-D-altropyranoside;

Methyl 6-O-pivaloyl-3-deoxy-2-O-ethyl-4-O-p-methoxybenzyl-3-sulfamino-α-D-altropyranoside sodium salt;

Methyl 6-O-pivaloyl-3-deoxy-2-O-ethyl-3-sulfamino-α-D-altropyranoside ammonium salt;

Methyl 6-O-pivaloyl-3-deoxy-2-O-ethyl-4-O-p-methoxybenzyl-3-tbutyloxamido-α-D-altropyranoside;

Methyl 6-O-pivaloyl-3-deoxy-2-O-ethyl-3-oxamido-α-D-altropyranoside ammonium salt;

Methyl 3-azido-6-O-pyrrol-3'-ylcarboxyl-3-deoxy-2-O-ethyl-4-O-p-methoxybenzyl-α-D-altropyranoside; and Methyl 6-O-pyrrol-3'-ylcarboxyl-3-deoxy-2-O-ethyl-3-sulfamino-α-D-altropyranoside ammonium salt.

2. A novel compound of formula

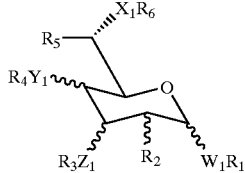

wherein $W_1$ is O or S;

$R_1$ is —$CH_3$; ethyl; —$CH_2CH_2OH$, —$CHCOOCH_3$; or —CHCOOH;

$R_2$ is —$OCH_2CH_3$; OH; $O(CO)W_{11}$, wherein $W_{11}$ is an aryl group;

$Z_1R_3$ is OH; $O(CO)W_{11}$, wherein $W_{11}$ is an aryl group; O-dimethyl-t-butyl-silyl; $N_3$; —$NHSO_2(OH)$; t-butyloxamide; oxamide; or a salt thereof or $R_2$ and $Z_2R_3$ form an epoxide bond;

$Y_1$ is O;

$R_4$ is H; -p-methoxybenzyl; —$CH_2$-$Q_{14}$, wherein $Q_{14}$ is an aryl group;

$R_5$ is H or phenyl;

$R_6$ is H, -p-methyoxybenzyl; benzoyl; pivaloyl; or N-pyrrol-3'-yl-carboxyl; or $R_4$ and $R_6$ form a 4-methoxyphenylmethylidene ring.

3. A novel compound of formula

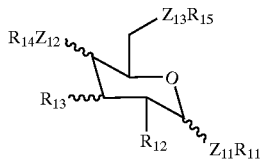

wherein $Z_{11}$ is O or S;

$R_{11}$ is ethyl; —$CH_2CH_2OH$; $CHCOOCH_3$; CHCOOH; or a salt thereof;

$R_{12}$ and $R_{13}$ are independently OH or $O(CO)W_{11}$, wherein $W_{11}$ is aryl group;

$Z_{12}$ is O;

$R_{14}$ is —$CH_2$-$Q_{14}$, wherein $Q_{14}$ is an aryl group;

$Z_{13}$ is O or —OOCCH$_2$—;

$R_{15}$ is H;

or a salt thereof.

4. A composition comprising a compound according to claim 2 in combination with at least one pharmaceutically acceptable carrier or excipient.

5. A composition according to claim 4, further comprising at least one additional pharmaceutical substance.

6. A composition according to claim 5, wherein said additional pharmaceutical substance is an antibacterial agent selected from the group consisting of penicillins, cephalosporins, aminoglycosides, sulfonamides, tetracyclines, chloramphenicol, polymixins, antimycobacterial drugs, and urinary antiseptics.

7. A composition comprising a compound according to claim 3 combination with at least one pharmaceutically acceptable carrier or excipient.

8. A composition according to claim 7, further comprising at least one additional pharmaceutical substance.

9. A composition according to claim 8, wherein said additional pharmaceutical substance is an antibacterial agent selected from the group consisting of penicillins, cephalosporins, aminoglycosides, sulfonamides, tetracyclines, chloramphenicol, polymixins, antimycobacterial drugs, and urinary antiseptics.

10. A composition comprising a compound according to claim 1 in combination with at least one pharmaceutically acceptable carrier or excipient.

11. A composition according to claim 10, further comprising at least one additional pharmaceutical substance.

12. A composition according to claim 11, wherein said additional pharmaceutical substance is an antibacterial agent selected from the group consisting of penicillins, cephalosporins, aminoglycosides, sulfonamides, tetracyclines, chloramphenicol, polymixins, antimycobacterial drugs, and urinary antiseptics.

* * * * *